United States Patent [19]

Vazquez et al.

[11] Patent Number: 6,060,476
[45] Date of Patent: May 9, 2000

[54] α- AND β-AMINO ACID HYDROXYETHYLAMINO SULFONAMIDES USEFUL AS RETROVIRAL PROTEASE INHIBITORS

[75] Inventors: Michael L. Vazquez, Gurnee; Richard A. Mueller, Glencoe, both of Ill.; John J. Talley, St. Louis, Mo.; Daniel P Getman, Chesterfield, Mo.; Gary A. DeCrescenzo, St. Peters, Mo.; John N. Freskos, Clayton, Mo.; Robert M. Heintz, Ballwin, Mo.; Deborah E. Bertenshaw, Brentwood, Mo.

[73] Assignee: G. D. Searle & Co., Skokie, Ill.

[21] Appl. No.: 08/204,827

[22] Filed: Mar. 2, 1994

Related U.S. Application Data

[63] Continuation-in-part of application No. PCT/US93/07814, Aug. 24, 1993, which is a continuation-in-part of application No. 07/934,984, Aug. 25, 1992, abandoned.

[51] Int. Cl.$^7$ .................... A61K 31/505; C07D 239/02; C07D 211/78; C07D 277/30
[52] U.S. Cl. .................. 514/256; 514/277; 514/365; 544/335; 546/323; 546/337; 548/204; 560/13
[58] Field of Search .................. 549/65, 475; 544/335; 546/323, 337; 548/204; 560/13; 514/256, 277, 365

[56] References Cited

U.S. PATENT DOCUMENTS 5,585,397  12/1996  Tung et al. .................. 514/473

FOREIGN PATENT DOCUMENTS

WO 94/05639  3/1994  WIPO .

Primary Examiner—Johann Richter
Assistant Examiner—Ebenezer Sackey
Attorney, Agent, or Firm—Banner & Witcoff, Ltd.

[57] ABSTRACT

α- and β-amino acid hydroxyethylamino sulfonamide compounds are effective as retroviral protease inhibitors, and in particular as inhibitors of HIV protease.

12 Claims, No Drawings

α- AND β-AMINO ACID HYDROXYETHYLAMINO SULFONAMIDES USEFUL AS RETROVIRAL PROTEASE INHIBITORS

RELATED APPLICATION

This application is a continuation in part application of co-owned and PCT/US93/07814, filed Aug. 24, 1993, which is a continuation in part application of co-owned U.S. patent application Ser. No. 07/934,984 filed Aug. 25, 1992, now abandoned.

BACKGROUND OF THE INVENTION

1. Field of the Invention

The present invention relates to retroviral protease inhibitors and, more particularly, relates to novel compounds and a composition and method for inhibiting retroviral proteases. This invention, in particular, relates to sulfonamide-containing hydroxyethylamine protease inhibitor compounds, a composition and method for inhibiting retroviral proteases such as human immunodeficiency virus (HIV) protease and for treating a retroviral infection, e.g., an HIV infection. The subject invention also relates to processes for making such compounds as well as to intermediates useful in such processes.

2. Related Art

During the replication cycle of retroviruses, gag and gag-pol gene products are translated as proteins. These proteins are subsequently processed by a virally encoded protease (or proteinase) to yield viral enzymes and structural proteins of the virus core. Most commonly, the gag precursor proteins are processed into the core proteins and the pol precursor proteins are processed into the viral enzymes, e.g., reverse transcriptase and retroviral protease. It has been shown that correct processing of the precursor proteins by the retroviral protease is necessary for assembly of infectious virons. For example, it has been shown that frameshift mutations in the protease region of the pol gene of HIV prevents processing of the gag precursor protein. It has also been shown through site-directed mutagenesis of an aspartic acid residue in the HIV protease that processing of the gag precursor protein is prevented. Thus, attempts have been made to inhibit viral replication by inhibiting the action of retroviral proteases.

Retroviral protease inhibition may involve a transition-state mimetic whereby the retroviral protease is exposed to a mimetic compound which binds to the enzyme in competition with the gag and gag-pol proteins to thereby inhibit replication of structural proteins and, more importantly, the retroviral protease itself. In this manner, retroviral replication proteases can be effectively inhibited.

Several classes of compounds have been proposed, particularly for inhibition of proteases, such as for inhibition of HIV protease. Such compounds include hydroxyethylamine isosteres and reduced amide isosteres. See, for example, EP O 346 847; EP O 342,541; Roberts et al, "Rational Design of Peptide-Based Proteinase Inhibitors, "Science, 248, 358 (1990); and Erickson et al, "Design Activity, and 2.8Å Crystal Structure of a $C_2$ Symmetric Inhibitor Complexed to HIV-1 Protease," Science, 249, 527 (1990).

Several classes of compounds are known to be useful as inhibitors of the proteolytic enzyme renin. See, for example, U.S. Pat. No. 4,599,198; U.K. 2,184,730; G.B. 2,209,752; EP O 264 795; G.B. 2,200,115 and U.S. SIR H725. Of these, G.B. 2,200,115, GB 2,209,752, EP O 264,795, U.S. SIR H725 and U.S. Pat. No. 4,599,198 disclose urea-containing hydroxyethylamine renin inhibitors. EP 468 641 discloses renin inhibitors and intermediates for the preparation of the inhibitors, which include sulfonamide-containing hydroxyethylamine compounds, such as 3-(t-butoxycarbonyl)amino-cyclohexyl-1-(phenylsulfonyl)amino-2(5)-butanol. G.B. 2,200,115 also discloses sulfamoyl-containing hydroxyethylamine renin inhibitors, and EP 0264 795 discloses certain sulfonamide-containing hydroxyethylamine renin inhibitors. However, it is known that, although renin and HIV proteases are both classified as aspartyl proteases, compounds which are effective renin inhibitors generally cannot be predicted to be effective HIV protease inhibitors.

BRIEF DESCRIPTION OF THE INVENTION

The present invention is directed to virus inhibiting compounds and compositions. More particularly, the present invention is directed to retroviral protease inhibiting compounds and compositions, to a method of inhibiting retroviral proteases, to processes for preparing the compounds and to intermediates useful in such processes. The subject compounds are characterized as sulfonamide-containing hydroxyethylamine inhibitor compounds.

DETAILED DESCRIPTION OF THE INVENTION

In accordance with the present invention, there is provided a retroviral protease inhibiting compound of the formula:

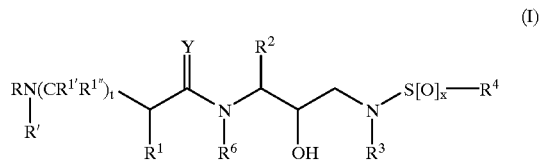

(I)

or a pharmaceutically acceptable salt, prodrug or ester thereof wherein:

R represents hydrogen, alkoxycarbonyl, aralkoxycarbonyl, alkylcarbonyl, cycloalkylcarbonyl, cycloalkylalkoxycarbonyl, cycloalkylalkanoyl, alkanoyl, aralkanoyl, aroyl, aryloxycarbonyl, aryloxycarbonylalkyl, aryloxyalkanoyl, heterocyclylcarbonyl, heterocyclyloxycarbonyl, heterocyclylalkanoyl, heterocyclylalkoxycarbonyl, heteroaralkanoyl, heteroaralkoxycarbonyl, heteroaryloxycarbonyl, heteroaroyl, alkyl, alkenyl, alkynyl, cycloalkyl, aryl, aralkyl, aryloxyalkyl, heteroaryloxyalkyl, hydroxyalkyl, aminocarbonyl, aminoalkanoyl, and mono- and disubstituted aminocarbonyl and mono- and disubstituted aminoalkanoyl radicals wherein the substituents are selected from alkyl, aryl, aralkyl, cycloalkyl, cycloalkylalkyl, heteroaryl, heteroaralkyl, heterocycloalkyl, heterocycloalkylalkyl radicals, or where said aminocarbonyl and aminoalkanoyl radicals are disubstituted, said substituents along with the nitrogen atom to which they are attached form a heterocycloalkyl or heteroaryl radical;

R' represents hydrogen, radicals as defined for $R^3$ or R"$SO_2$-wherein R" represents radicals as defined for $R^3$; or R and R' together with the nitrogen to which they are attached represent heterocycloalkyl and heteroaryl radicals;

$R^1$ represents hydrogen, $-CH_2SO_2NH_2$, $-CH_2CO_2CH_3$, $-CO_2CH_3$, $-CONH_2$, $-CH_2C(O)$ NHCH$_3$, —C(CH$_3$)$_2$ (SH), —C(CH$_3$)$_2$(SCH$_3$), —C(CH$_3$)$_2$(S[O]CH$_3$), —C(CH$_3$)$_2$(S[O]$_2$CH$_3$), alkyl, haloalkyl, alkenyl, alkynyl and cycloalkyl radicals, and amino acid side chains selected from asparagine, S-methyl cysteine and the sulfoxide (SO) and sulfone (SO$_2$) derivatives thereof, isoleucine, allo-isoleucine, alanine, leucine, tert-leucine, phenylalanine, ornithine, histidine, norleucine, glutamine, threonine, glycine, allothreonine, serine, O-alkyl serine, aspartic acid, beta-cyano alanine and valine side chains;

R$^{1'}$ and R$^{1'''}$ independently represent hydrogen and radicals as defined for R$^1$, or one of R$^{1'}$ and R$^{1'''}$, together with R$^1$ and the carbon atoms to which R$^1$, R$^{1'}$ and R$^{1'''}$ are attached, represent a cycloalkyl radical;

R$^2$ represents alkyl, aryl, cycloalkyl, cycloalkylalkyl and aralkyl radicals, which radicals are optionally substituted with a group selected from alkyl and halogen radials, —NO$_2$, —CN, —CF$_3$, —OR$^9$ and —SR$^9$, wherein R$^9$ represents hydrogen and alkyl radicals, and halogen radicals;

R$^3$ represents hydrogen, alkyl, haloalkyl, alkenyl, alkynyl, hydroxyalkyl, alkoxyalkyl, cycloalkyl, cycloalkylalkyl, heterocycloalkyl, heteroaryl, heterocycloalkylalkyl, aryl, aralkyl, heteroaralkyl, aminoalkyl and mono- and disubstituted aminoalkyl radicals, wherein said substituents are selected from alkyl, aryl, aralkyl, cycloalkyl, cycloalkylalkyl, heteroaryl, heteroaralkyl, heterocycloalkyl, and heterocycloalkylalkyl radicals, or in the case of a disubstituted aminoalkyl radical, said substituents along with the nitrogen atom to which they are attached, form a heterocycloalkyl or a heteroaryl radical;

R$^4$ represents radicals as defined by R$^3$ except for hydrogen;

R$^6$ represents hydrogen and alkyl radicals;

x represents 0, 1 or 2;

t represents either 0 or 1; and

Y represents O, S and NR$^{15}$ wherein R$^{15}$ represents hydrogen and radicals as defined for R$^3$.

A family of compounds of particular interest within Formula I are compounds embraced by Formula II:

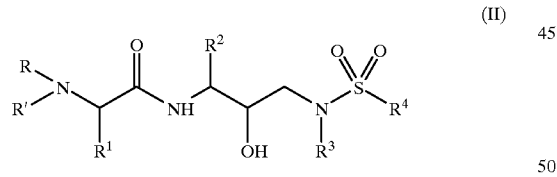

(II)

wherein:
R represents hydrogen, alkoxycarbonyl, aralkoxycarbonyl, alkylcarbonyl, cycloalkylcarbonyl, cycloalkylalkoxycarbonyl, cycloalkylalkanoyl, alkanoyl, aralkanoyl, aroyl, aryloxycarbonyl, aryloxycarbonylalkyl, aryloxyalkanoyl, heterocyclylcarbonyl, heterocyclyloxycarbonyl, heterocyclylalkanoyl, heterocyclylalkoxycarbonyl, heteroaralkanoyl, heteroaralkoxycarbonyl, heteroaryloxy-carbonyl, heteroaroyl, alkyl, alkenyl, cycloalkyl, aryl, aralkyl, aryloxyalkyl, heteroaryloxyalkyl, hydroxyalkyl, aminocarbonyl, aminoalkanoyl, and mono- and disubstituted aminocarbonyl and mono- and disubstituted aminoalkanoyl radicals wherein the substituents are selected from alkyl, aryl, aralkyl, cycloalkyl, cycloalkylalkyl, heteroaryl, heteroaralkyl, heterocycloalkyl, heterocycloalkyalkyl radicals, or where said aminoalkanoyl radical is disubstituted, said substituents along with the nitrogen atom to which they are attached form a heterocycloalkyl or heteroaryl radical;

R' represents hydrogen and radicals as defined for R$^3$ or R and R' together with the nitrogen to which they are attached represent heterocycloalkyl and heteroaryl radical;

R$^1$ represents hydrogen, —CH$_2$SO$_2$NH$_2$, —CH$_2$CO$_2$CH$_3$, —CO$_2$CH$_3$, —CONH$_2$, —CH$_2$C(O)NHCH$_3$, —C(CH$_3$)$_2$(SH), —C(CH$_3$)$_2$(SCH$_3$), —C(CH$_3$)$_2$(S[O]CH$_3$), —C(CH$_3$)$_2$(S[O]$_2$CH$_3$), alkyl, haloalkyl, alkenyl, alkynyl and cycloalkyl radicals, and amino acid side chains selected from asparagine, S-methyl cysteine and the sulfoxide (SO) and sulfone (SO$_2$) derivatives thereof, isoleucine, allo-isoleucine, alanine, leucine, tert-leucine, phenylalanine, ornithine, histidine, norleucine, glutamine, threonine, glycine, allo-threonine, serine, O-methyl serine, aspartic acid, beta-cyano alanine and valine side chains;

R$^2$ represents alkyl, aryl, cycloalkyl, cycloalkylalkyl and aralkyl radicals, which radicals are optionally substituted with a group selected from alkyl and halogen radials, —NO$_2$, —C≡N, CF$_3$, —OR$^9$, —SR$^9$, wherein R$^9$ represents hydrogen and alkyl radicals;

R$^3$ represents alkyl, haloalkyl, alkenyl, alkynyl, hydroxyalkyl, alkoxyalkyl, cycloalkyl, cycloalkylalkyl, heterocycloalkyl, heteroaryl, heterocycloalkylalkyl, aryl, aralkyl, heteroaralkyl, aminoalkyl and mono- and disubstituted aminoalkyl radicals, wherein said substituents are selected from alkyl, aryl, aralkyl, cycloalkyl, cycloalkylalkyl, heteroaryl, heteroaralkyl, heterocycloalkyl, and heterocycloalkylalkyl radicals, or in the case of a disubstituted aminoalkyl radical, said substituents along with the nitrogen atom to which they are attached, form a heterocycloalkyl or a heteroaryl radical; and R$^4$ represents radicals as defined by R$^3$.

A more preferred family of compounds within Formula II consists of compounds wherein:

R represents hydrogen, alkoxycarbonyl, aralkoxycarbonyl, alkylcarbonyl, cycloalkylcarbonyl, cycloalkylalkoxycarbonyl, cycloalkylalkanoyl, alkanoyl, aralkanoyl, aroyl, aryloxycarbonyl, aryloxycarbonylalkyl, aryloxyalkanoyl, heterocyclylcarbonyl, heterocyclyloxycarbonyl, heterocyclylalkanoyl, heterocyclylalkoxycarbonyl, heteroaralkanoyl, heteroaralkoxycarbonyl, heteroaryloxy-carbonyl, heteroaroyl, alkyl, alkenyl, cycloalkyl, aryl, aralkyl, aryloxyalkyl, heteroaryloxyalkyl, hydroxyalkyl, aminocarbonyl, aminoalkanoyl, and mono- and disubstituted aminocarbonyl and mono- and disubstituted aminoalkanoyl radicals wherein the substituents are selected from alkyl, aryl, aralkyl, cycloalkyl, cycloalkylalkyl, heteroaryl, heteroaralkyl, heterocycloalkyl, heterocycloalkyalkyl radicals, or where said aminoalkanoyl radical is disubstituted, said substituents along with the nitrogen atom to which they are attached form a heterocycloalkyl or heteroaryl radical;

R' represents hydrogen and radicals as defined for R$^3$ or R and R' together with the nitrogen to which they are attached represent heterocycloalkyl and heteroaryl radical;

R$^1$ represents CH$_2$C(O)NHCH$_3$, C(CH$_3$)$_2$(SCH$_3$), C(CH$_3$)$_2$(S[O]CH$_3$), C(CH$_3$)$_2$(S[O]$_2$CH$_3$), alkyl, alkenyl and alkynyl radicals, and amino acid side chains selected from the group consisting of asparagine, valine, threonine, allo-threonine, isoleucine, tert-leucine, S-methyl cysteine and the sulfone and sulfoxide derivatives thereof, alanine, and allo-isoleucine;

$R^2$ represents alkyl, cycloalkylalkyl and aralkyl radicals, which radicals are optionally substituted with halogen radicals and radicals represented by the formula —$OR^9$ and —$SR^9$ wherein $R^9$ represents alkyl radicals; and $R^3$ and $R^4$ independently represent alkyl, alkenyl, alkoxyalkyl, cycloalkyl, cycloalkylalkyl, heterocycloalkyl, heterocycloalkylalkyl, aryl, aralkyl and heteroaralkyl radicals.

Of highest interest are compounds within Formula II wherein

R represents alkoxycarbonyl, aralkoxycarbonyl, alkylcarbonyl, cycloalkylcarbonyl, cycloalkylalkoxycarbonyl, cycloalkylalkanoyl, alkanoyl, aralkanoyl, aroyl, aryloxycarbonyl, aryloxycarbonylalkyl, aryloxyalkanoyl, heterocyclylcarbonyl, heterocyclyloxycarbonyl, heterocyclylalkanoyl, heterocyclylalkoxycarbonyl, heteroaralkanoyl, heteroaralkoxycarbonyl, heteroaryloxy-carbonyl, heteroaroyl, aminocarbonyl, aminoalkanoyl, and mono- and disubstituted aminocarbonyl and mono- and disubstituted aminoalkanoyl radicals wherein the substituents are selected from alkyl, aryl, aralkyl, cycloalkyl, cycloalkylalkyl, heteroaryl, heteroaralkyl, heterocycloalkyl, heterocycloalkylalkyl radicals, or where said aminoalkanoyl radical is disubstituted, said substituents along with the nitrogen atom to which they are attached form a heterocycloalkyl or heteroaryl radical;

R' represents hydrogen and radicals as defined for $R^3$ or R and R' together with the nitrogen to which they are attached represent heterocycloalkyl and heteroaryl radical;

$R^1$ represents $CH_2C(O)NHCH_3$, $C(CH_3)_2(SCH_3)$, $C(CH_3)_2(S[O]CH_3)$, $C(CH_3)_2(S[O]_2CH_3)$, methyl, propargyl, t-butyl, isopropyl and sec-butyl radicals, and amino acid side chains selected from the group consisting of asparagine, valine, S-methyl cysteine, allo-iso-leucine, iso-leucine, and beta-cyano alanine side chains;

$R^2$ represents $CH_3SCH_2CH_2$—, iso-butyl, n-butyl, benzyl, 4-fluorobenzyl, 2-naphthylmethyl and cyclohexylmethyl radicals;

$R^3$ represents isoamyl, n-butyl, isobutyl and cyclohexyl radicals; and $R^4$ represents phenyl, substituted phenyl and methyl radicals.

Another family of compounds of particular interest within Formula I are compounds embraced by Formula III:

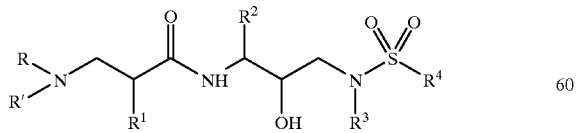

(III)

wherein:

R represents hydrogen, alkoxycarbonyl, aralkoxycarbonyl, alkylcarbonyl, cycloalkylcarbonyl, cycloalkylalkoxycarbonyl, cycloalkylalkanoyl, alkanoyl, aralkanoyl, aroyl, aryloxycarbonyl, aryloxycarbonylalkyl, aryloxyalkanoyl, heterocyclylcarbonyl, heterocyclyloxycarbonyl, heterocyclylalkanoyl, heterocyclylalkoxycarbonyl, heteroaralkanoyl, heteroaralkoxycarbonyl, heteroaryloxy-carbonyl, heteroaroyl, alkyl, alkenyl, cycloalkyl, aryl, aralkyl, aryloxyalkyl, heteroaryloxyalkyl, hydroxyalkyl, aminocarbonyl, aminoalkanoyl, and mono- and disubstituted aminocarbonyl and mono- and disubstituted aminoalkanoyl radicals wherein the substituents are selected from alkyl, aryl, aralkyl, cycloalkyl, cycloalkylalkyl, heteroaryl, heteroaralkyl; heterocycloalkyl, heterocycloalkyalkyl radicals, or where said aminoalkanoyl radical is disubstituted, said substituents along with the nitrogen atom to which they are attached form a heterocycloalkyl or heteroaryl radical;

R' represents hydrogen and radicals as defined for $R^3$ or R and R' together with the nitrogen to which they are attached represent heterocycloalkyl and heteroaryl radical;

$R^1$ represents hydrogen, —$CH_2SO_2NH_2$, —$CH_2CO_2CH_3$, —$CO_2CH_3$, —$CONH_2$, —$CH_2C(O)NHCH_3$, —$C(CH_3)_2(SH)$, —$C(CH_3)_2(SCH_3)$, —$C(CH_3)_2(S[O]CH_3)$, —$C(CH_3)_2(S[O]_2CH_3)$, alkyl, haloalkyl, alkenyl, alkynyl and cycloalkyl radicals, and amino acid side chains selected from asparagine, S-methyl cysteine and the sulfoxide (SO) and sulfone ($SO_2$) derivatives thereof, isoleucine, allo-isoleucine, alanine, leucine, tert-leucine, phenylalanine, ornithine, histidine, norleucine, glutamine, threonine, glycine, allo-threonine, serine, aspartic acid, beta-cyano alanine and valine side chains;

$R^2$ represents alkyl, aryl, cycloalkyl, cycloalkylalkyl and aralkyl radicals, which radicals are optionally substituted with a group selected from alkyl and halogen radicals, —$NO_2$, —C≡N, $CF_3$, —$OR^9$, —$SR^9$; wherein $R^9$ represents hydrogen and alkyl;

$R^3$ represents alkyl, haloalkyl, alkenyl, alkynyl, hydroxyalkyl, alkoxyalkyl, cycloalkyl, cycloalkylalkyl, heterocycloalkyl, heteroaryl, heterocycloalkylalkyl, aryl, aralkyl, heteroaralkyl, aminoalkyl and mono- and disubstituted aminoalkyl radicals, wherein said substituents are selected from alkyl, aryl, aralkyl, cycloalkyl, cycloalkylalkyl, heteroaryl, heteroaralkyl, heterocycloalkyl, and heterocycloalkylalkyl radicals, or in the case of a disubstituted aminoalkyl radical, said substituents along with the nitrogen atom to which they are attached, form a heterocycloalkyl or a heteroaryl radical; and $R^4$ represents radicals as defined by $R^3$.

A more preferred family of compounds within Formula III consists of compounds wherein R represents hydrogen, alkoxycarbonyl, aralkoxycarbonyl, alkylcarbonyl, cycloalkylcarbonyl, cycloalkylalkoxycarbonyl, cycloalkylalkanoyl, alkanoyl, aralkanoyl, aroyl, aryloxycarbonyl, aryloxycarbonylalkyl, aryloxyalkanoyl, heterocyclylcarbonyl, heterocyclyloxycarbonyl, heterocyclylalkanoyl, heterocyclylalkoxycarbonyl, heteroaralkanoyl, heteroaralkoxycarbonyl, heteroaryloxy-carbonyl, heteroaroyl, alkyl, alkenyl, cycloalkyl, aryl, aralkyl, aryloxyalkyl, heteroaryloxyalkyl, hydroxyalkyl, aminocarbonyl, aminoalkanoyl, and mono- and disubstituted aminocarbonyl and mono- and disubstituted aminoalkanoyl radicals wherein the substituents are selected from alkyl, aryl, aralkyl, cycloalkyl, cycloalkylalkyl, heteroaryl, heteroaralkyl, heterocycloalkyl, heterocycloalkyalkyl radicals, or where said aminoalkanoyl radical is disubstituted, said substituents along with the nitrogen atom to which they are attached form a heterocycloalkyl or heteroaryl radical;

R' represents hydrogen and radicals as defined for $R^3$ or R and R' together with the nitrogen to which they are attached represent heterocycloalkyl and heteroaryl radical;

$R^1$ represents hydrogen, alkyl and alkenyl radicals, and amino acid side chains selected from the group consisting of asparagine, valine, threonine, allo-threonine, isoleucine, tert-leucine, S-methyl cysteine and the sulfone and sulfoxide derivatives thereof, alanine, and allo-isoleucine;

$R^2$ represents alkyl, cycloalkylalkyl and aralkyl radicals, which radicals are optionally substituted with halogen radicals and radicals represented by the formula —$OR^9$ and —$SR^9$ wherein $R^9$ represents hydrogen and alkyl and halogen radicals; and $R^3$ and $R^4$ independently represent alkyl, alkenyl, alkoxyalkyl, cycloalkyl, cycloalkylalkyl, heterocycloalkyl, heterocycloalkylalkyl, aryl, aralkyl, heteroaryl and heteroaralkyl radicals.

Of highest interest are compounds within Formula III wherein

R represents hydrogen, alkoxycarbonyl, aralkoxycarbonyl, alkylcarbonyl, cycloalkylcarbonyl, cycloalkylalkoxycarbonyl, cycloalkylalkanoyl, alkanoyl, aralkanoyl, aroyl, aryloxycarbonyl, aryloxycarbonylalkyl, aryloxyalkanoyl, heterocyclylcarbonyl, heterocyclyloxycarbonyl, heterocyclylalkanoyl, heterocyclylalkoxycarbonyl, heteroaralkanoyl, heteroaralkoxycarbonyl, heteroaryloxy-carbonyl, heteroaroyl, aminocarbonyl, aminoalkanoyl, and mono- and disubstituted aminocarbonyl and mono- and disubstituted aminoalkanoyl radicals wherein the substituents are selected from alkyl, aryl, aralkyl, cycloalkyl, cycloalkylalkyl, heteroaryl, heteroaralkyl, heterocycloalkyl, heterocycloalkyalkyl radicals, or where said aminoalkanoyl radical is disubstituted, said substituents along with the nitrogen atom to which they are attached form a heterocycloalkyl or heteroaryl radical;

R' represents hydrogen and radicals as defined for $R^3$ or R and R' together with the nitrogen to which they are attached represent heterocycloalkyl and heteroaryl radical;

$R^1$ represents hydrogen, methyl, propargyl, t-butyl, isopropyl and sec-butyl radicals, and amino acid side chains selected from the group consisting of asparagine, valine, S-methyl cysteine, allo-iso-leucine, iso-leucine, threonine, serine, aspartic acid, beta-cyano alanine, and allo-threonine side chains;

$R^2$ represents $CH_3SCH_2CH_2$—, iso-butyl, n-butyl, benzyl, 4-fluorobenzyl, 2-naphthylmethyl and cyclohexylmethyl radicals; and $R^3$ represents alkyl, cyclohexyl, isobutyl, isoamyl, and n-butyl radicals; and $R^4$ represents methyl, phenyl and substituted phenyl radicals wherein the substituents are selected from halo, alkoxy, hydroxy, nitro and amino substituents.

Another family of compounds of particular interest within Formula I are compounds embraced by Formula IV:

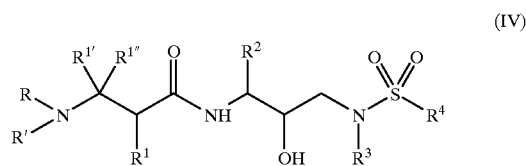

wherein:

R represents hydrogen, alkoxycarbonyl, aralkoxycarbonyl, alkylcarbonyl, cycloalkylcarbonyl, cycloalkylalkoxycarbonyl, cycloalkylalkanoyl, alkanoyl, aralkanoyl, aroyl, aryloxycarbonyl, aryloxycarbonylalkyl, aryloxyalkanoyl, heterocyclylcarbonyl, heterocyclyloxycarbonyl, heterocyclylalkanoyl, heterocyclylalkoxycarbonyl, heteroaralkanoyl, heteroaralkoxycarbonyl, heteroaryloxy-carbonyl, heteroaroyl, alkyl, alkenyl, cycloalkyl, aryl, aralkyl, aryloxyalkyl, heteroaryloxyalkyl, hydroxyalkyl, aminocarbonyl, aminoalkanoyl, and mono- and disubstituted aminocarbonyl and mono- and disubstituted aminoalkanoyl radicals wherein the substituents are selected from alkyl, aryl, aralkyl, cycloalkyl, cycloalkylalkyl, heteroaryl, heteroaralkyl, heterocycloalkyl, heterocycloalkyalkyl radicals, or where said aminoalkanoyl radical is disubstituted, said substituents along with the nitrogen atom to which they are attached form a heterocycloalkyl or heteroaryl radical;

R' represents hydrogen and radicals as defined for $R^3$ or R and R' together with the nitrogen to which they are attached represent heterocycloalkyl and heteroaryl radical;

$R^1$ represents hydrogen, —$CH_2SO_2NH_2$, —$CH_2CO_2CH_3$, —$CO_2CH_3$, —$CONH_2$, —$CH_2C(O)NHCH_3$, —$C(CH_3)_2(SH)$, —$C(CH_3)_2(SCH_3)$, —$C(CH_3)_2(S[O]CH_3)$, —$C(CH_3)_2(S[O]_2CH_3)$, alkyl, haloalkyl, alkenyl, alkynyl and cycloalkyl radicals, and amino acid side chains selected from asparagine, S-methyl cysteine and the sulfoxide (SO) and sulfone ($SO_2$) derivatives thereof, isoleucine, allo-isoleucine, alanine, leucine, tert-leucine, phenylalanine, ornithine, histidine, norleucine, glutamine, threonine, glycine, allo-threonine, serine, aspartic acid, beta-cyano alanine and valine side chains;

$R^{1'}$ and $R^{1''}$ independently represent hydrogen and radicals as defined for $R^1$, or one of $R^{1'}$ and $R^{1''}$, together with $R^1$ and the carbon atoms to which $R^1$, $R^{1'}$ and $R^{1''}$ are attached, represent a cycloalkyl radical;

$R^2$ represents alkyl, aryl, cycloalkyl, cycloalkylalkyl and aralkyl radicals, which radicals are optionally substituted with a group selected from alkyl and halogen radials, —$NO_2$, —C≡N, $CF_3$, —$OR^9$ and —$SR^9$, wherein $R^9$ represents hydrogen and alkyl radicals;

$R^3$ represents alkyl, haloalkyl, alkenyl, alkynyl, hydroxyalkyl, alkoxyalkyl, cycloalkyl, cycloalkylalkyl, heterocycloalkyl, heteroaryl, heterocycloalkylalkyl, aryl, aralkyl, heteroaralkyl, aminoalkyl and mono- and disubstituted aminoalkyl radicals, wherein said substituents are selected from alkyl, aryl, aralkyl, cycloalkyl, cycloalkylalkyl, heteroaryl, heteroaralkyl, heterocycloalkyl, and heterocycloalkylalkyl radicals, or in the case of a disubstituted aminoalkyl radical, said substituents along with the nitrogen atom to which they are attached, form a heterocycloalkyl or a heteroaryl radical; and $R^4$ represents radicals as defined by $R^3$.

A more preferred family of compounds within Formula IV consists of compounds wherein R represents an arylalkanoyl, heteroaroyl, aryloxyalkanoyl, aryloxycarbonyl, alkanoyl, aminocarbonyl, mono-substituted aminoalkanoyl, or disubstituted aminoalkanoyl, or mono-or dialkylaminocarbonyl radical;

R' represents hydrogen and radicals as defined for $R^3$ or R and R' together with the nitrogen to which they are attached represent a heterocycloalkyl or heteroaryl radical;

$R^1$, $R^{1'}$ and $R^{1'''}$ independently represent hydrogen and alkyl radicals having from 1 to about 4 carbon atoms, alkenyl, alkynyl, aralkyl radicals, and radicals represented by the formula —$CH_2C(O)R''$ or —$C(O)R''$ wherein R'' represents $R^{38}$, —$NR^{38}R^{39}$ and $OR^{38}$ wherein $R^{38}$ and $R^{39}$ independently represent hydrogen and alkyl radicals having from 1 to about 4 carbon atoms;

$R^2$ represents alkyl, cycloalkylalkyl and aralkyl radicals, which radicals are optionally substituted with halogen radicals and radicals represented by the formula —$OR^9$ and —$SR^9$ wherein $R^9$ represents hydrogen and alkyl radicals; and $R^3$ and $R^4$ independently represent alkyl, alkenyl, alkoxyalkyl, cycloalkyl, cycloalkylalkyl, heterocycloalkyl, heterocycloalkylalkyl, aryl, aralkyl, heteroaryl and heteroaralkyl radicals.

Of highest interest are compounds of Formula IV wherein:

R represents an arylalkanoyl, aryloxycarbonyl, aryloxyalkanoyl, alkanoyl, aminocarbonyl, mono-substituted aminoalkanoyl, or disubstituted aminoalkanoyl, or mono-or dialkylaminocarbonyl radical;

R' represents hydrogen and radicals as defined for $R^3$ or R and R' together with the nitrogen to which they are attached represent a heterocycloalkyl or heteroaryl radical;

$R^1$, $R^{1'}$ and $R^{1'''}$ independently represent hydrogen, methyl, ethyl, benzyl, phenylpropyl and propargyl radicals;

$R^2$ represents $CH_3SCH_2CH_2$—, iso-butyl, n-butyl, benzyl, 4-fluorobenzyl, 2-naphthylmethyl and cyclohexylmethyl radicals;

$R^3$ represents alkyl, cyclohexyl, isobutyl, isoamyl and n-butyl radicals; and $R^4$ represents methyl, phenyl and substituted phenyl radicals wherein the substituents are selected from halo, alkoxy, amino and nitro substituents.

As utilized herein, the term "alkyl", alone or in combination, means a straight-chain or branched-chain alkyl radical containing from 1 to about 10 carbon atoms, preferably from 1 to about 8 carbon atoms, more preferably 1–5 carbon atoms. Examples of such radicals include methyl, ethyl, n-propyl, isopropyl, n-butyl, isobutyl, sec-butyl, tert-butyl, pentyl, iso-amyl, hexyl, octyl and the like. The term "alkenyl", alone or in combination, means a straight-chain or branched-chain hydrocarbon radial having one or more double bonds and containing from 2 to about 18 carbon atoms, preferably from 2 to about 8 carbon atoms, more preferably from 2 to about 5 carbon atoms. Examples of suitable alkenyl radicals include ethenyl, propenyl, alkyl, 1,4-butadienyl and the like. The term "alkynyl", alone or in combination, means a straight-chain or branched chain hydrocarbon radical having one or more triple bonds and containing from 2 to about 10 carbon atoms, more preferably from 2 to about 5 carbon atoms. Examples of alkynyl radicals include ethynyl, propynyl, (propargyl), butynyl and the like. The term "alkoxy", alone or in combination, means an alkyl ether radical wherein the term alkyl is as defined above. Examples of suitable alkyl ether radicals include methoxy, ethoxy, n-propoxy, isopropoxy, n-butoxy, iso-butoxy, sec-butoxy, tert-butoxy and the like. The term "cycloalkyl", alone or in combination, means a saturated or partially saturated monocyclic, bicyclic or tricyclic alkyl radical wherein each cyclic moiety contains from about 3 to about 8 carbon atoms, more preferably from about 3 to about 6 carbon atoms, and is cyclic. Examples of such cycloalkyl radicals include cyclopropyl, cyclobutyl, cyclopentyl, cyclohexyl and the like. The term "cycloalkylalkyl" means an alkyl radical as defined above which is substituted by a cycloalkyl radical as defined above. The term "aryl", alone or in combination, means a phenyl or naphthyl radical which optionally carries one or more substituents selected from alkyl, alkoxy, halogen, hydroxy, amino, nitro, cyano, haloalkyl, carboxy, alkoxycarbonyl, cycloalkyl, heterocycloalkyl, amido, mono and dialkyl substituted amino, mono and dialkyl substituted amido and the like, such as phenyl, p-tolyl, 4-methoxyphenyl, 4-(tert-butoxy) phenyl, 4-fluorophenyl, 4-chlorophenyl, 4-hydroxyphenyl, 1-naphthyl, 2-naphthyl, and the like. The terms "aralkyl" and "aralkoxy", alone or in combination, means an alkyl or alkoxy radical as defined above in which at least one hydrogen atom is replaced by an aryl radical as defined above, such as benzyl, benzyloxy, 2-phenylethyl, dibenzylmethyl, hydroxyphenylmethyl, methylphenylmethyl, and the like. The term "aralkoxy carbonyl", alone or in combination, means a radical of the formula —C(O)—O—aralkyl in which the term "aralkyl" has the significance given above. Examples of an aralkoxycarbonyl radical are benzyloxycarbonyl and methylphenylmethoxycarbonyl. The term "aryloxyl" means a radical of the formula aryl—O— in which the term aryl has the significance given above. The term "alkanoyl", alone or in combination, means an acyl radical derived from an alkanecarboxylic acid, examples of which include acetyl, propionyl, butyryl, valeryl, 4-methylvaleryl, and the like. The term "cycloalkylcarbony", means an acyl group derived from a monocyclic or bridged cycloalkanecarboxylic acid such as cyclopropanecarbonyl, cyclohexanecarbonyl, adamantanecarbonyl, and the like, or from a benz-fused monocyclic cycloalkanecarboxylic acid which is optionally substituted by, for example, alkanoylamino, such as 1,2,3, 4-tetrahydro-2-naphthoyl, 2-acetamido-1,2,3,4-tetrahydro-2-naphthoyl. The term "aralkanoyl" means an acyl radical derived from an aryl-substituted alkanecarboxylic acid such as phenylacetyl, 3-phenylpropionyl (hydrocinnamoyl), 4-phenylbutyryl, (2-naphthyl)acetyl, 4-chlorohydrocinnamoyl, 4-aminohydrocinnamoyl,4-methoxyhydrocinnamoyl, and the like. The term "aroyl" means an acyl radical derived from an aromatic carboxylic acid. Examples of such radicals include aromatic carboxylic acids, an optionally substituted benzoic or naphthoic acid such as benzoyl, 4-chlorobenzoyl, 4-carboxybenzoyl, 4-(benzyloxycarbonyl)benzoyl, 1-naphthoyl, 2-naphthoyl, 6-carboxy-2 naphthoyl, 6-(benzyloxycarbonyl)-2-naphthoyl, 3-benzyloxy-2-naphthoyl, 3-hydroxy-2-naphthoyl, 3-(benzyloxyformamido)-2-naphthoyl, and the like. The terms "heterocyclyl" and "heterocycloalkyl" alone or in combination, mean a saturated or partially unsaturated monocyclic, bicyclic or tricyclic heterocycle which contains one or more heteroatoms selected from nitrogen, oxygen and sulphur, which is optionally substituted on one or more carbon atoms by halogen, alkyl, alkoxy, hydroxy, oxo, aryl, aralkyl and the like, and/or on a secondary nitrogen atom (i.e., —NH—) by hydroxy, alkyl, aralkoxycarbonyl, alkanoyl, phenyl or phenylalkyl and/or on a tertiary nitrogen atom (i.e.=N—) by oxido and which is attached via a carbon atom. Heterocycloalkyl and heterocyclyl also includes benz-fused monocyclic cycloalkyl groups having at least one heteroatom. Heterocycloalkyl and heterocyclyl in addition to sulfur and nitrogen also includes sulfones, sulfoxides and N-oxides of tertiary nitrogen containing heterocycloalkyl groups. The term "heteroaryl", alone or in combination, means an aromatic monocyclic, bicyclic, or tricyclic hetero-cycle which contains the heteroatoms and is optionally substituted as defined above with respect to the definitions of aryl and heterocycloalkyl. Examples of such heterocy-cloalkyl and heteroaryl groups are pyrrolidinyl, piperidinyl, piperazinyl, morpholinyl, thiamorpholinyl, pyrrolyl, imidazolyl (e.g., imidazol 4-yl, 1-benzyloxycarbonylimidazol-4-yl, etc.), pyrazolyl, pyridyl, (e.g., 2-(1-piperidinyl)pyridyl and 2-(4-benzyl piperazin-1-yl-1-pyridinyl), pyrazinyl, pyrimidinyl, furyl, thienyl, triazolyl, oxazolyl, thiazolyl, indolyl (e.g., 2-indolyl, etc.), quinolinyl, (e.g., 2-quinolinyl, 3-quinolinyl, 1-oxido-2-quinolinyl, etc.), isoquinolinyl (e.g., 1-isoquinolinyl, 3-isoquinolinyl, etc.), tetrahydroquinolinyl (e.g., 1,2,3,4-tetrahydro-2-quinolyl, etc.), 1,2,3,4-tetrahydroisoquinolinyl (e.g., 1,2,3,4-tetrahydro-1-oxo-isoquinolinyl, etc.), quinoxalinyl, β-carbolinyl, 2-benzofurancarbonyl, 1-, 2-,4- or 5-benzimidazolyl, and the like. The term "cycloalkylalkoxycarbonyl" means an acyl group derived from a cycloalkylalkoxycarboxylic acid of the formula cycloalkylalkyl—O—COOH wherein cycloalkylalkyl has the significance given above. The term "aryloxyalkanoyl" means an acyl radical of the formula aryl—O—alkanoyl wherein aryl and alkanoyl have the significance given above. The term "heterocycloalkoxycarbonyll, means an acyl group derived from heterocyclyl—O—COOH wherein heterocyclyl is as defined above. The term "heterocycloalkylalkanoyl" is an acyl radical derived from a heterocycloalkyl-substituted alkane carboxylic acid wherein heterocycloalkyl has the significance given above. The term "heterocycloalkyla-lkoxycarbonyl" means an acyl radical derived from a heterocycloalkyl-substituted alkane—O—COOH wherein heterocyclyl has the significance given above. The term "heteroaryloxycarbonyl" means an acyl radical derived from a carboxylic acid represented by heteroaryl—O—COOH wherein heteroaryl has the significance given above. The term "aminocarbonyl" alone or in combination, means an amino-substituted carbonyl (carbamoyl) group wherein the amino group can be a primary; secondary or tertiary amino group containing substituents selected from alkyl, aryl, aralkyl, cycloalkyl, cycloalkylalkyl radicals and the like. The term "aminoalkanoyl" means an acyl group derived from an amino-substituted alkanecarboxylic acid wherein the amino group can be a primary, secondary or tertiary amino group containing substituents selected from alkyl, aryl, aralkyl, cycloalkyl, cycloalkylalkyl radicals and the like. The term "halogen" means fluorine, chlorine, bromine or iodine. The term "haloalkyll" means an alkyl radical having the significance as defined above wherein one or more hydrogens are replaced with a halogen. Examples of such haloalkyl radicals include chloromethyl, 1-bromoethyl, fluoromethyl, difluoromethyl, trifluoromethyl, 1,1,1-trifluoroethyl and the like. The term "leaving group" generally refers to groups readily displaceable by a nucleophile, such as an amine, a thiol or an alcohol nucleophile. Such leaving groups are well known in the art. Examples of such leaving groups include, but are not limited to, N-hydroxysuccinimide, N-hydroxybenzotriazole, halides, triflates, tosylates and the like. Preferred leaving groups are indicated herein where appropriate. The term "amino acid side chain" means the side chain group, including the stereochemistry of the carbon to which it is attached, attached to the naturally occurring amino acid which distinguishes the amino acid from glycine. For example, the amino acid side chain of alanine is methyl, of histidine is imidazolylmethyl and phenylalanine is benzyl, and the attachment of such side chains to the compound of this invention retain the naturally occurring stereochemistry of the carbon to which it is attached. The following example illustrates the definitions:

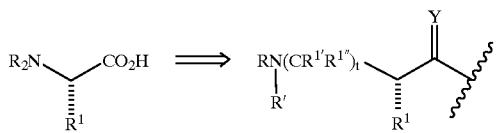

Procedures for preparing the compounds of Formula I are set forth below. It should be noted that the general procedure is shown as it relates to preparation of compounds having the specified stereochemistry, for example, wherein the absolute stereochemistry about the hydroxyl group is designated as (R). However, such procedures are generally applicable to those compounds of opposite configuration, e.g., where the stereochemistry about the hydroxyl group is (S). In addition, the compounds having the (R) stereochemistry can be utilized to produce those having the (S) stereochemistry. For example, a compound having the (R) stereochemistry can be inverted to the (S) stereochemistry using well-known methods.

Preparation of Compounds of Formula I

The compounds of the present invention represented by Formula I above can be prepared utilizing the following general procedure. This procedure is schematically shown in the following Schemes I and II:

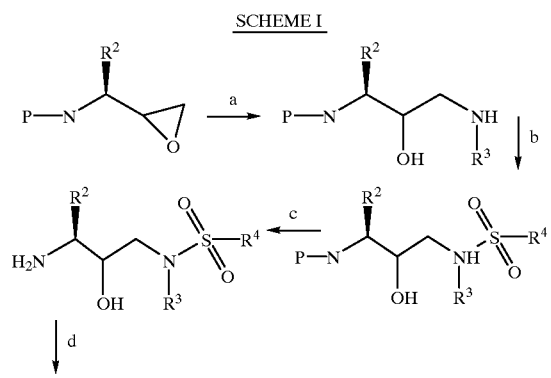

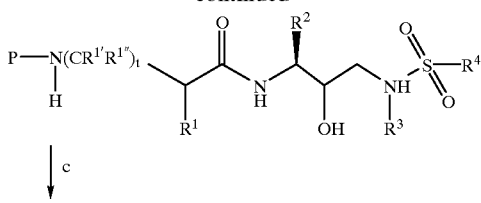

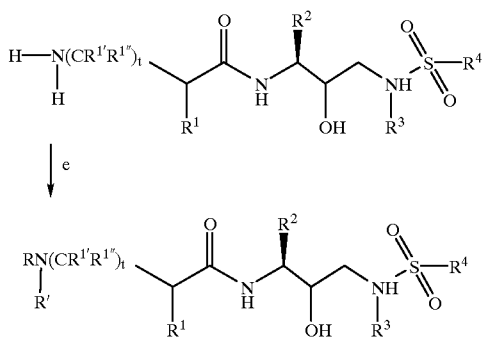

a) amine b) sulfonyl chloride R⁴SO₂Cl (or anhydride)+acid scavenger c) deprotection d) coupling e) coupling.

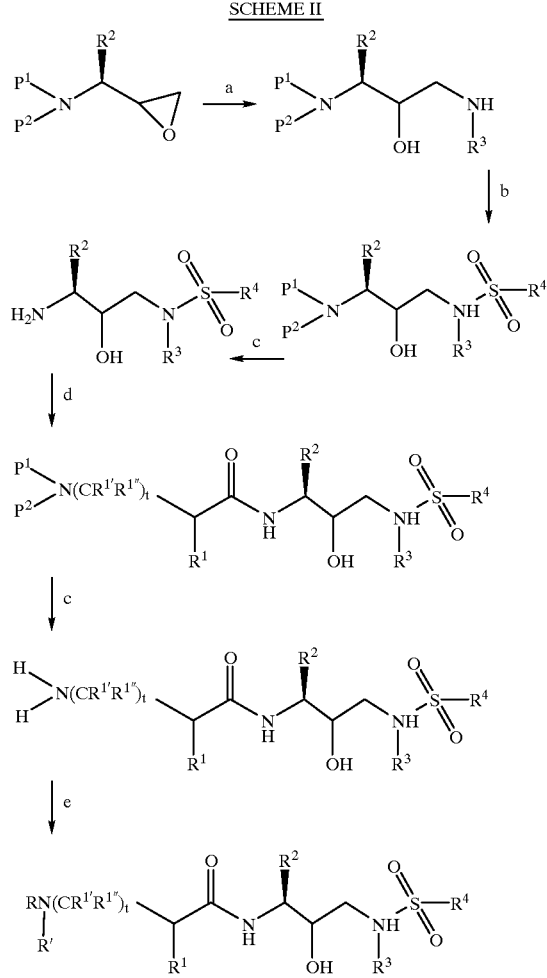

a) amine b) sulfonyl chloride R⁴SO₂Cl (or anhydride)+acid scavenger c) deprotection d) coupling e) coupling.

An N-protected chloroketone derivative of an amino acid having the formula:

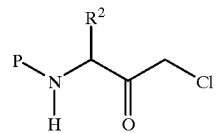

wherein P represents an amino protecting group, and $R^2$ is as defined above, is reduced to the corresponding alcohol utilizing an appropriate reducing agent. Suitable amino protecting groups are well known in the art and include carbobenzoxy, t-butoxycarbonyl, and the like. A preferred amino protecting group is carbobenzoxy. A preferred N-protected chloroketone is N-benzyloxycarbonyl-L-phenylalanine chloromethyl ketone. A preferred reducing agent is sodium borohydride. The reduction reaction is conducted at a temperature of from −10° C. to about 25° C., preferably at about 0° C., in a suitable solvent system such as, for example, tetrahydrofuran, and the like. The N-protected chloroketones are commercially available, e.g., such as from Bachem, Inc., Torrance, Calif. Alternatively, the chloroketones can be prepared by the procedure set forth in S. J. Fittkau, *J. Prakt. Chem.*, 315, 1037 (1973), and subsequently N-protected utilizing procedures which are well known in the art.

The halo alcohol can be utilized directly, as described below, or, preferably, is then reacted, preferably at room temperature, with a suitable base in a suitable solvent system to produce an N-protected amino epoxide of the formula:

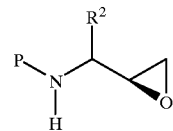

wherein P and $R^2$ are as defined above. Suitable solvent systems for preparing the amino epoxide include ethanol, methanol, isopropanol, tetrahydrofuran, dioxane, and the like including mixtures thereof. Suitable bases for producing the epoxide from the reduced chloroketone include potassium hydroxide, sodium hydroxide, potassium t-butoxide, DBU and the like. A preferred base is potassium hydroxide.

Alternatively, a protected amino epoxide can be prepared, such as in co-owned and co-pending PCT patent application Ser. No. PCT/US93/04804 which is incorporated herein by reference, starting with an L-amino acid which is reacted with a suitable amino-protecting group in a suitable solvent to produce an amino-protected L-amino acid ester of the formula:

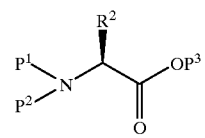

wherein $P^3$ represents carboxyl-protecting group, e.g., methyl, ethyl, benzyl, tertiary-butyl and the like; $R^2$ is as defined above; and $P^1$ and $P^2$ independently are selected from amine protecting groups, including but not limited to, arylalkyl, substituted arylalkyl, cycloalkenylalkyl and substituted cycloalkenylalkyl, allyl, substituted allyl, acyl, alkoxycarbonyl, aralkoxycarbonyl and silyl. Examples of arylalkyl include, but are not limited to benzyl, ortho-methylbenzyl, trityl and benzhydryl, which can be optionally substituted with halogen, alkyl of $C_1$–$C_8$, alkoxy, hydroxy, nitro, alkylene, amino, alkylamino, acylamino and acyl, or their salts, such as phosphonium and ammonium salts. Examples of aryl groups include phenyl, naphthalenyl, indanyl, anthracenyl, durenyl, 9-(9-phenylfluorenyl) and phenanthrenyl, cycloalkenylalkyl or substituted cycloalkylenylalkyl radicals containing cycloalkyls of $C_6$–$C_{10}$. Suitable acyl groups include carbobenzoxy, t-butoxycarbonyl, iso-butoxycarbonyl, benzoyl, substituted benzoyl, butyryl, acetyl, tri-fluoroacetyl, tri-chloroacetyl, phthaloyl and the like.

Additionally, the $P^1$ and/or $p^2$ protecting groups can form a heterocyclic ring with the nitrogen to which they are attached, for example, 1,2-bis(methylene)benzene, phthalimidyl, succinimidyl, maleimidyl and the like and where these heterocyclic groups can further include adjoining aryl and cycloalkyl rings. In addition, the heterocyclic groups can be mono-, di- or tri-substituted, e.g., nitrophthalimidyl. The term silyl refers to a silicon atom optionally substituted by one or more alkyl, aryl and aralkyl groups.

Suitable silyl protecting groups include, but are not limited to, trimethylsilyl, triethylsilyl, tri-isopropylsilyl, tert-butyldimethylsilyl, dimethylphenylsilyl, 1,2-bis(dimethylsilyl)benzene, 1,2-bis(dimethylsilyl)ethane and diphenylmethylsilyl. Silylation of the amine functions to provide mono- or bis-disilylamine can provide derivatives of the aminoalcohol, amino acid, amino acid esters and amino acid amide. In the case of amino acids, amino acid esters and amino acid amides, reduction of the carbonyl function provides the required mono- or bis-silyl aminoalcohol. Silylation of the aminoalcohol can lead to the N,N,O—tri-silyl derivative. Removal of the silyl function from the silyl ether function is readily accomplished by treatment with, for example, a metal hydroxide or ammonium flouride reagent, either as a discrete reaction step or in situ during the preparation of the amino aldehyde reagent. Suitable silylating agents are, for example, trimethylsilyl chloride, tert-butydimethylsilyl chloride, phenyldimethylsilyl chlorie, diphenylmethylsilyl chloride or their combination products with imidazole or DMF. Methods for silylation of amines and removal of silyl protecting groups are well known to those skilled in the art. Methods of preparation of these amine derivatives from corresponding amino acids, amino acid amides or amino acid esters are also well known to those skilled in the art of organic chemistry including amino acid/amino acid ester or aminoalcohol chemistry.

Preferably $P^1$ and $P^2$ are independently selected from aralkyl and substituted aralkyl. More preferably, each of $P^1$ and $P^2$ is benzyl.

The amino-protected L-amino acid ester is then reduced, to the corresponding alcohol. For example, the amino-protected L-amino acid ester can be reduced with diisobutylaluminum hydride at –78° C. in a suitable solvent such as toluene. Preferred reducing agents include lithium aluminium hydride, lithium borohydride, sodium borohydride, borane, lithium tri-ter-butoxyaluminum hydride, borane/THF complex. Most preferably, the reducing agent is diisobutylaluminum hydride (DiBAL-H) in toluene. The resulting alcohol is then converted, for example, by way of a Swern oxidation, to the corresponding aldehyde of the formula:

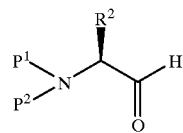

wherein $p^1$, $P^2$ and $R^2$ are as defined above. Thus, a dichloromethane solution of the alcohol is added to a cooled (–75 to –68° C.) solution of oxalyl chloride in dichloromethane and DMSO in dichloromethane and stirred for 35 minutes.

Acceptable oxidizing reagents include, for example, sulfur trioxide-pyridine complex and DMSO, oxalyl chloride and DMSO, acetyl chloride or anhydride and DMSO, trifluoroacetyl chloride or anhydride and DMSO, methanesulfonyl chloride and DMSO or tetrahydrothiaphene-S-oxide, toluenesulfonyl bromide and DMSO, trifluoromethanesulfonyl anhydride (triflic anhydride) and DMSO, phosphorus pentachloride and DMSO, dimethylphosphoryl chloride and DMSO and isobutylchloroformate and DMSO. The oxidation conditions reported by Reetz et al [*Angew Chem.*, 99, p. 1186, (1987)], *Angew Chem. Int. Ed. Engl.*, 26, p. 1141, 1987) employed oxalyl chloride and DMSO at –78° C.

The preferred oxidation method described in this invention is sulfur trioxide pyridine complex, triethylamine and DMSO at room temperature. This system provides excellent yields of the desired chiral protected amino aldehyde usable without the need for purification i.e., the need to purify kilograms of intermediates by chromatography is eliminated and large scale operations are made less hazardous. Reaction at room temperature also eliminated the need for the use of low temperature reactor which makes the process more suitable for commercial production.

The reaction may be carried out under and inert atmosphere such as nitrogen or argon, or normal or dry air, under atmospheric pressure or in a sealed reaction vessel under positive pressure. Preferred is a nitrogen atmosphere. Alternative amine bases include, for example, tri-butyl amine, tri-isopropyl amine, N-methylpiperidine, N-methyl morpholine, azabicyclononane, diisopropylethylamine, 2,2,6,6-tetramethylpiperidine, N,N-dimethylaminopyridine, or mixtures of these bases. Triethylamine is a preferred base. Alternatives to pure DMSO as solvent include mixtures of DMSO with non-protic or halogenated solvents such as tetrahydrofuran, ethyl acetate, toluene, xylene, dichloromethane, ethylene dichloride and the like. Dipolar aprotic co-solvents include acetonitrile, dimethylformamide, dimethylacetamide, acetamide, tetramethyl urea and its cyclic analog, N-methylpyrrolidone, sulfolane and the like. Rather than N,N-dibenzylphenylalaninol as the aldehyde precursor, the phenylalaninol derivatives discussed above can be used to provide the corresponding N-monosubstituted [either $P^1$ or $P^2$=H] or N,N-disubstituted aldehyde.

In addition, hydride reduction of an amide or ester derivative of the corresponding alkyl, benzyl or cycloalkenyl nitrogen protected phenylalanine, substituted phenylalanine or cycloalkyl analog of phenyalanine derivative can be carried out to provide the aldehydes. Hydride transfer is an additional method of aldehyde synthesis under conditions where aldehyde condensations are avoided, cf, Oppenauer Oxidation.

The aldehydes of this process can also be prepared by methods of reducing protected phenylalanine and phenylalanine analogs or their amide or ester derivatives by, e.g., sodium amalgam with HCl in ethanol or lithium or sodium or potassium or calcium in ammonia. The reaction temperature may be from about −20° C. to about 45° C., and preferably from abut 5° C. to about 25° C. Two additional methods of obtaining the nitrogen protected aldehyde include oxidation of the corresponding alcohol with bleach in the presence of a catalytic amount of 2,2,6,6-tetramethyl-1-pyridyloxy free radical. In a second method, oxidation of the alcohol to the aldehyde is accomplished by a catalytic amount of tetrapropylammonium perruthenate in the presence of N-methylmorpholine-N-oxide.

Alternatively, an acid chloride derivative of a protected phenylalanine or phenylalanine derivative as disclosed above can be reduced with hydrogen and a catalyst such as Pd on barium carbonate or barium sulphate, with or without an additional catalyst moderating agent such as sulfur or a thiol (Rosenmund Reduction).

The aldehyde resulting from the Swern oxidation is then reacted with a halomethyllithium reagent, which reagent is generated in situ by reacting an alkyllithium or arylithium compound with a dihalomethane represented by the formula $X^1CH_2X^2$ wherein $X^1$ and $X^2$ independently represent I, Br or Cl. For example, a solution of the aldehyde and chloroiodomethane in THF is cooled to −78° C. and a solution of n-butyllithium in hexane is added. The resulting product is a mixture of diastereomers of the corresponding amino-protected epoxides of the formulas:

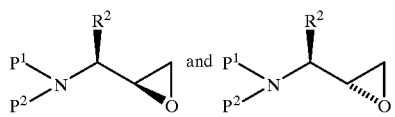

The diastereomers can be separated e.g., by chromatography, or, alternatively, once reacted in subsequent steps the diastereomeric products can be separated. For compounds having the (S) stereochemistry, a D-amino acid can be utilized in place of the L-amino acid.

The addition of chloromethylithium or bromomethylithium to a chiral amino aldehyde is highly diastereoselective. Preferably, the chloromethyllithium or bromomethylithium is generated in-situ from the reaction of the dihalomethane and n-butyllithium. Acceptable methyleneating halomethanes include chloroiodomethane, bromochloromethane, dibromomethane, diiodomethane, bromofluoromethane and the like. The sulfonate ester of the addition product of, for example, hydrogen bromide to formaldehyde is also a methyleneating agent. Tetrahydrofuran is the preferred solvent, however alternative solvents such as toluene, dimethoxyethane, ethylene dichloride, methylene chloride can be used as pure solvents or as a mixture. Dipolar aprotic solvents such as acetonitrile, DMF, N-methylpyrrolidone are useful as solvents or as part of a solvent mixture. The reaction can be carried out under an inert atmosphere such as nitrogen or argon. For n-butyl lithium can be substituted other organometalic reagents reagents such as methyllithium, tert-butyl lithium, sec-butyl lithium, phenyllithium, phenyl sodium and the like. The reaction can be carried out at temperatures of between about −80° C. to 0° C. but preferably between about −80° C. to −20° C. The most preferred reaction temperatures are between −40° C. to −15° C. Reagents can be added singly but multiple additions are preferred in certain conditions. The preferred pressure of the reaction is atmospheric however a positive pressure is valuable under certain conditions such as a high humidity environment.

Alternative methods of conversion to the epoxides of this invention include substitution of other charged methylenation precurser species followed by their treatment with base to form the analogous anion. Examples of these species include trimethylsulfoxonium tosylate or triflate, tetramethylammonium halide, methyldiphenylsulfoxonium halide wherein halide is chloride, bromide or iodide.

The conversion of the aldehydes of this invention into their epoxide derivative can also be carried out in multiple steps. For example, the addition of the anion of thioanisole prepared from, for example, a butyl or aryl lithium reagent, to the protected aminoaldehyde, oxidation of the resulting protected aminosulfide alcohol with well known oxidizing agents such as hydrogen peroxide, tert-butyl hypochlorite, bleach or sodium periodate to give a sulfoxide. Alkylation of the sulfoxide with, for example, methyl iodide or bromide, methyl tosylate, methyl mesylate, methyl triflate, ethyl bromide, isopropyl bromide, benzyl chloride or the like, in the presence of an organic or inorganic base Alternatively, the protected aminosulfide alcohol can be alkylated with, for example, the alkylating agents above, to provide a sulfonium salts that are subsequently converted into the subject epoxides with tert-amine or mineral bases.

The desired epoxides formed, using most preferred conditions, diastereoselectively in ratio amounts of at least about an 85:15 ratio (S:R). The product can be purified by chromatography to give the diastereomerically and enantiomerically pure product but it is more conveniently used directly without purification to prepare retroviral protease inhibitors. The foregoing process is applicable to mixtures of optical isomers as well as resolved compounds. If a particular optical isomer is desired, it can be selected by the choice of starting material, e.g., L-phenylalanine, D-phenylalanine, L-phenylalaninol, D-phenylalaninol, D-hexahydrophenylalaninol and the like, or resolution can occur at intermediate or final steps. Chiral auxiliaries such as one or two equivilants of camphor sulfonic acid, citric acid, camphoric acid, 2-methoxyphenylacetic acid and the like can be used to form salts, esters or amides of the compounds of this invention. These compounds or derivatives can be crystallized or separated chromatographically using either a chiral or achiral column as is well known to those skilled in the art.

The amino epoxide is then reacted, in a suitable solvent system, with an equal amount, or preferably an excess of, a desired amine of the formula:

wherein $R^3$ is hydrogen or is as defined above. The reaction can be conducted over a wide range of temperatures, e.g., from about 10° C. to about 100° C., but is preferably, but not necessarily, conducted at a temperature at which the solvent begins to reflux. Suitable solvent systems include protic, non-protic and dipolar aprotic organic solvents such as, for example, those wherein the solvent is an alcohol, such as methanol, ethanol, isopropanol, and the like; ethers such as tetrahydrofuran, dioxane and the like, and toluene, N,N-dimethylformamide, dimethyl sulfoxide, and mixtures thereof. A preferred solvent is isopropanol. Exemplary amines corresponding to the formula $R^3NH_2$ include benzyl amine, isobutylamine, n-butyl amine, isopentyl amine, isoamylamine, cyclohexanemethyl amine, naphthylene methyl amine and the like. The resulting product is a 3-(N-protected amino)-3-($R^2$)-1-($NHR^3$)-propan-2-ol derivative (hereinafter referred to as an amino alcohol) can be represented by the formulas:

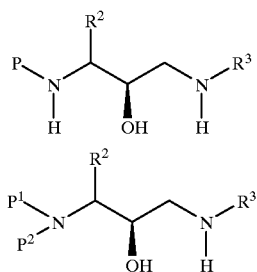

wherein P, P¹, P², R² and R³ are as described above. Alternatively, a haloalcohol can be utilized in place of the amino epoxide.

The amino alcohol defined above is then reacted in a suitable solvent with a sulfonyl chloride ($R^4SO_2Cl$) or sulfonyl anhydride in the presence of an acid scavenger. Suitable solvents in which the reaction can be conducted include methylene chloride, tetrahydrofuran. Suitable acid scavengers include triethylamine, pyridine. Preferred sulfonyl chlorides are methanesulfonyl chloride and benzenesulfonyl chloride. The resulting sulfonamide derivative can be represented, depending on the epoxide utilized by the formulas

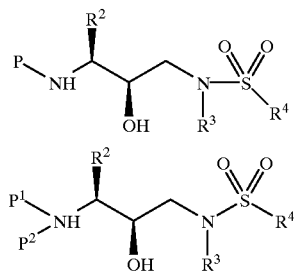

wherein P, P¹, P²; R², R³ and R⁴ are as defined above. These intermediates are useful for preparing inhibitor compounds of the present invention and are also active inhibitors of retroviral proteases.

The sulfonyl halides of the formula $R^4SO_2X$ can be prepared by the reaction of a suitable Grignard or alkyl lithium reagent with sulfuryl chloride, or sulfur dioxide followed by oxidation with a halogen, preferably chlorine. Also, thiols may be oxidized to sulfonyl chlorides using chlorine in the presence of water under carefully controlled conditions. Additionally, sulfonic acids may be converted to sulfonyl halides using reagents such as $PCl_5$, and also to anhydrides using suitable dehydrating reagents. The sulfonic acids may in turn be prepared using procedures well known in the art. Such sulfonic acids are also commercially available. In place of the sulfonyl halides, sulfinyl halides ($R^4SOX$) or sulfenyl halides ($R^4SX$) can be utilized to prepare compounds wherein the —$SO_2$— moiety is replaced by an —SO— or —S— moiety, respectively.

Following preparation of the sulfonamide derivative, the amino protecting group P or P¹ and P² amino protecting groups are removed under conditions which will not affect the remaining portion of the molecule. These methods are well known in the art and include acid hydrolysis, hydrogenolysis and the like. A preferred method involves removal of the protecting group, e.g., removal of a carbobenzoxy group, by hydrogenolysis utilizing palladium on carbon in a suitable solvent system such as an alcohol, acetic acid, and the like or mixtures thereof. Where the protecting group is a t-butoxycarbonyl group, it can be removed utilizing an inorganic or organic acid, e.g., HCl or trifluoroacetic acid, in a suitable solvent system, e.g., dioxane or methylene chloride. The resulting product is the amine salt derivative. Following neutralization of the salt, the amine is then reacted with an amino acid or corresponding derivative thereof represented by the formula (PN[CR¹'R¹'']$_t$ CH(R¹) COOH) wherein t, R¹, R¹' and R¹'' are as defined above, to produce the antiviral compounds of the present invention having the formula:

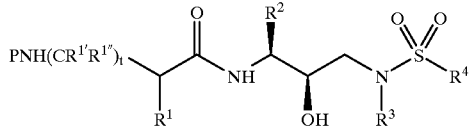

wherein t, P, R¹, R¹', R¹'', R², R³ and R⁴ are as defined above. Preferred protecting groups in this instance are a benzyloxycarbonyl group or a t-butoxycarbonyl group. Where t is O and R¹ is alkyl, alkenyl, alkynyl, cycloalkyl, —$CH_2SO_2NH_2$, —$CH_2CO_2CH_3$, —$CO_2CH_3$, —$CONH_2$, —$CH_2C(O)NHCH_3$, —$C(CH_3)_2(SH)$, —$C(CH_3)_2(SCH_3)$, —$C(CH_3)_2[S(O)CH_3]$, —$C(CH_3)_2[S(O_2)CH_3]$, or an amino acid side chain, such materials are well known and many are commercially available from Sigma-Aldrich.

Where the amine is reacted with a derivative of an amino acid, e.g., when t=1, so that the amino acid is a β-amino acid, such β-amino acids can be prepared according to the procedure set forth in a co-owned, copending patent application, U.S. Ser. No. 07/853,561 or the following procedures Various methods have been proposed for the preparation of chiral β-amino acids. See, for example, *Chemistry and Biochemistry of Amino Acids*, Vol. 4, Chapter 5, pp. 250–57, B. Weinstein, Ed., Dekker, N.Y. (1975). Furukawa et al, *Chem. Pharm. Bull.*, 25, 1319 (1977), disclose asymmetric synthesis of β-amino acids by addition of chiral amines to carbon-carbon double bonds having nitrile or ester groups in the α-position. However, optical purities of the β-amino acids thus produced range from 2 to 19%. Furukawa et al also report that optically active β-amino acids have been produced with optical purities ranging from 2 to 28% by reacting chiral Schiff bases with Reformsky reagent. Terentev et al, Dohl. Ahad. Nauh SSR, 163,674 (1965) disclose synthesis of β-aminobutyric acids involving addition of chiral amines to crotonic acid with optical purities ranging from 7–9%.

Brown et al, *Tetrahedron Lett.*, Vol. 28, No. 19, pp 2179–2182 (1987), disclose a method of preparing optically active disubstituted β-amino acids which involves asymmetric catalytic hydrogenation of N-substituted α-(aminoalkyl) acrylates. In order to verify the stereochemistry of the product, Curtius rearrangement was effected on the monomethyl ester of optically enriched RR-anti-2,3-dimethylsuccinic acid and trapping of the incipient isocyanate derivative with tertiary alcohol, namely, t-butyl alcohol, to give the corresponding R-enriched β-amino acid.

Ninomita et al, *Tetrahedron Lett.*, Vol. 30, 2152–2157 (1975) studied the Curtius rearrangement utilizing benzoic acid, diphenylphosphoryl azide and triethylamine followed by treatment with various alcohols and found that t-butyl alcohol gives yields superior to benzyl alcohol, ethanol and phenol.

Utilization of a primary or secondary alcohol to trap an isocyanate derivative of a chiral mono-substituted succinate, and, in particular, in a Curtius rearrangement of a chiral mono-substituted succinate, to produce chiral β-amino acids significantly increases the overall yield. The resulting carbamate-protected β-amino esters are then saponified to produce the corresponding carbamate-protected β-amino acids which are then deprotected to produce β-amino acids possessing the same absolute configuration as naturally-occurring (L)-amino acids.

The overall reaction sequence can be shown as follows:

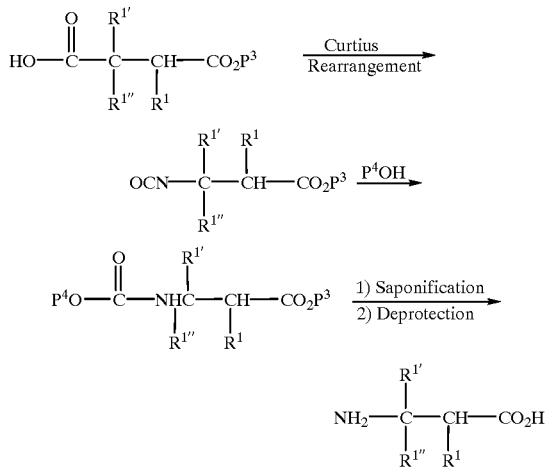

wherein $R^1$, $R^{1'}$, $R^{1''}$, and $P^3$ are as defined above and $P^4OH$ are preferably represents radicals derived from primary and secondary alcohols.

This process can also be used in the asymetric synthesis of β-amino acids represented by the formula:

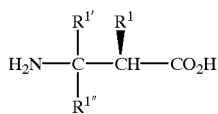

wherein $R^1$, $R^{1'}$ and $R^{1''}$ are as defined above. Such compounds are formed by Curtius rearrangement of 2(R)-substituted succinates represented by the formula

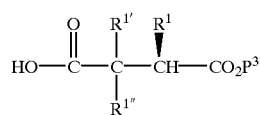

wherein $R^1$, $R^{1'}$, $R^{1''}$ and $P^3$ are as defined above, to afford the isocyanate derivative:

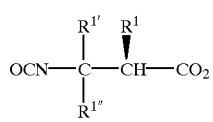

Using 2(S)-substituted succinates, 2(S)-substituted β-amino acids can also be prepared stereospecifically.

Curtius rearrangement involves pyrolysis of acyol azides

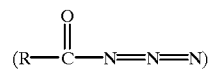

to yield isocyanates (R—N=C=O) which can be subsequently hydrolyzed to give amines. See March, Advanced Organic Chemistry, p. 1005, 2nd ed (1977). As a general rule, Curtius rearrangement is a concerted reaction and therefore proceeds with retention of configuration of the starting materials. Determination of specific reaction conditions for effecting Curtius rearrangements of various succinates is within the skill of one in the art familiar with such reactions. In the method of the present invention, Curtius rearrangement to afford the desired isocyante is preferably effected by treating a 2-substituted succinate with one equivalent of diphenoxyphosphoryl azide $(PhO)_2PON_3$ and triethylamine to form the acyl azide followed by heating in an inert solvent, such as in warm toluene, preferably at about 80° C. for about three hours, to afford the isocyante derivative.

Suitable primary and secondary alcohols include those represented by the formula $P^4OH$ where $P^4$ representes substituted and unsubstituted alkyl, cycloalkyl, aralkyl and aryl radicals, as well as suitable equivalents such as, for example, silyl radicals. Preferably, the primary and secondary alcohols are those wherein $P^4$ represents substituted and unsubstituted, straight chain as well as branched chain, alkyl radicals having from 1 to about 12 carbon atoms, substituted and unsubstituted cycloalkyl radicals having from 4 to about 7 carbon atoms, and substituted and unsubstituted aryl, alkaryl and aralkyl radicals. Examples of such suitable alcohols include benzyl alcohol, isopropyl alcohol, 4-methoxybenzyl alcohol, 2-trimethylsilylethanol, fluorenyl methanol and benzhydrol. Preferred alcohols are benzyl alcohol and 4-methoxybenzyl alcohol. Other primary and secondary alcohols suitable for use in the practice of the present invention will be readily apparent to those skilled in the art.

The ester derivative is then saponified by any one of numerous well-known procedures, such as by treatment with aqueous lithium hydroxide/THF (tetrahydrofuran), preferably for three hours at 0° C. The resultant product is the corresponding carbamate-protected β-amino acids. These are subsequently deprotected by any one of several well-known procedures, such as by acid catalyzed hydrolysis or by hydrogenolysis, to produce the corresponding deprotected β-amino acids. Alternatively, the carbamate-protected β-amino acid can be coupled to the amine

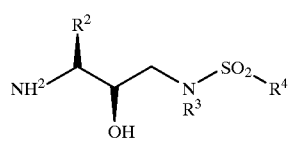

followed by deprotection and incorporation of R and R'.

The N-protecting group can be subsequently removed, if desired, utilizing the procedures described above, and then reacted with a carboxylate represented by the formula:

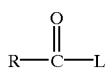

wherein R is as defined above and L is an appropriate leaving group such as a halide. Preferably, where $R^1$ is a side chain of a naturally occurring α-amino acid, R is a 2-quinoline carbonyl group derived from N-hydroxysuccinimide-2-quinoline carboxylate, i.e., L is hydroxy succinimide. A solution of the free amine (or amine acetate salt) and about 1.0 equivalent of the carboxylate are mixed in an appropriate solvent system and optionally treated with up to five equivalents of a base such as, for example, N-methylmorpholine, at about room temperature. Appropriate solvent systems include tetrahydrofuran, methylene chloride or N,N-dimethylformamide, and the like, including mixtures thereof.

Alternatively, the protected amino alcohol from the epoxide opening can be further protected at the newly introduced amino group with a protecting group P' which is not removed when the first protecting P is removed. One skilled in the art can choose appropriate combinations of P and P'. One suitable choice is when P is Cbz and P' is Boc. The resulting compound represented by the formula:

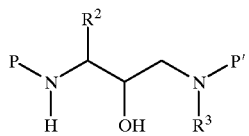

can be carried through the remainder of the synthesis to provide a compound of the formula:

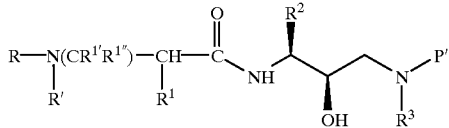

and the new protecting group P' is selectively removed, and following deprotection, the resulting amine reacted to form the sulfonamide derivative as described above. This selective deprotection and conversion to the sulfonamide can be accomplished at either the end of the synthesis or at any appropriate intermediate step if desired.

The thiocarbonyl compounds of this invention are really prepared by methods well known to those skilled in the art, for example, by treatment of a carbonyl compound with Lawesson's reagent (2,4-bis(4-methoxyphenyl)-1,3-dithia-2,4-diphosphetane-2,4-disulfide) which is an article of commerce. Phosphoruspentasulfide may also be used or one can treat an amine of this invention with a pre-formed thiocarbonyl reagent such as thiocarbonylchlorid in the presence of base.

In place of the sulfonyl halides, sulfinyl halides (RSOCl) and sulfenyl halides (RSCl) can be utilized to prepare compounds wherein the —$SO_2$— moiey is replaced by —SO— or —S—, respectively.

It is contemplated that for preparing compounds of the Formulas having $R^6$, the compounds can be prepared following the procedure set forth above and, prior to coupling the sulfonamide derivative or analog thereof, e.g. coupling to the amino acid $PNH(CH_2)_tCH(R^1)COOH$, carried through a procedure referred to in the art as reductive amination. Thus, a sodium cyanoborohydride and an appropriate aldehyde or ketone can be reacted with the sulfonamide derivative compound or appropriate analog at room temperature in order to reductively aminate any of the compounds of Formulas I–IV. It is also contemplated that where $R^3$ of the amino alcohol intermediate is hydrogen, the inhibitor compounds of the present invention wherein $R^3$ is alkyl, or other substituents wherein the α-C contains at least one hydrogen, can be prepared through reductive amination of the final product of the reaction between the amino alcohol and the amine or at any other stage of the synthesis for preparing the inhibitor compounds.

Contemplated equivalents of the general formulas set forth above for the antiviral compounds and derivatives as well as the intermediates are compounds otherwise corresponding thereto and having the same general properties, such as tautomers thereof as well as compounds, wherein one or more of the various R groups are simple variations of the substituents as defined therein, e.g., wherein R is a higher alkyl group than that indicated. In addition, where a substituent is designated as, or can be, a hydrogen, the exact chemical nature of a substituent which is other than hydrogen at that position, e.g., a hydrocarbyl radical or a halogen, hydroxy, amino and the like functional group, is not critical so long as it does not adversely affect the overall activity and/or synthesis procedure.

The chemical reactions described above are generally disclosed in terms of their broadest application to the preparation of the compounds of this invention. Occasionally, the reactions may not be applicable as described to each compound included within the disclosed scope. The compounds for which this occurs will be readily recognized by those skilled in the art. In all such cases, either the reactions can be successfully performed by conventional modifications known to those skilled in the art, e.g., by appropriate protection of interfering groups, by changing to alternative conventional reagents, by routine modification of reaction conditions, and the like, or other reactions disclosed herein or otherwise conventional, will be applicable to the preparation of the corresponding compounds of this invention. In all preparative methods, all starting materials are known or readily preparable from known starting materials.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

All reagents were used as received without purification. All proton and carbon NMR spectra were obtained on either a Varian VXR-300 or VXR-400 nuclear magnetic resonance spectrometer.

The following Examples 1 through 9 illustrate preparation of intermediates. These intermediates are useful in preparing the inhibitor compounds of the present invention as illustrated in Examples 10–16. In addition, the intermediates of Examples 2–6 are also retroviral protease inhibitors and inhibit, in particular, HIV protease.

EXAMPLE 1A

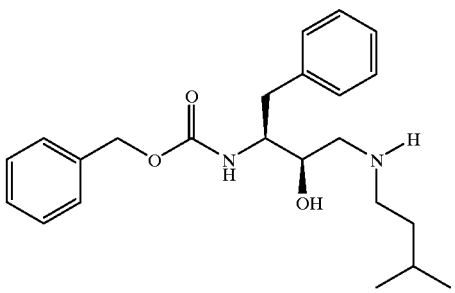

Preparation of N[3(S)-benzyloxycarbonylamino-2 (R)-hydroxy-4-phenylbutyl]-N-isoamylamine Part A:

To a solution of 75.0 g (0.226 mol) of N-benzyloxycarbonyl-L-phenylalanine chloromethyl ketone in a mixture of 807 mL of methanol and 807 mL of tetrahydrofuran at -2° C., was added 13.17 g (0.348 mol, 1.54 equiv.) of solid sodium borohydride over one hundred minutes. The solvents were removed under reduced pressure at 40° C. and the residue dissolved in ethyl acetate (approx. 1 L). The solution was washed sequentially with 1M potassium hydrogen sulfate, saturated sodium bicarbonate and then saturated sodium chloride solutions. After drying over anhydrous magnesium sulfate and filtering, the solution was removed under reduced pressure. To the resulting oil was added hexane (approx. 1 L) and the mixture warmed to 60° C. with swirling. After cooling to room temperature, the solids were collected and washed with 2 L of hexane. The resulting solid was recrystallized from hot ethyl acetate and hexane to afford 32.3 g (43% yield) of N-benzyloxycarbonyl-3(S)-amino-1-chloro-4-phenyl-2(S)-butanol, mp 150–151° C. and M+Li$^+$=340.

Part B:

To a solution of 6.52 g (0.116 mol, 1.2 equiv.) of potassium hydroxide in 968 mL of absolute ethanol at room temperature, was added 32.3 g (0.097 mol) of N-CBZ-3(S)-amino-1-chloro-4-phenyl-2(S)-butanol. After stirring for fifteen minutes, the solvent was removed under reduced pressure and the solids dissolved in methylene chloride. After washing with water, drying over magnesium sulfate, filtering and stripping, one obtains 27.9 g of a white solid. Recrystallization from hot ethyl acetate and hexane afforded 22.3 g (77% yield) of N-benzyloxycarbonyl-3(S)-amino-1,2(S)-epoxy-4-phenylbutane, mp 102–103° C. and MH$^+$298.

Part C:

A solution of N-benzyloxycarbonyl 3(S)-amino-1,2-(S)-epoxy-4-phenylbutane (1.00 g, 3.36 mmol) and isoamylamine (4.90 g, 67.2 mmol, 20 equiv.) in 10 mL of isopropyl alcohol was heated to reflux for 1.5 hours. The solution was cooled to room temperature, concentrated in vacuo and then poured into 100 mL of stirring hexane whereupon the product crystallized from solution. The product was isolated by filtration and air dried to give 1.18 g, 95% of N=[[3(S)-phenylmethylcarbamoyl)amino-2(R)-hydroxy-4-phenylbutyl]N-[(3-methylbutyl)]amine mp 108.0–109.5° C., MH$^+$ m/z=371.

EXAMPLE 1B

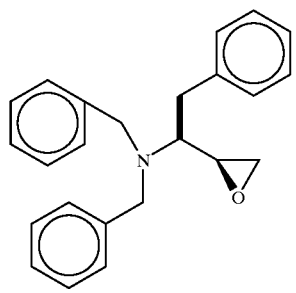

Preparation of N,N-dibenzyl-3(S)-amino-1,2-(S)-epoxy-4-phenylbutane

Step A:

A solution of L-phenylalanine (50.0 g, 0.302 mol), sodium hydroxide (24.2 g, 0.605 mol) and potassium carbonate (83.6 g, 0.605 mol) in water (500 ml) was heated to 97° C. Benzyl bromide (108.5 ml, 0.912 mol) was then slowly added (addition time ~25 min). The mixture was then stirred at 97° C. for 30 minutes. The solution was cooled to room temperature and extracted with toluene (2×250 ml). The combined organic layers were then washed with water, brine, dried over magnesium sulfate, filtered and concentrated to give an oil product. The crude product was then used in the next step without purification.

Step B:

The crude benzylated product of the above step was dissolved in toluene (750 ml) and cooled to -55° C. A 1.5M solution of DIBAL-H in toluene (443.9 ml, 0.666 mol) was then added at a rate to maintain the temperature between -55° to -50° C. (addition time ~1 hour). The mixture was stirred for 20 minutes at -55° C. The reaction was quenched at -55° C. by the slow addition of methanol (37 ml). The cold solution was then poured into cold (5° C.) 1.5 N HCl solution (1.8 L). The precipitated solid (approx. 138 g) was filtered off and washed with toluene. The solid material was suspended in a mixture of toluene (400 ml) and water (100 ml) The mixture was cooled to 5° C., treated with 2.5 N NaOH (186 ml) and then stirred at room temperature until the solid was dissolved. The toluene layer was separated from the aqueous phase and washed with water and brine, dried over magnesium sulfate, filtered and concentrated to a volume of 75 ml (89 g). Ethyl acetate (25 ml) and hexane (25 ml) were then added to the residue upon which the alcohol product began to crystallize. After 30 min., an additional 50 ml hexane was added to promote further crystallization. The solid was filtered off and washed with 50 ml hexane to give approximately 35 g of material. A second crop of material could be isolated by refiltering the mother liquor The solids were combined and recrystallized from ethyl acetate (20 ml) and hexane (30 ml) to give, in 2 crops, approximately 40 g (40% from L-phenylalanine) of analytically pure alcohol product. The mother liquors were combined and concentrated (34 g). The residue was treated with ethyl acetate and hexane which provided an additional 7 g (~7% yield) of slightly impure solid product. Further optimization in the recovery from the mother liquor is probable.

Alternatively, the alcohol was prepared from L-phenylalaninol. L-phenylalaninol (176.6 g, 1.168 mol) was added to a stirred solution of potassium carbonate (484.6 g, 3.506 mol) in 710 mL of water. The mixture was heated to 65° C. under a nitrogen atmosphere. A solution of benzyl bromide (400 g, 2.339 mol) in 3A ethanol (305 mL)

was added at a rate that maintained the temperature between 60–68° C. The biphasic solution was stirred at 65° C. for 55 min and then allowed to cool to 10° C. with vigorous stirring. The oily product solidified into small granules. The product was diluted with 2.0 L of tap water and stirred for 5 minutes to dissolve the inorganic by products. The product was isolated by filtration under reduced pressure and washed with water until the pH is 7. The crude product obtained was air dried overnite to give a semi-dry solid (407 g) which was recrystallized from 1.1 L of ethyl acetate/heptane (1:10 by volume). The product was isolated by filtration (at −8° C.), washed with 1.6 L of cold (−10° C.) ethyl acetate/heptane (1:10 by volume) and air-dried to give 339 g (88% yield) of βS-2-[Bis(phenylmethyl)amino]benzene-propanol, mp 71.5–73.0° C. More product can be obtained from the mother liquor if necessary. The other analytical characterization was identical to compound prepared as described above.

Step C:

A solution of oxalyl chloride (8.4 ml, 0.096 mol) in dichloromethane (240 ml) was cooled to −74° C. A solution of DMSO (12.0 ml, 0.155 mol) in dichloromethane (50 ml) was then slowly added at a rate to maintain the temperature at −74° C. (addition time ~1.25 hr). The mixture was stirred for 5 min. followed by addition of a solution of the alcohol (0.074 mol) in 100 ml of dichloromethane (addition time −20 min., temp. −75° C. to −68° C.). The solution was stirred at −78° C. for 35 minutes. Triethylamine (41.2 ml, 0.295 mol) was then added over 10 min. (temp. −78° to −68° C.) upon which the ammonium salt precipitated. The cold mixture was stirred for 30 min. and then water (225 ml) was added. The dichloromethane layer was separated from the aqueous phase and washed with water, brine, dried over magnesium sulfate, filtered and concentrated. The residue was diluted with ethyl acetate and hexane and then filtered to further remove the ammonium salt. The filtrate was concentrated to give the desired aldehyde product. The aldehyde was carried on to the next step without purification.

Temperatures higher than −70° C. have been reported in the literature for the Swern oxidation. Other Swern modifications and alternatives to the Swern oxidations are also possible.

Alternatively, the aldehyde was prepared as follows. (200 g, 0.604 mol) was dissolved in triethylamine (300 mL, 2.15 mol). The mixture was cooled to 12° C. and a solution of sulfur trioxide/pyridine complex (380 g, 2.39 mol) in DMSO (1.6 L) was added at a rate to maintain the temperature between 8–17° C. (addition time ~1.0 h). The solution was stirred at ambient temperature under a nitrogen atmosphere for 1.5 hour at which time the reaction was complete by TLC analysis (33% ethyl acetate/hexane, silica gel). The reaction mixture was cooled with ice water and quenced with 1.6 L of cold water (10–15° C.) over 45 minutes. The resultant solution was extracted with ethyl acetate (2.0 L), washed with 5% citric acid (2.0 L), and brine (2.2 L), dried over $MgSO_4$ (280 g) and filtered. The solvent was removed on a rotary evaporator at 35–40° C. and then dried under vaccuum to give 198.8 g of αS-[Bis-(phenylmethyl)amino]-benzenepropanaldehyde as a pale yellow oil (99.9%). The crude product obtained was pure enough to be used directly in the next step without purification. The analytical data of the compound were consistent with the published literature. $[\alpha]_D 25=-92.9°$ (c 1.87, $CH_2Cl_2$); $^1H$ NMR (400 MHz, $CDCl_3$) ∂, 2.94 and 3.15 (ABX-System, 2H, $J_{AB}$=13.9 Hz, $J_{AX}$=7.3 Hz and $J_{BX}$=6.2 Hz), 3.56 (t, 1H, 7.1 Hz), 3.69 and 3.82 (AB-System, 4H, $J_{AB}$=13.7 Hz), 7.25 (m, 15 H) and 9.72 (s, 1H); HRMS calcd for (M+1) $C_{23}H_{24}NO$ 330.450, found: 330.1836. Anal. Calcd. for $C_{23}H_{23}ON$: C, 83.86; H, 7.04; N, 4.25. Found: C, 83.64; H, 7.42; N, 4.19. HPLC on chiral stationary phase:(S,S) Pirkle-Whelk—O 1 column (250×4.6 mm I.D.), mobile phase: hexane/isopropanol (99.5:0.5, v/v), flow-rate: 1.5 ml/min, detection with UV detector at 210 nm. Retention time of the desired S-isomer: 8.75 min., retention time of the R-enanatiomer 10.62 min.

Step D:

A solution of αS-[BiS(phenylmethyl)amino] benzene-propanaldehyde (191.7 g, 0.58 mol) and chloroiodomethane (56.4 mL, 0.77 mol) in tetrahydrofuran (1.8 L) was cooled to −30 to −35° C. (colder temperature such as −70° C. also worked well but warmer temperatures are more readily achieved in large scale operations) in a stainless steel reactor under a nitrogen atmosphere. A solution of n-butyllithium in hexane (1.6 M, 365 mL, 0.58 mol) was then added at a rate that maintained the temperature below −25° C. After addition the mixture was stirred at −30 to −35° C. for 10 minutes. More additions of reagents were carried out in the following manner: (1) additional chloroiodomethane (17 mL) was added, followed by n-butyllithium (110 mL) at <−25° C. After addition the mixture was stirred at −30 to −35° C. for 10 minutes. This was repeated once. (2) Additional chloroiodomethane (8.5 mL, 0.11 mol) was added, followed by n-butyllithium (55 mL, 0.088 mol) at <−25° C. After addition, the mixture was stirred at −30 to −35° C. for 10 minutes. This was repeated 5 times. (3) Additional chloroiodomethane (8.5 mL, 0.11 mol) was added, followed by n-butyllithium (37 mL, 0.059 mol) at <−25° C. After addition, the mixture was stirred at −30 to −35° C. for 10 minutes. This was repeated once. The external cooling was stopped and the mixture warmed to ambient temp. over 4 to 16 hours when TLC (silica gel, 20% ethyl acetate/hexane) indicated that the reaction was completed. The reaction mixture was cooled to 10° C. and quenched with 1452 g of 16% ammonium chloride solution (prepared by dissolving 232 g of ammonium chloride in 1220 mL of water), keeping the temperature below 23° C. The mixture was stirred for 10 minutes and the organic and aqueous layers were separated. The aqueous phase was extracted with ethyl acetate (2×500 mL). The ethyl acetate layer was combined with the tetrahydrofuran layer. The combined solution was dried over magnesium sulfate (220 g), filtered and concentrated on a rotary evaporator at 65° C. The brown oil residue was dried at 70° C. in vacuo (0.8 bar) for 1 h to give 222.8 g of crude material. (The crude product weight was >100%. Due to the relative instability of the product on silica gel, the crude product is usually used directly in the next step without purification). The diastereomeric ratio of the crude mixture was determined by proton NMR: (2S)/(2R): 86:14. The minor and major epoxide diastereomers were characterized in this mixture by tlc analysis (silica gel, 10% ethyl acetate/hexane), Rf=0.29 & 0.32, respectively. An analytical sample of each of the diastereomers was obtained by purification on silica-gel chromatography (3% ethyl acetate/hexane) and characterized as follows:

N,N,αS-Tris(phenylmethyl)-2S-oxiranemethanamine; $^1H$ NMR (400 MHz, $CDCl_3$) ∂ 2.49 and 2.51 (AB-System, 1H, $J_{AB}$=2.82), 2.76 and 2.77 (AB-System, 1H, $J_{AB}$=4.03), 2.83 (m, 2H), 2.99 & 3.03 (AB-System, 1H, $J_{AB}$=10.1 Hz), 3.15 (m, 1H), 3.73 & 3.84 (AB-System, 4H, $J_{AB}$=14.00), 7.21 (m, 15H); $^{13}C$ NMR (400 MHz,$CDCl_3$) ∂ 139.55, 129.45, 128.42, 128.14, 128.09, 126.84, 125.97, 60.32, 54.23, 52.13, 45,99, 33.76; HRMS calcd for $C_{24}H_{26}NO$ (M+1) 344.477, found 344.2003.

N,N,αS-Tris(phenylmethyl)-2R-oxiranemethanamine; $^1H$ NMR (300 MHz, $CDCl_3$) ∂ 2.20 (m, 1H), 2.59 (m, 1H), 2.75 (m, 2H), 2.97 (m, 1H), 3.14 (m, 1H), 3.85 (AB-System, 4H), 7.25 (m, 15H).HPLC on chiral stationary phase: Pirkle-Whelk—O 1 column (250×4.6 mm I.D.), mobile phase: hexane/isopropanol (99.5:0.5, v/v), flow-rate: 1.5 ml/min, detection with UV detector at 210 nm. Retention time of (8): 9.38 min., retention time of enanatiomer of (4): 13.75 min.

Alternatively, a solution of the crude aldehyde 0.074 mol and chloroiodomethane (7.0 ml, 0.096 mol) in tetrahydrofuran (285 ml) was cooled to −78° C., under a nitrogen atmosphere. A 1.6 M solution of n-butyllithium in hexane (25 ml, 0.040 mol) was then added at a rate to maintain the temperature at −75° C. (addition time −15 min.). After the first addition, additional chloroiodomethane (1.6 ml, 0.022 mol) was added again, followed by n-butyllithium (23 ml, 0.037 mol), keeping the temperature at −75° C. The mixture was stirred for 15 min. Each of the reagents, chloroiodomethane (0.70 ml, 0.010 mol) and n-butyllithium (5 ml, 0.008 mol) were added 4 more times over 45 min. at −75° C. The cooling bath was then removed and the solution warmed to 22° C. over 1.5 hr. The mixture was poured into 300 ml of saturated aq. ammonium chloride solution. The tetrahydrofuran layer was separated. The aqueous phase was extracted with ethyl acetate (1×300 ml). The combined organic layers were washed with brine, dried over magnesium sulfate, filtered and concentrated to give a brown oil (27.4 g). The product could be used in the next step without purification. The desired diastereomer can be purified by recrystallization at a subsequent step. The product could also be purified by chromatography.

Alternatively, a solution of αS-[Bis(phenylmethyl)amino]benzene-propanaldehyde (178.84 g, 0.54 mol) and bromochloromethane (46 mL, 0.71 mol) in tetrahydrofuran (1.8 L) was cooled to −30 to −35° C. (colder temperature such as −70° C. also worked well but warmer temperatures are more readily achieved in large scale operations) in a stainless steel reactor under a nitrogen atmosphere. A solution of n-butyllithium in hexane (1.6 M, 340 mL, 0.54 mol) was then added at a rate that maintained the temperature below −25° C. After addition the mixture was stirred at −30 to −35° C. for 10 minutes. More additions of reagents were carried out in the following manner: (1) additional bromochloromethane (14 mL) was added, followed by n-butyllithium (102 mL) at <−25° C. After addition the mixture was stirred at −30 to −35° C. for 10 minutes. This was repeated once. (2) Additional bromochloromethane (7 mL, 0.11 mol) was added, followed by n-butyllithium (51 mL, 0.082 mol) at <−25° C. After addition the mixture was stirred at −30 to −35° C. for 10 minutes. This was repeated 5 times. (3) Additional bromochloromethane (7 mL, 0.11 mol) was added, followed by n-butyllithium (51 mL, 0.082 mol) at <−25° C. After addition the mixture was stirred at −30 to −35° C. for 10 minutes. This was repeated once. The external cooling was stopped and the mixture warmed to ambient temp. over 4 to 16 hours when TLC (silica gel, 20% ethyl acetate/hexane) indicated that the reaction was completed The reaction mixture was cooled to 10° C. and quenched with 1452 g of 16% ammonium chloride solution (prepared by dissolving 232 g of ammonium chloride in 1220 mL of water), keeping the temperature below 23° C. The mixture was stirred for 10 minutes and the organic and aqueous layers were separated. The aqueous phase was extracted with ethyl acetate (2×500 mL). The ethyl acetate layer was combined with the tetrahydrofuran layer. The combined solution was dried over magnesium sulfate (220 g), filtered and concentrated on a rotary evaporator at 65° C. The brown oil residue was dried at 70° C. in vacuo (0.8 bar) for 1 h to give 222.8 g of crude material.

EXAMPLE 2

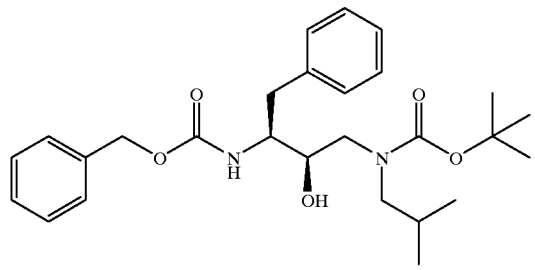

Preparation of N-[[3S-(phenylmethylcarbamoyl)aminol-2R-hydroxy-4-phenyl]-1-[(2-methylpropyl)amino-2-(1,1-dimethylethoxyl)carbonyl]butane To a solution of 7.51 g (20.3 mmol) of N-[[3S-(phenylmethylcarbamoyl)amino]-2R-hydroxy-4-phenylbutyl]-N-(2-methylpropyl)]amine in 67 mL of anhydrous tetrahydrofuran was added 2.25 g (22.3 mmol) of triethylamine. After cooling to 0° C., 4.4 g (20.3 mmol) of di-tert-butyldicarbonate was added and stirring continued at room temperature for 21 hours. The volatiles were removed in vacuo, ethyl acetate added, then washed with 5% citric acid, saturated sodium bicarbonate, brine, dried over magnesium sulfate, filtered and concentrated to afford 9.6 g of crude product. Chromatography on silica gel using 30% ethyl acetate/hexane afforded 8.2 g of pure N-[[3S-(phenylmethylcarbamoyl)amino]-2R-hydroxy-4-phenyl]-1-[(2-methylpropyl)amino-2-(1,1-dimethylethoxyl)carbonyl]butane, mass spectum m/e=477 (M+Li).

EXAMPLE 3A

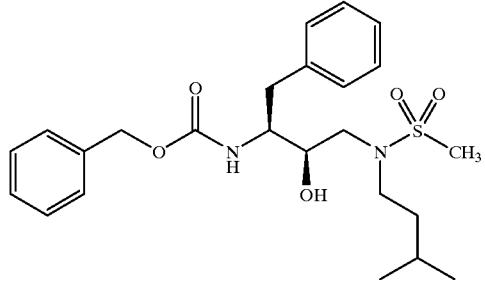

Preparation of phenylmethyl [2R-hydroxy-3-[(3-methylbutyl) (methylsulfonyl)amino]-1S-(phenylmethyl)-propyl]carbamate To a solution of N[3(S)-benzyloxycarbonylamino-2(R)-hydroxy-4-phenylbutyl] N-isoamylamine (2.0 gm, 5.2 mmol) and triethylamine (723 uL, 5.5 mmol) in dichloromethane (20 mL) was added dropwise methanesulfonyl chloride (400 uL, 5.2 mmol). The reaction mixture was stirred for 2 hours at room temperature, then the dichloromethane solution was concentrated to ca. 5 mL and applied to a silica gel column (100 gm). The column was eluted with chloroform containing 1% ethanol and 1% methanol. The phenylmethyl [2R-hydroxy-3-[(3-methylbutyl) (methylsulfonyl)amino]-1S-(phenylmethyl)propyl]carbamate was obtained as a white solid Anal. Calcd for $C_{24}H_{34}N_2O_5S$: C, 62.31; H, 7.41; N, 6.06. Found: C, 62.17; H, 7.55; N, 5.97.

EXAMPLE 3B

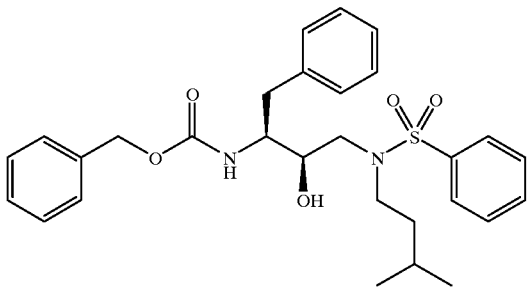

Preparation of phenylmethyl [2R-hydroxy-3-[(3-methylbutyl) (phenylsulfonyl)amino]-1S-(phenylmethyl)-propyl]carbamate From the reaction of N[3(S)-benzyloxycarbonylamino-2(R)-hydroxy-4-phenylbutyl] N-isoamylamine (1.47 gm, 3.8 mmol), triethylamine (528 uL, 3.8 mmol) and benzenesulfonyl chloride (483 uL, 3.8 mmol) one obtains phenylmethyl [2R-hydroxy-3-[(3-methylbutyl) (phenylsulfonyl)amino]-1S-(phenylmethyl)propyl]-carbamate. Column chromotography on silica gel eluting with chloroform containing 1% ethanol afforded the pure product. Anal. Calcd for $C_{29}H_{36}N_2O_5S$: C, 66.39; H, 6.92; N, 5.34. Found: C, 66.37; H, 6.93; N, 5.26.

EXAMPLE 4

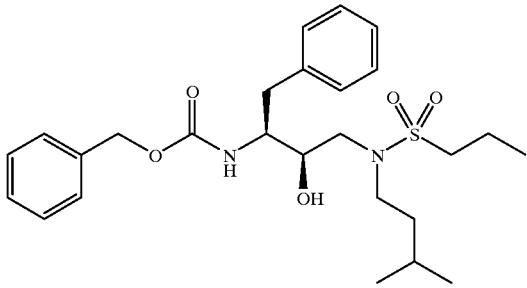

Preparation of Phenylmethyl [2R-hydroxy-3-[(3-methylbutyl) (n-propanesulfonyl)amino]-1S-(phenylmethyl)-propyl]carbamate To a solution of N[3(S)-benzyloxycarbonylamino-2(R)-hydroxy-4-phenylbutyl] N-isoamylamine (192 mg, 0.5 mmol) and triethylamine (139 uL, 1.0 mmol) in dichloromethane (10 mL) was added dropwise trimethylsilyl chloride (63 uL, 0.5 mmol). The reaction was allowed to stir for 1 hour at room temperature, cooled to 0° C. with an ice bath and then n-propanesulfonyl chloride (56 uL, 0.5 mmol) was added dropwise. The reaction mixture was stirred for 1.5 hours at room temperature, then diluted with ethyl acetate (50 mL) and washed sequentially with 1N HCl, water, saturated sodium bicarbonate solution, and saturated sodium chloride solution (25 mL each). The organic solution was dried over magnesium sulfate, filtered and concentrated to an oil. The oil was stirred with methanol (10 mL) for 16 hours, concentrated and the residue chromatographed on silica gel (50 gm) eluting with 10% ethyl acetate in hexane (450 mL), then with 1:1 ethyl acetate/hexane. The phenylmethyl [2R-hydroxy-3-[(3-methylbutyl) (n-propanesulfonyl)amino]-1S-(phenylmethyl)propyl] carbamate was recrystallized from ethyl ether/hexane to afford a white solid Anal. Calcd. for $C_{26}H_{38}N_2O_5S$: C, 63.64; H, 7.81; N, 5.71. Found: C, 63.09; H, 7.74; N, 5.64.

EXAMPLE 5

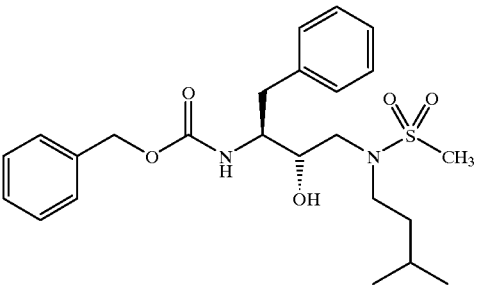

The procedure described in Example 2 was used to prepare phenylmethyl [2S-hydroxy-3-[(3-methylbutyl) (methylsulfonyl)amino]-1S-(phenylmethyl)propyl] carbamate.

To a solution of N[3(S)-benzyloxycarbonylamino-2(S)-hydroxy-4-phenylbutyl] N-isoamylamine (192 mg, 0.5 mmol) and triethylamine (139 uL, 0.55 mmol) in dichloromethane (8 mL) was added dropwise methanesulfonyl chloride (39 uL, 0.55 mmol). The reaction mixture was stirred for 16 hours at room temperature, then the dichloromethane solution was applied to a silica gel column (50 gm). The column was eluted with dichloromethane containing 2.5% methanol. The phenylmethyl [2S-hydroxy-3-[(3-methylbutyl) (methylsulfonyl)amino]-1S-(phenylmethyl) propyl]carbamate was obtained as a white solid Anal. Calcd. for $C_{24}H_{34}N_2O_5S$ ◊ 0.2 $H_2O$: C, 61.83; H, 7.44; N, 6.01. Found: C, 61.62; H, 7.40; N, 5.99.

EXAMPLE 6

Following the procedures of the previous Examples 1–5, the intermediate compounds set forth in Tables 1A and 1B were prepared.

TABLE 1A

| Entry | R³ | R⁴ |
|---|---|---|
| 1 | isoamyl | p-fluorophenyl |
| 2 | isoamyl | p-nitrophenyl |
| 3 | isoamyl | o-nitrophenyl |
| 4 | isoamyl | β-naphthyl |
| 5 | isoamyl | 2-thienyl |
| 6 | isoamyl | benzyl |
| 7 | isobutyl | p-fluorophenyl |
| 8 | p-fluorobenzyl | phenyl |
| 9 | 4-pyridylmethyl | phenyl |
| 10 | cyclohexylmethyl | phenyl |
| 11 | allyl | phenyl |
| 12 | propyl | phenyl |
| 13 | cyclopropylmethyl | phenyl |
| 14 | methyl | phenyl |
| 15 | propargyl | phenyl |
| 16 | isoamyl | p-chlorophenyl |
| 17 | isoamyl | p-methoxyphenyl |
| 18 | isoamyl | m-nitrophenyl |
| 19 | isoamyl | m-trifluoromethylphenyl |
| 20 | isoamyl | o-methoxycarbonylphenyl |
| 21 | isoamyl | p-acetamidophenyl |
| 22 | isobutyl | phenyl |
| 23 | —CH₂Ph | —Ph |
| 24 | —CH₂-C₆H₄-F | —Ph |
| 25 | —CH₂-cyclohexyl | —Ph |
| 26 | —CH₂-C₆H₄-OCH₃ | —Ph |
| 27 | —CH₂-(4-pyridyl) | —Ph |
| 28 | —CH₂-cyclopropyl | —Ph |
| 29 | —CH₂CH=CH₂ | —Ph |
| 30 | phenyl | —Ph |
| 31 | cyclohexyl | —Ph |
| 32 | —CH₂CH₂Ph | —Ph |

TABLE 1A-continued

[Structure: benzyl carbamate linked to a backbone with phenyl-CH2, NH, CH, CH(OH), CH2, N(R3)SO2R4]

| # | R3 | R4 |
|---|---|---|
| 33 | —CH₂CH₂CH₂CH₂OH | —Ph |
| 34 | —CH₂CH₂N(CH₃)₂ | —Ph |
| 35 | —CH₂CH₂—N(morpholine) | —Ph |
| 36 | —CH₃ | —Ph |
| 37 | —CH₂CH₂CH₂SCH₃ | —Ph |
| 38 | —CH₂CH₂CH₂S(O)₂CH₃ | —Ph |
| 39 | —CH₂CH₂CH(CH₃)₂ | phenyl |
| 40 | —CH₂CH₂CH(CH₃)₂ | —CH₂CH₃ |
| 41 | —CH₂CH₂CH(CH₃)₂ | —CH₃ |
| 42 | —CH₂CH₂CH(CH₃)₂ | 4-F-phenyl |
| 43 | —CH₂CH₂CH(CH₃)₂ | 4-CH₃-phenyl |
| 44 | —CH₂CH₂CH(CH₃)₂ | 2-CO₂CH₃-phenyl |
| 45 | —CH₂CH(CH₃)₂ | 4-F-phenyl |
| 46 | —CH₂CH(CH₃)₂ | 4-NHAc-phenyl |
| 47 | —CH₂CH(CH₃)₂ | 4-CH₃-phenyl |
| 48 | —CH₂CH₂CH₃ | 4-OCH₃-phenyl |
| 49 | —CH₂CH₂CH₂CH₃ | 4-OCH₃-phenyl |

TABLE 1A-continued

[Structure: benzyl carbamate with NH, CH(CH₂Ph), CH(OH), CH₂-N(R³)(SO₂R⁴)]

| Entry | R³ | R⁴ |
|---|---|---|
| 50 | —CH₂CH₂CH(CH₃)₂ | —CF₃ |
| 51 | —CH₂CH(CH₃)₂ | —CH₃ |
| 52 | —CH₂CH₂CH(CH₃)₂ | —CH₂Cl |
| 53 | —CH₂CH(CH₃)₂ | —CH₂—CH=CH—C₆H₅ (—CH₂=CH—Ph) |
| 54 | —CH₂CH(CH₃)₂ | —C₆H₄—OCH₃ (p-methoxyphenyl) |
| 55 | —CH₂CH(CH₃)₂ | —CH=CH₂ |
| 56 | —CH₂—CH(CH₃)(CH₂CH₃) | —C₆H₄—OCH₃ (p-methoxyphenyl) |

[Structure: benzyl carbamate with NH, CH(CH₂Ph), CH(OH), CH₂-N(R³)(SO₂R⁴)]

| | | | MASS MEASUREMENT | | |
|---|---|---|---|---|---|
| Entry | R³ | R⁴ | MOL FORM | CALC | FOUND |
| 1 | —CH₂CH(CH₃)₂ (isobutyl) | p-CH₃-C₆H₄— | C₂₉H₃₆N₂O₅S | 531 (M + Li) | 531 |
| 2 | | p-OCH₃-C₆H₄— | C₂₉H₃₆N₂O₆S | 541 (M + H) | 541 |
| 3 | | p-OCH₂CH₃-C₆H₄— | C₃₀H₃₆N₂O₆S | 555.2529 (M + H) | 555.2582 |
| 4 | | p-NO₂-C₆H₄— | | | |
| 5 | | p-Cl-C₆H₄— | | | |

TABLE 1A-continued

[Structure: benzyl carbamate with benzyl, OH, and N(R³)SO₂R⁴ groups]

| # | R⁴ | Formula | Calc | Found |
|---|---|---|---|---|
| 6 | 4-F-C₆H₄- | $C_{28}H_{33}N_2O_5SF$ | 529.2172 (M + H) | 521.2976 |
| 7 | 4-CF₃-C₆H₄- | | | |
| 8 | 4-SCH₃-C₆H₄- | $C_{29}H_{36}N_2O_5S_2$ | 563 (M + Li) | 563 |
| 9 | 4-SOCH₃-C₆H₄- | $C_{29}H_{36}N_2O_6S_2$ | 573 (M + H) | 573 |
| 10 | 4-SO₂CH₃-C₆H₄- | $C_{29}H_{36}N_2O_7S_2$ | 595 (M + Li) | 595 |

TABLE 1B

[Structure: RNH-CH(CH₂Ph)-CH(OH)-CH₂-N(R³)SO₂Ph]

| Entry | R | R³ |
|---|---|---|
| 1 | benzaldehyde (PhCHO) | —CH₂Ph |
| 2 | benzaldehyde (PhCHO) | —CH₂CH₂CH(CH₃)₂ |
| 3 | pyridine-2-carboxaldehyde | —CH₂CH(CH₃)₂ |
| 4 | quinoline-2-carboxaldehyde | —CH₂CH(CH₃)₂ |

TABLE 1B-continued
| Entry | R | R³ |
|---|---|---|
| 5 |  | —CH₂CH(CH₃)₂ |
| 6 | 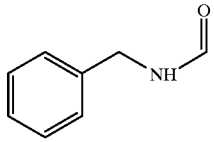 | —CH₂CH(CH₃)₂ |
| 7 | 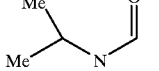 | —CH₂CH(CH₃)₂ |
TABLE 1B-continued
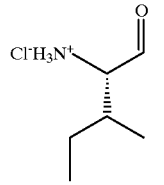
| Entry | R | R³ |
|---|---|---|
| 8 | 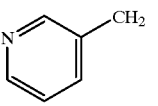 | —CH₂CH(CH₃)₂ |
| 9 | 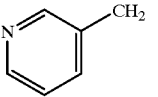 | —CH₂CH₂(CH₃)₂ |
TABLE 1C
| | | | Mass Determination | |
|---|---|---|---|---|
| X | R⁸ | FORMULA | Calc | Found |
| H |  (pyridyl-CH₂) | C₂₇H₃₃N₃O₅S | 512.2219 (M + H) | 521.2267 |
| OCH₃ |  (pyridyl-CH₂) | C₂₈H₃₅N₃O₆S | 548.2407 (M + Li) | 548.2434 |

TABLE 1C-continued
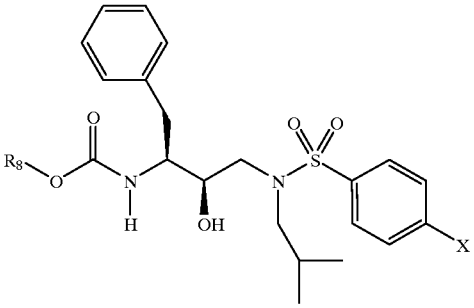
| X | R⁸ | FORMULA | Mass Determination Calc | Found |
|---|---|---|---|---|
| F | 3-pyridyl-CH₂ | $C_{27}H_{32}N_3O_5SF$ | 530 (M + H) | 530 |
| Cl | 3-pyridyl-CH₂ | $C_{27}H_{32}N_3O_5SCl$ | 546 (M + H) | 546 |
| NO₂ | 3-pyridyl-CH₂ | $C_{27}H_{32}N_4O_7S$ | 557 (M + H) | 557 |
| OH | 3-pyridyl-CH₂ | $C_{27}H_{33}N_3O_6S$ | 528 (M + H) | 528 |
| OCH₃ | 2-pyridyl-CH₂ | $C_{28}H_{35}N_3O_6S$ | 542.2325 (M + H) | 542.2362 |
| OCH₃ | 4-pyridyl-CH₂ | $C_{28}H_{35}N_3O_6S$ | 548.2407 (M + Li) | 548.2393 |
| OCH₃ | 5-pyrimidyl-CH₂ | $C_{27}H_{34}N_4O_6S$ | 543 (M + H) | 543 |
| OCH₃ | benzyl-CH₂ | $C_{29}H_{36}O_6N_2S$ | 547.2454 (M + Li) | 547.2475 |
| OCH₃ | tert-Butyl | $C_{26}H_{38}N_2O_6S$ | 513.2611 (M + Li) | 513.2593 |
| OCH₃ | pyridyl N-oxide-CH₂ | $C_{28}H_{35}N_3O_7S$ | 564 (M + Li) | 564 |

TABLE 1C-continued

| | | | Mass Determination | |
|---|---|---|---|---|
| X | R⁸ | FORMULA | Calc | Found |
| OCH₃ | (4-pyridyl-N-oxide)CH₂ | $C_{28}H_{35}N_3O_7S$ | 564 (M + Li) | 564 |

The following Examples 7–9 illustrate preparation of β-amino acid intermediates. These intermediates can be coupled to the intermediate compounds of Examples 1–6 to produce inhibitor compounds of the present invention containing β-amino acids.

EXAMPLE 7

A. Preparation of 4(4-methoxybenzyl)itaconate

A 5 L three-necked round bottomed flask equipped with constant pressure addition funnel, reflux condenser, nitrogen inlet, and mechanical stirrer was charged with itaconic anhydride (660.8 g, 5.88 mol) and toluene (2300 mL). The solution was warmed to reflux and treated with 4-methoxybenzyl alcohol (812.4 g, 5.88 mol) dropwise over a 2.6 h period. The solution was maintained at reflux for an additional 1.5 h and then the contents were poured into three 2 L erlenmeyer flasks to crystallize. The solution was allowed to cool to room temperature whereupon the desired mono-ester crystallized. The product was isolated by filtration on a Buchner funnel and air dried to give 850.2 g, 58% of material with mp 83–85° C., a second crop, 17% was isolated after cooling of the filtrate in an ice bath. ¹H NMR (CDCl₃) 300 MHz 7.32(d, J=8.7 Hz, 2H), 6.91(d, J=8.7 Hz, 2H), 6.49(s, 1H), 5.85(s, 1H), 5.12(s, 2H), 3.83(s, 3H), 3.40(s, 2H).

B. Preparation of Methyl 4(4-methoxybenzyl) itaconate

A 5 L three-necked round bottomed flask equipped with reflux condenser, nitrogen inlet, constant pressure addition funnel and mechanical stirrer was charged with 4(4-methoxybenzyl) itaconate (453.4 g, 1.81 mol) and treated with 1,5-diazabicyclo[4.3.0]non-5-ene (275.6 g, 1.81 mol), (DBN), dropwise so that the temperature did not rise above 15° C. To this stirring mixture was added a solution of methyl iodide (256.9 g, 1.81 mol) in 250 mL of toluene from the dropping funnel over a 45m period. The solution was allowed to warm to room temperature and stirred for an additional 3.25 h.

The precipitated DBN hydroiodide was removed by filtration, washed with toluene and the filtrate poured into a separatory funnel. The solution was washed with sat. aq. NaHCO₃ (2×500 mL), 0.2N HCl (1×500 mL), and brine (2×500 mL), dried over anhyd. MgSO₄, filtered, and the solvent removed in vacuo. This gave a clear colorless oil, 450.2 g, 94% whose NMR was consistent with the assigned structure. ¹H NMR (CDCl₃ 300 MHz 7.30(d, J=8.7 Hz, 2H), 6.90(d, J=8.7 Hz, 2H), 6.34(s, 1H), 5.71(s, 1H), 5.09(s, 2H), 3.82(s, 3H), 3.73(s, 3H), 3.38(s, 2H). ¹³C NMR (CDCl₃) 170.46, 166.47, 159.51, 133.55, 129.97, 128.45, 127.72, 113.77, 66.36, 55.12, 51.94, 37.64.

C. Preparation of Methyl 4(4-methoxybenzyl) 2(R)-methylsuccinate

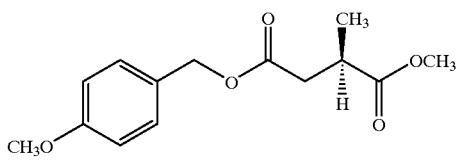

A 500 mL Fisher-Porter bottle was charged with methyl 4(4-methoxybenzyl) itaconate (71.1 g, 0.269 mol), rhodium (R,R) DIPAMP catalyst (204 mg, 0.269 mmol, 0.1 mol %) and degassed methanol (215 mL). The bottle was flushed 5 times with nitrogen and 5 times with hydrogen to a final pressure of 40 psig. The hydrogenation commenced immediately and after ca. 1h the uptake began to taper off, after 3 h the hydrogen uptake ceased and the bottle was flushed with nitrogen, opened and the contents concentrated on a rotary evaporator to give a brown oil that was taken up in boiling iso-octane (ca. 200 mL, this was repeated twice), filtered through a pad of celite and the filtrate concentrated in vacuo to give 66.6 g, 93% of a clear colorless oil, $^1$H NMR (CDC13 300 MHz 7.30(d, J=8.7 Hz, 2H), 6.91(d, J=8.7 Hz, 2H), 5.08(s, 2H), 3.82(s, 3H), 3.67(s, 3H), 2.95(ddq, J=5.7, 7.5, 8.7 Hz, 1H), 2.79(dd, J=8.1, 16.5 Hz, 1H), 2.45(dd, J=5.7, 16.5 Hz, 1H), 1.23(d, J=7.5 Hz, 3H).

D. Preparation of Methyl 2(R)-methylsuccinate

A 3 L three-necked round-bottomed flask equipped with a nitrogen inlet, mechanical stirrer, reflux condenser and constant pressure addition funnel was charged with methyl 4(4-methoxybenzyl) 2(R)-methylsuccinate (432.6 g, 1.65 mol) and toluene (1200 mL). The stirrer was started and the solution treated with trifluoroacetic acid (600 mL) from the dropping funnel over 0.25 h. The solution turned a deep purple color and the internal temperature rose to 45° C. After stirring for 2.25 h the temperature was 27° C. and the solution had acquired a pink color. The solution was concentrated on a rotary evaporator. The residue was diluted with water (2200 mL) and sat. aq. NaHCO$_3$ (1000 mL). Additional NaHCO$_3$ was added until the acid had been neutralized. The aqueous phase was extracted with ethyl acetate (2×1000 mL) to remove the by-products and the aqueous layer was acidified to pH=1.8 with conc. HCl. This solution was extracted with ethyl acetate (4×1000 mL), washed with brine, dried over anhyd. MgSO$_4$, filtered and concentrated on a rotary evaporator to give a colorless liquid 251 g, >100% that was vacuum distilled through a short path apparatus cut 1: bath temperature 120° C. @ >1 mm, bp 25–29° C.; cut 2: bath temperature 140° C. @ 0.5 mm, bp 95–108° C., 151 g, $[\alpha]_d$ @ 25° C.=+1.38° C.(c=15.475, MeOH), $[\alpha]_d$=+8.48° C. (neat); cut 3: bath temperature 140° C., bp 108° C., 36 g, $[\alpha]_d$ @ 25° C.=+1.49° C.(c=15.00, MeOH), $[\alpha]_d$=+8.98° C. (neat). Cuts 2 and 3 were combined to give 189 g, 78% of product, $^1$H NMR (CDCl$_3$) 300 MHz 11.6(brs, 1H), 3.72(s, 3H), 2.92(ddq, J=l5.7, 6.9, 8.0 Hz, 1H), 2.81(dd, J=8.0, 16.8 Hz, 1H), 2.47(dd, J=5.7, 16.8 Hz, 1H), 1.26(d, J=6.9 Hz, 3H).

E. Preparation of Methyl Itaconate

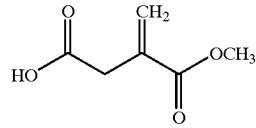

A 50 mL round bottomed flask equipped with reflux condenser, nitrogen inlet and magnetic stir bar was charged with methyl 4(4-methoxybenzyl) itaconate (4.00 g, 16 mmol), 12 mL of touluene and 6 mL of trifluoroacetic acid. The solution was kept at room temperature for 18 hours and then the volatiles were removed in vacuo. The residue was taken up in ethyl acetate and extracted three times with saturated aqueous sodium bicarbonate solution. The combined aqueous extract was acidified to pH=1 with aqueous potassium bisulfate and then extracted three times with ethyl acetate. The combined ethyl acetate solution was washed with saturated aqueous sodium chloride, dried over anhydrous magnesium sulfate, filtered, and concentrated in vacuo. The residue was then vacuum distilled to give 1.23 g, 75% of pure product, bp 85–87 @ 0.1 mm. $^1$H NMR (CDCl$_3$) 300 MHz 6.34(s, 1H), 5.73(s, 2H), 3.76(s, 3H) 3.38(s, 2H). $^{13}$C NMR (CDCl$_3$) 177.03, 166.65, 129.220, 132.99, 52.27, 37.46.

F. Curtius Rearrangement of Methyl 2(R)-methylsuccinate: Preparation of Methyl N-Moz-α-methyl β-alanine.

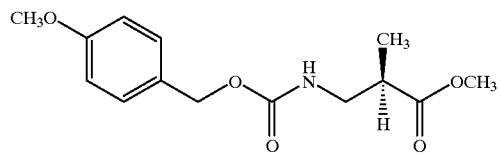

A 5 L four necked round bottomed flask equipped with a nitrogen inlet, reflux condenser, mechanical stirrer, constant pressure addition funnel, and thermometer adapter was charged with methyl 2(R)-methylsuccinate (184.1 g, 1.26 mol), triethylamine (165.6 g, 218 mL, 1.64 mol, 1.3 equivalents), and toluene (1063 mL). The solution was warmed to 85° C. and then treated dropwise with a solution of diphenylphosphoryl azide (346.8 g, 1.26 mol) over a period of 1.2 h. The solution was maintained at that temperature for an additional 1.Oh and then the mixture was treated with 4-methoxybenzyl alcohol (174.1 g, 1.26 mol) over a 0.33 h period from the dropping funnel. The solution was stirred at 88° C. for an additional 2.25 h and then cooled to room temperature. The contents of the flask were poured into a separatory funnel and washed with sat. aq. NaHCO$_3$ (2×500 mL), 0.2N HCl (2×500 mL), brine (1×500 mL), dried over anhyd. MgSO$_4$, filtered, and concentrated in vacuo to give 302.3 g, 85% of the desired product as a slightly brown oil. $_1$H NMR (CDCl$_3$) 300 MHz 7.32(d, J=8.4 Hz, 2H), 6.91(d, J=8.4 Hz, 2H), 5.2(brm, 1H), 5.05(s, 2H), 3.83(s, 3H), 3.70(s, 3H), 3.35(m, 2H), 2.70(m, 2H), 1.20(d, J=7.2 Hz, 3H).

G. Hydrolysis of Methyl N-Moz-α-methyl β-alanine: Preparation of α-methyl β-alanine Hydrochloride

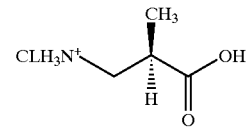

A 5 L three-necked round bottomed flask equipped with a reflux condenser, nitrogen inlet and mechanical stirrer was charged with methyl N-Moz-α-methyl β-alanine (218.6 g, 0.78 mol), glacial acetic acid (975 mL) and 12N hydrochloric acid (1960 mL). The solution was then heated to reflux for 3 h. After the solution had cooled to room temperature (ca. 1 h) the aqueous phase was decanted from organic residue (polymer) and the aqueous phase concentrated on a rotary evaporator. Upon addition of acetone to the concentrated residue a slightly yellow solid formed that was slurried with acetone and the white solid was isolated by filtration on a Buchner funnel. The last traces of acetone were removed by evacuation to give 97.7 g, 90% of pure product, mp 128.5–130.5° C. [α]$_d$ @ 25° C.=–9.0° C. (c=2.535, Methanol). $^1$H NMR (D$_2$O) 300 MHz 3.29(dd, J=8.6, 13.0 Hz, 1H), 3.16(dd, J=5.0, 13.0 m Hz, 1H), 2.94(ddq, J=7.2, 5.0, 8.6 Hz, 1H), 1.30(d,J=7.2 Hz, 3H); $^{13}$C NMR (D$_2$O) 180.84, 44.56, 40.27, 17.49.

H. Preparation of N-Boc α-Methyl β-Alanine

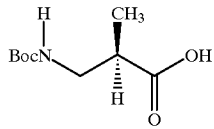

A solution of a-methyl b-alanine hydrochloride (97.7 g, 0.70 mol) in water (1050 mL) and dioxane (1050 mL) the pH was adjusted to 8.9 with 2.9N NaOH solution. This stirring solution was then treated with di-tert-butyl pyrocarbonate (183.3 g, 0.84 mol, 1.2 equivalents) all at once. The pH of the solution was maintained between 8.7 and 9.0 by the periodic addition of 2.5N NaOH solution. After 2.5 h the pH had stabilized and the reaction was judged to be complete. The solution was concentrated on a rotary evaporator (the temperature was maintained at <40° C.). The excess di-tert-butyl pyrocarbonate was removed by extraction with dichloromethane and then the aqueous solution was acidified with cold 1N HCl and immediately extracted with ethyl acetate (4×1000 mL). The combined ethyl acetate extract was washed with brine, dried over anhyd. MgSO$_4$, filtered and concentrated on a rotary evaporator to give a thick oil 127.3 g, 90% crude yield that was stirred with n-hexane whereupon crystals of pure product formed, 95.65 g, 67%, mp 76–78° C., [α]$_d$ @ 25° C.=–11.8° C. (c=2.4, EtOH). A second crop was obtained by concentration of the filtrate and dilution with hexane, 15.4 g, for a combined yield of 111.05 g, 78%. $^1$H NMR (acetone D$_6$) 300 MHz 11.7 (brs, 1H), 6.05 (brs 1H), 3.35 (m, 1H), 3.22 (m, 1H), 2.50 (m, 1H), 1.45(s, 9H), 1.19 (d, J=7.3 Hz, 3H); $^{13}$C NMR (acetone D$_6$) 177.01, 79.28, 44.44, 40.92, 29.08, 15.50. Elemental analysis calcd. for C$_9$H$_{17}$NO$_4$: C, 53.19, H, 8.42; N, 6.89. Found: C, 53.36; H, 8.46; N, 6.99.

I. Preparation of N-4-Methoxybenzyloxycarbonyl α-Methyl β-Alanine

A solution of N-4-methoxybenzyloxycarbonyl α-methyl β-alanine methyl ester (2.81 g, 10.0 mmol) in 30 mL of 25% aqueous methanol was treated with lithium hydroxide (1.3 equivalents) at room temperature for a period of 2 h. The solution was concentrated in vacuo and the residue taken up in a mixture of water and ether and the phases separated and the organic phase discarded. The aqueous phase was acidified with aqueous potassium hydrogen sulfate to pH=1.5 and then extracted three times with ether. The combined ethereal phase was washed with saturated aqueous sodium chloride solution, dried over anhydrous magnesium sulfate, filtered and concentrated in vacuo to give 2.60 g, 97% of N-4-Methoxybenzyloxycarbonyl α-methyl β-alanine (N-Moz-AMBA) which was purified by recrystallization from a mixture of ethyl acetate and hexane to give 2.44 g, 91% of pure product, mp 96–97° C., MH+=268. $^1$H NMR (D$_6$-acetone/300 MHz) 1.16 (3H, d, J=7.2Hz), 2.70 (1H, m), 3.31 (2H, m), 3.31 (3H, s), 4.99 (2H, s), 6.92 (2H, 4, J=8.7 Hz), 7.13 (2H, d, J=8.7 Hz).

EXAMPLE 8

Following generally the procedure of Example 7, the β-amino acids set forth in Table 1 were prepared.

TABLE 2

| Entry | R$^1$ | R$^{1'}$ | R$^{1''}$ |
|---|---|---|---|
| 1 | —CH$_3$ | H | H |
| 2 | —CH(CH$_3$)$_2$ | H | H |
| 3 | —C(CH$_3$)$_3$ | H | H |
| 4 | H | H | H |
| 5 | H | —CH$_3$ | H |
| 6 | H | —CH$_3$ | —CH$_3$ |
| 7 | H | H | —CO2CH$_3$ |
| 8 | H | H | —CONH$_2$ |
| 9 | —CH$_2$CH$_3$ | H | H |
| 10 | —CH$_2$CH(CH$_3$)$_2$ | H | H |
| 11 | —CH$_2$C$_6$H$_5$ | H | H |
| 12 | —CH$_2$—C$_6$H$_4$—OH | H | H |
| 13 | —CH$_2$—C$_6$H$_{11}$ | H | H |
| 14 | —CH$_2$COOH | H | H |
| 15 | H | —CH(CH$_3$)$_2$ | H |

TABLE 2-continued structure of β-amino acid: R1', R1'' on carbon bearing NH2; R1 on carbon bearing COOH

| Entry | R¹ | R¹' | R¹'' |
|---|---|---|---|
| 16 | H | —CH₂CH(CH₃)₂ | H |
| 17 | H | —CH₂—C₆H₅ | H |
| 18 | H | —CH₂CH₂—C₆H₅ | H |
| 19 | H | —(CH₂)₃—C₆H₅ | H |
| 20 | H | —(CH₂)₄—C₆H₅ | H |
| 21 | H | —(CH₂)₃CH(C₆H₅)₂ | H |

EXAMPLE 9

Utilizing generally the procedure set forth in Example 7, the following β-amino acid compounds were prepared.

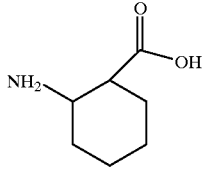

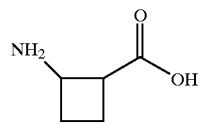

EXAMPLE 10A

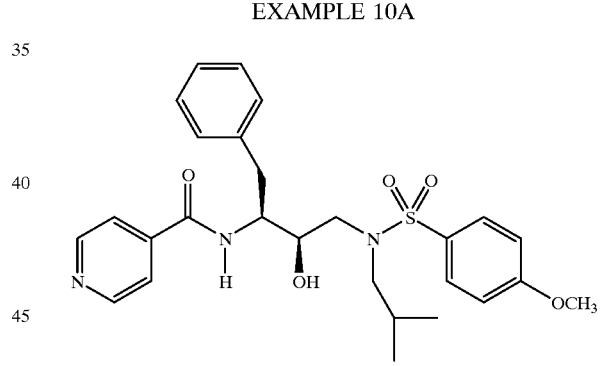

Preparation of 4-Pyridinecarboxamide, N-[2R-hydroxy-3-[[(4-methoxyyhenyl)sulfonyl](2-methylpropyl)amino]-1S-(-phenylmethyl)propyl]

To a solution of 231 mg (0.57 mmol) of 2R-hydroxy-3-[(2-methylpropyl)(4-methoxyphenyl)sulfonyl] amino-1S-

(phenylmethyl)propylamine in 3 mL of methylene chloride at 0 C, was added 288 mg(2.85 mmol) of triethylamine and then 112 mg(0.63 mmol) of isonicotinoyl chloride hydrochloride. After 19 hours at room temperature, the solvent was removed, ethyl acetate added, then washed with saturated sodium bicarbonate, brine, dried with magnesium sulfate, filtered and concentrated to afford 290 mg of crude product. This was chromatographed on silica gel using 3–5% isopropanol/methylene chloride as eluent to afford 190 mg of the desired compound; mass spectrum calc. for $C_{27}H_{34}N_3O_5S$ (M+H) 512.2219; found 512.2280.

EXAMPLE 10B

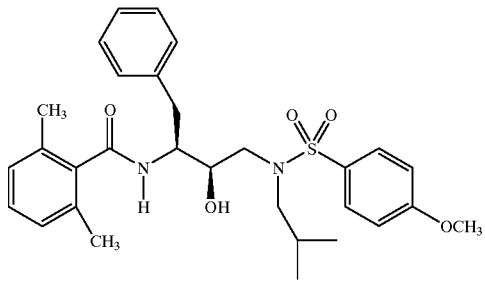

Preparation of Benzamide, N-[2R-hydroxy-3-[[(4-methoxyphenyl)sulfonyl](2-methylpropyl)amino]-1S-(-phenylmethyl)propyl]-2,6-dimethyl To a solution of 83 mg (0.55 mmol) of 2,6-dimethylbenzoic acid and 125 mg (0.82 mmol) of N-hydroxybenzotriazole in 3 mL of anhydrous DMF at 0 C was added 117 mg (0.61 mmol) of 1-(3-dimethylaminopropyl)-3-ethylcarbodiimide hydrochloride. After 2 hours at 0 C, 203 mg (0.50 mmol) of 2R-hydroxy-3-[(2-methylpropyl)(4-methoxyphenyl)sulfonyl]amino-1S-(phenylmethyl)propylamine was added. After 22 hours at room temperature, the solvent was removed in vacuo, ethyl acetate added, then washed with saturated sodium bicarbonate, brine, dried over magnesium sulfate, filtered and concentrated to afford 300 mg of crude product. Chromatography on silica gel using 20–50% ethyl acetate/hexane afforded 37 mg of the desired product; mass spectrum calcd for $C_{30}H_{38}N_2O_5S$ (M+H) 539.2580; found 539.2632.

EXAMPLE 10C

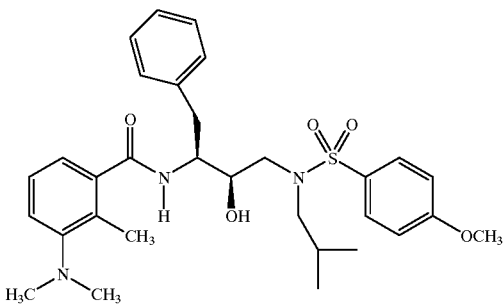

Preparation of Benzamide, N-[2R-hydroxy-3-[[(4-methoxyphenyl)sulfonyl](2-methylpropyl)amino]-1S-(phenylmethyl)propyl]-2-methyl.

Part A. Preparation of 4-Nitro-2-methylbenzoic Acid.

A mixture of 1.0 g(3.8 mmol) of 2-iodo-nitrotoluene, 2.1 g(15.2 mmol) potassium carbonate and 27 mg(0.038 mmol) of palladium(II) dichloride bis(triphenylphosphine) in a mixture of 5 mL of water and 10 mL of N,N-dimethylformamide. This was placed in a Fisher/Porter bottle under 15 psig of carbon monoxideand heated at 70 C for 16 hours. The solution became homogeneous when heated. The reaction was cooled, diethyl ether and water was added, the organic layer separated and discarded. The aqueous layer was acidified with iN hydrohloric acid, extracted with ethyl acetate, washed with water, brine, dried over magnesium sulfate, filtered and concentrated to yield 0.5 g of crude material. This dissolved in ethyl acetate, hexane added and the resulting brown solid discarded. The filtrate was concentrated, and then recrystallized fom diethyl ether/hexane to afford 215 mg of 4-nitro-2-methylbenzoic acid, m/e=182(M+H).

Part B. Preparation of Benzamide, N-[2R-hydroxy-3-[[(4-methoxyphenyl)sulfonyl](2-methylpropyl)amino]-1S-(phenylmethyl)propyl]-2-methyl-4-nitro.

To a solution of 181 mg(1.0 mmol) of 4-nitro-2-methylbenzoic acid and 230 mg(1.5 mmol) N-hydroxybenzotriazole in 3 mL of anhydrous N,N-dimethylformamide at 0 C, was added 211 mg(1.1 mmol) of 1-(3-dimethylaminopropyl)-3-ethylcarbodiimide hydrochloride. After stirring at 0 C for 1 hour, 406 mg(1 mmol) of 2R-hydroxy-3-[(2-methylpropyl)(4-methoxyphenyl)sulfonyl]amino-1S-(phenylmethyl)propylamine was added. After 17 hours at room temperature, the solvent was removed under reduced pressure, ethyl acetate added, washed with 5% citric acid, saturated sodium bicarbonate, brine, dried with magnesium sulfate, filtered and concentrated to yield 0.55 g of crude product. This was chromatographed on silica gel using 20–50% ethyl acetate/hexane as eluent to afford 0.49 g of the desired benzamide, N-[2R-hydroxy-3-[[(4-methoxyphenyl)sulfonyl](2-methylpropyl)amino]-1S-(phenylmethyl)propyl]-2-methyl-4-nitro, m/e=570(M+H).

Part C. Preparation of Benzamide, N-[2R-hydroxy-3-[[(4-methoxyphenyl)sulfonyl](2-methylpropyl)amino]-1S-(phenylmethyl)propyl]-2-methyl-4-amino.

A solution of 400 mg(0.70 mmol) of benzamide, N-[2R-hydroxy-3-[[(4-methoxyphenyl)sulfonyl](2-methylpropyl)amino]-1S-(phenylmethyl)propyl]-2-methyl-4-nitro from part B in 20 mL of methanol was hydrogenated over 0.2 g of 10% palladium on carbon catalyst under 50 psig of hydrogen for 2.5 hours. The catalyst was removed by filtration and the solution concentrated to afford 370 mg of the desired benzamide, N-[2R-hydroxy-3-[[(4-methoxyphenyl)sulfonyl](2-methylpropyl)amino]-1S-(phenylmethyl)propyl]-2-methyl-4-amino, m/e=540(M+H).

Part D. Preparation of Benzamide, N-[2R-hydroxy-3-[[(4-methoxyphenyl)sulfonyl](2-methylpropyl)amino]-1S-(phenylmethyl)propyl]-2-methyl-4-dimethylamino.

A solution of 0.17 g(0.31 mmol) of benzamide, N-[2R-hydroxy-3-[[(4-methoxyphenyl)sulfonyl](2-methylpropyl)amino]-1S-(phenylmethyl)propyl]-2-methyl-4-amino from part C in 5 mL of methanol and 0.20 mL of 37% aqueous formaldehyde was hydrogenated over 90 mg of 10% palladium on carbon under 15 psig of hydrogen for 16 hours. The catalyst was removed by filtration, the solvents removed under reduced pressure to afford 0.16 g of crude material. Chromatography on silica gel using 50% ethyl acetate as eluent afforded 0.12 g of the desired benzamide, N-[2R-hydroxy-3-[[(4-methoxyphenyl)sulfonyl](2-methylpropyl)amino]-1S-(phenylmethyl)propyl]-2-methyl-4-dimethylamino, m/e=568 (M+H).

EXAMPLE 10D

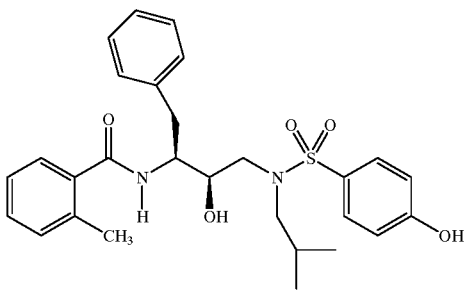

Preparation of Benzamide, N-[2R-hydroxy-3-[[(4-hydroxyphenyl)sulfonyl](2-methylpropyl)amino]1S-(phenylmethyl)propyl]-2-methyl.

To a solution of 500 mg(1 mmol) of 2R-hydroxy-3-[(2-methylpropyl)(4-hydroxyphenyl)sulfonyl]amino-1S-(phenylmethyl)propylamine in 2 mL of methylene chloride and 2 mL of N,N-dimethylformamide, was added 0.42 mL of triethylamine, followed by 0.12 mL of ortho-toluoyl chloride. After 17 hours, the solvent was removed under reduced pressure, the residue dissolved in ethyl acetate, was with 5% citric acid, saturated sodium bicarbonate and brine, dried over anhydrous magnesium sulfate, filtered and concentrated to afford 490 mg of crude material. This was chromatographed over 100 g of silica gel using 20–50% ethyl acetate/hexane as eluent to afford 232 mg of the desired product, m/e=511(M+H).

EXAMPLE 11A

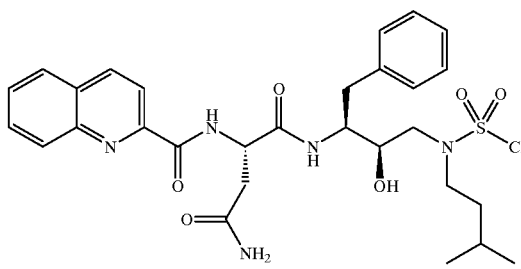

Preparation of N1-[2R-hydroxy-3-[(3-methylbutyl)(methyl-sulfonyl)amino]1S-(phenylmethyl)propyl]]-2S-[(2-quinolinylcarbonyl)amino]butanediamide Part A:

A solution of phenylmethyl [2R-hydroxy-3-[(3-methylbutyl)(methylsulfonyl)amino]-1S-(phenylmethyl)-propyl]carbamate prepared as in Example 3 (100 mg) in methanol (10 mL) was hydrogenated over 10% palladium on carbon for 2 hours, filtered through diatomaceous earth and concentrated to give the product as an oil.

Part B:

A solution of N—CBZ-L-asparagine (61 mg, 0.23 mmol) and N-hydroxybenzotriazole (33 mg, 0.22 mmol) in DMF (2 mL) was cooled to 0° C. with an ice bath and then EDC (42 mg, 0.22 mmol) was added. The solution was stirred for 30 minutes at 0° C. and then the product of Part A (69 mg, 0.21 mmol) in DMF (2 mL) was added. After 30 minutes at 0° C. the reaction was allowed to warm to room temperature and stir for 16 hours. The reaction mixture was then poured into a 50% saturated aqueous solution of sodium bicarbonate (100 mL) and the resulting white precipitate collected by suction filtration, washed with water and dried in vacuo. The phenylmethyl [3-amino-1S-[[2R-hydroxy-3-[(3-methylbutyl) (methylsulfonyl)amino]-1S-(phenylmethyl) amino]carbonyl]-3-oxopropyl]carbamate was obtained as a white solid Anal. Calcd. for $C_{28}H_{40}N_4O_7S \cdot 0.5 H_2O$: C, 57.42; H, 7.06; N, 9.57. Found: C, 57.72; H, 7.21; N, 9.24.

Part C:

A solution of phenylmethyl [3-amino-1S-[[2R-hydroxy-3-[(3-methylbutyl) (methylsulfonyl)amino]-1S-(phenylmethyl)amino]carbonyl]-3-oxopropyl]carbamate (135 mg, 0.23) in methanol (15 mL) was hydrogenated over 10% palladium on carbon for 6 hours, filtered through diatomaceous earth and concentrated to give the product as an oil.

Part D:

To a solution of the product from Part C (101 mg, 0.23 mmol) in DMF (5 mL) was added 2-quinoline carboxylic acid N-hydroxysuccinimide ester (67 mg, 0.25 mmol). The reaction was stirred at room temperature for 16 hours, then poured into a 50% saturated solution of sodium bicarbonate (60 mL). The resulting solid was collected by suction filtration washed with water and dried in vacuo. The N1-[2R-hydroxy-3-[(3-methylbutyl) (methylsulfonyl)-amino]-1S-(phenylmethyl)propyl]-2S-[(2-quinolinylcarbonyl)-amino]butanediamide was obtained as a white solid Anal. Calcd. for $C_{30}H_{39}N_5O_6S \cdot 0.1 H_2O$: C, 58.52; H, 6.71; N, 11.37. Found: C, 58.34; H, 6.35; N, 11.13.

EXAMPLE 11B

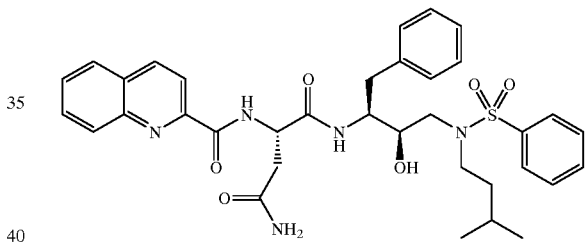

Preparation of N1-[2R-hydroxy-3-[(3-methylbutyl)(phenylsulfonyl)amino]-1S-(phenylmethyl)propyl]-2S-[(2-quinolinylcarbonyl)amino]butanediamide.

Part A:

The CBZ protected compound phenylmethyl [2R-hydroxy-3-[(3-methylbutyl)(phenylsulfonyl)amino]-1S-(phenylmethyl)propyl]carbamate (200 mg, 0.38 mmol) was deprotected by hydrogenation over 10% palladium on carbon and the resulting product obtained as an oil.

Part B:

The free amine from Part A was coupled with N-CBZ-L-asparagine (109 mg, 0.41 mmol) in the presence of N-hydroxybenzotriazole (63 mg, 0.41 mmol) and EDC (77 mg, 0.40 mmol) to give phenylmethyl [3-amino-1S-[[2R-hydroxy-3-[(3-methylbutyl) (phenylsulfonyl)amino]-1S-(phenylmethyl)amino]carbonyl]-3-oxopropyl]carbamate as a white solid Anal. Calcd. for $C_{33}H_{42}N_4O_7S$: C, 62.05; H, 6.63; N, 8.77. Found: C, 61.86; H, 6.60; N, 8.64.

Part C:

The product of Part B (110 mg, 0.17) was deprotected by hydrogenation over 10% palladium on carbon to give the product as an oil.

Part D:

The resulting free amine was coupled with 2-quinoline carboxylic acid N-hydroxysuccinimide ester (45 mg, 0.17 mmol) to give N1-[2R-hydroxy-3-[(3-methylbutyl)(phenylsulfonyl)amino]-1S-(phenylmethyl)propyl]-2S-[(2-quinolinylcarbonyl)amino]butanediamide as a white solid Anal. Calcd for $C_{35}H_{41}N_5O_6S$: C, 63.71; H, 6.26; N, 10.61. Found: C, 63.59; H, 6.42; N, 10.42.

EXAMPLE 12A

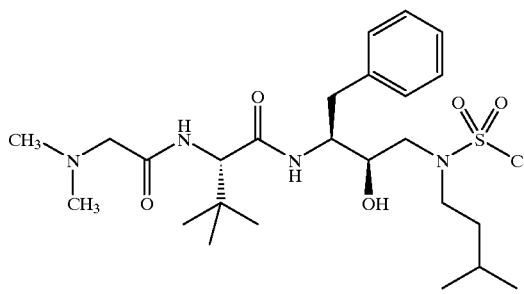

Preparation of 2S-[[(dimethylamino)acetyl]amino]-N-[2R-hydroxy-3-[(3-methylbutyl)(methylsulfonyl)amino]-1S-(phenylmethyl)propyl]-3,3-dimethylbutanamide Part A:

To a solution of N-CBZ-L-tert-leucine (100 mg, 0.38 mmol) and N-hydroxybenzotriazole (52 mg, 0.34 mmol) in DMF (3 mL) was added EDC (65 mg, 0.34 mmol). The solution was stirred for 60 minutes at room temperature and then the product of Example 10, Part A (105 mg, 0.32 mmol) in DMF (2 mL) was added. The reaction was stirred for 16 hours at room temperature, then poured into a 50% saturated solution of sodium bicarbonate (50 mL). The aqueous mixture was extracted twice with ethyl acetate (25 mL). The combined ethyl acetate layers were washed with water (25 mL) and dried over magnesium sulfate. Filtration and concentration produced an oil which was chromatographed on silica gel (50 gm) eluting with 2.5 % methanol in dichloromethane. The phenylmethyl [1S-[[[2R-hydroxy-3-[(3-methylbutyl)-(methylsulfonyl)amino]-1S-(phenylmethyl)propyl]amino]-carbonyl]-2,2-dimethylpropyl]carbamate was obtained as a gummy solid Anal. Calcd. for $C_{30}H_{45}N_3O_6S \lozenge 2.2 H_2O$: C, 58.55; H, 8.09; N, 6.83. Found: C, 58.38; H, 7.77; N, 7.10.

Part B:

A solution of phenylmethyl [1S-[[[2R-hydroxy-3-[(3-methylbutyl) (methylsulfonyl)amino]-1S-(phenylmethyl)propyl]amino]carbonyl]-2,2-dimethylpropyl]carbamate (100 mg, 0.17 mmol) in methanol (10 mL) was hydrogenated over 10% palladium on carbon for 2 hours. The reaction was filtered through diatomaceous earth and concentrated to an oil.

Part C:

N,N-dimethylglycine (20 mg, 0.19 mmol), N-hydroxybenzotriazole (28 mg, 0.18 mmol) and EDC (35 mg, 0.18 mmol) were stirred in DMF (4 mL) at room temperature for 40 minutes. The product from Part B in DMF (4 mL) was added and the reaction mixture stirred for 16 hours, then poured into a 50% saturated sodium bicarbonate solution (50 mL). The aqueous mixture was extracted three times with dichloromethane (30 mL) which in turn were washed with water (30 mL) and dried over magnesium sulfate. Filtration and concentration afforded an oil. The oil was chromatographed on silica gel (50 gm) eluting initially with 2.5% methanol in dichloromethane (400 mL) and then with 5% methanol in dichloromethane. The 2S-[[(dimethylamino)acetyl]amino]-N-[2R-hydroxy-3-[(3-methylbutyl)(methylsulfonyl)amino]-1S-(phenylmethyl)-propyl]-3,3-dimethylbutanamide was obtained as a white solid Anal. Calcd. for $C_{26}H_{46}N_4O_5S \lozenge 0.5 CH_2Cl_2$: C, 56.04; H, 8.34; N, 9.87. Found: C, 56.06; H, 8.36; N, 9.70.

EXAMPLE 12B

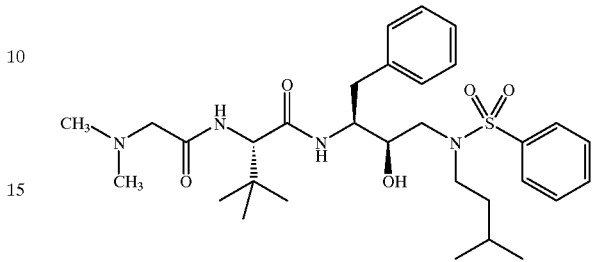

Preparation of 2S-[[(dimethylamino)acetyl]amino] N-[2R-hydroxy-3-[(3-methyl-butyl)(phenylsulfonyl)amino]-1S-(phenylmethyl)-propyl]-3,3-dimethylbutaneamide Part A:

To a solution of N-CBZ-L-tert-leucine (450 mg, 1.7 mmol) and N-hydroxybenzotriazole (260 mg, 1.7 mmol) in DMF (10 mL) was added EDC (307 mg, 1.6 mmol). The solution was stirred for 60 minutes at room temperature and then the product of Example 11, Part A (585 mg, 1.5 mmol) in DMF (2 mL) was added. The reaction was stirred for 16 hours at room temperature, then poured into a 50% saturated solution of sodium bicarbonate (200 mL). The aqueous mixture was extracted thrice with ethyl acetate (50 mL). The combined ethyl acetate layers were washed with water (50 mL) and saturated NaCl solution (50 mL), then dried over magnesium sulfate. Filtration and concentration produced an oil which was chromatographed on silica gel (50 gm) eluting with 20% ethyl acetate in hexane. The phenylmethyl [1S-[[[2R-hydroxy-3-[(3-methylbutyl) (phenylsulfonyl)amino]-1S-(phenylmethyl)propyl]amino]carbonyl]-2,2-dimethylpropyl]carbamate was obtained as a solid Anal. Calcd for $C_{35}H_{47}N_3O_6S$: C, 65.91; H, 7.43; N, 6.59. Found: C, 65.42; H, 7.24; N, 6.55.

Part B:

A solution of phenylmethyl [1S-[[[2R-hydroxy-3-[(3-methylbutyl) (phenylsulfonyl)-amino]-1S-(phenylmethyl)propyl]amino]carbonyl]-2,2-dimethylpropyl]carbamate (200 mg, 0.31 mmol) in methanol (15 mL) was hydrogenated over 10% palladium on carbon for 2 hours. The reaction was filtered through diatomaceous earth and concentrated to an oil.

Part C:

The resulting free amine from part B (150 mg, 0.3 mmol) was combined with diisopropylethylamine (114 uL, 0.33 mmol) in dichloromethane (5 mL). To this was added bromoacetyl chloride (27 uL, 0.33 mmol) dropwise. The reaction was stirred for 30 minutes at room temperature, then diluted with dichloromethane (30 mL) and extracted with 1 N HCl, water, and then saturated NaCl solution (25 mL each). The organic solution was dried over $MgSO_4$ and concentrated to a solid. The 2S-[[bromoacetyl]amino]-N-[2R-hydroxy-3-[(3-methylbutyl)(phenylsulfonyl)amino]-1S-(phenylmethyl)propyl]-3,3-dimethylbutaneamide was sufficiently pure for use in the next step. This material can also be prepared by substituing bromoacetic anhydride for bromoacetyl chloride, or one can use chloroacetyl chloride or chloracetic anhydride.

Part D:

The product from part C was dissolved in dichloromethane (5 mL) and diisopropylethylamine (114 uL, 0.66 mmol) and dimethylamine hydrochloride (53 mg, 0.66 mmol) were added. The reaction was stirred for 18 hours then concentrated under a stream of nitrogen to about 1 mL. The residue was chromatographed on silica gel (50 gm) using 2% methanol in dichloromethane. The 2S-[[(dimethylamino)-acetyl] amino]-N-[2R-hydroxy-3-[(3methylbutyl)-(phenylsulfonyl)amino]-1S-(phenylmethyl) propyl]-3,3-dimethylbutaneamide was obtained as a solid. Anal, Calcd for $C_{31}H_{48}N_4O_5S$: C, 63.24; H, 8.22; N, 9.52. Found: C, 63.03; H, 8.01; N, 9.40.

EXAMPLE 12C

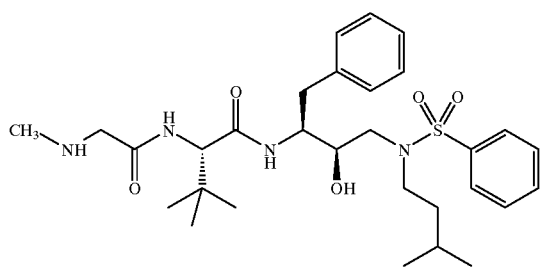

Preparation of 2S-[[(methylamino)acetyl]aminol]-N-[2R-hydroxy-3-[(3-methyl-butyl) (phenylsulfonyl)amino]-1S-(phenylmethyl)propyl]-3,3-dimethylbutaneamide 2S-[[bromoacetyl]amino]-N-[2R-hydroxy-3-[(3-methylbutyl)(phenylsulfonyl)amino]-1S-(phenylmethyl)propyl]-3,3-dimethylbutaneamide (103 mg, 0.16 mmol) and 40% aqueous methylamine (42 uL, 0.49 mmol) were combined in ethanol (2 mL) and stirred at room temperature for 24 hours. The reaction mixture was concentrated to dryness and triturated with ether. The solid material was removed by filtration and the filtrate concentrated to an oil. The oil was chromatographed on silica (50 gm) using 4% methanol in dichloromethane. The 2S-[[(methylamino)acetyl]amino]-N-[2R-hydroxy-3-[(3-methylbutyl)(phenylsulfonyl)amino]-1S-(phenylmethyl)propyl]-3,3-dimethylbutaneamide was obtained as a solid. Anal. Calcd for $C_{30}H_{46}N_4O_5S$: C, 62.69; H, 8.07; N, 9.75. Found: C, 62.38; H, 8.14; N, 9.60.

EXAMPLE 12D

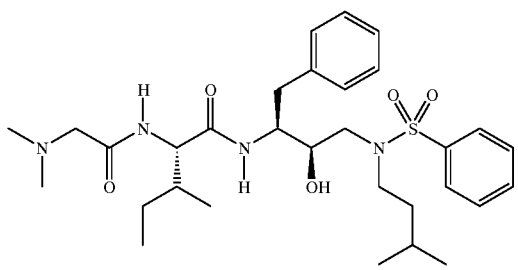

Preparation of Pentanamide, 2S-[[(Dimethylamino))acetyl]amino]-N-[2R-hydroxy-3-[(3-methylbutyl)phenylsulfonyl)amino]-1S-(phenylmethyl)propyl] 3S-methyl—

Part A:

To a solution the amine product of Example 11, Part A; (2.79 g, 7.1 mmol) in 27 mL of dioxane was added (2.3 g, 7.1 mmol) of N-t-butylcarbonyl-L-isoleucine-N-hydroxysuccinamide ester, and the reaction was stirred under nitrogen atmosphere for 16 hours. The contents of the reaction were concentrated in vacuo, and the residue dissolved in ethyl acetate, washed with potassium hydrogen sulfate (5% aqueous), saturated sodium bicarbonate, and saturated sodium chloride. The organic layer was dried over magnesium sulfate, filtered and concentrated to yield 4.3 grams of crude material which was chromatographed using 3:1 ethyl acetate: hexane to obtain 3.05 g, 72% yield of Pentanamide, 2S-[[(1,1-dimethylethoxy)carbonyl]amino]-N-[2R-hydroxy-3-[(3-methylbutyl)phenylsulfonyl)amino]-1S-(phenylmethyl)propyl]-3-methyl-.

Part B (3.05 g, 5.0 mmol) of the product from Part A; was dissolved in 20 mL of 4N HCl in dioxane and stirred under nitrogen atmosphere for 1.5 hours. The contents were concentrated in vacuo, and chased with diethyl ether. The crude hydrochloride salt was pumped on at 1 mm Hg until dry to yield 2.54 g of product as its hydrochloride salt.

Part C:

(2.54 g, 5.0 mmol) of amine hydrochloride was dissolved in 50 mL of tetrahydrofuran and to this was added (1.01 g, 10 mmol) of 4-methyl-morpholine, at which time a precipitate forms. To this suspension was added chloroacetic anhydride (0.865 g, 5.0 mmol) and stirred for 40 minutes. The contents were concentrated in vacuo, and the residue partitioned in ethyl acetate (200 mL) and 5% $KHSO_4$. The organic layer was washed with saturated sodium bicarbonate, and saturated sodium chloride, dried over magnesium sulfate, filtered and concentrated to yield the crude product. Purification by silica gel chromatography using an eluant of 1:1 ethyl acetate; hexanes yielded 1.89 grams of pure chloroacetamide.

Part D:

To a solution of chloroacetamide (1.89 g, 3.2 mmol) from Part C, in 25 mL of tetrahydrofuran was added 4.0 mL of 50% aqueous dimethylamine and the solution was stirred for 1 hour. The solution was concentrated in vacuo and the residue was dissolved in ethyl acetate and washed with water. The organic layer was dried over magnesium sulfate, filtered and concentrated to yield the crude product which was purified by crystallization from ethyl acetate and isooctane to yield 1.80 g, (88% yield), mp.=121–122 C, HRes. MS. calc. 589.3424, found 589.3405.

EXAMPLE 12E

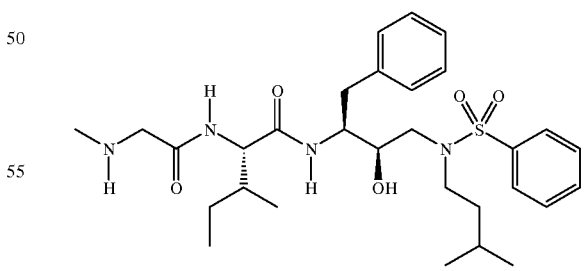

Preparation of Pentanamide, 2S-[[(Methylamino)acetyl]amino]N-[2R-hydroxy-3-[(3-methylbutyl)(phenylsulfonyl)amino]-1S-(phenylmethyl)propyl]-3S-methyl—

To a solution of the chloroacetamide of Example 12D, Part C, (2.36 g, 4.0 mmol) in tetrahydrofuran (25 mL) was added 3 mL of aqueous methylamine 40 wt %, and the reaction stirred for 1 hour. The contents were concentrated and the residue was partitioned between ethyl acetate (100 mL) and water (100 mL). The organic layer was dried over magnesium sulfate, filtered and concentrated to yield the crude product, which was purified by recrystallization from ethyl acetate heptane; (M+H)$_{575}$. HRes.found 575.3267.

EXAMPLE 12F

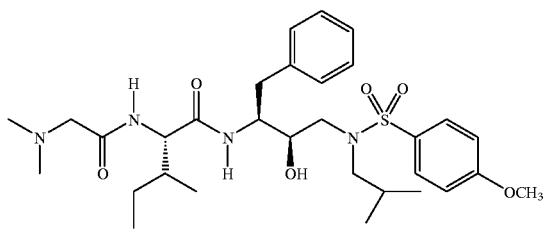

Preparation of Pentanamide, 2S-[[(Dimethylamino) acetyl]amino]-N-[2R-hydroxy-3-[(3-methylpropyl) (4-methoxyphenylsulfonyl)amino]-1S- (phenylmethyl) propyl]-3S-methyl—

Part A:

To a solution of 2R-hydroxy-3-[(2-methylpropyl)(4-methoxyphenylsulfonyl)amino]1-S-propylamine (1.70 g, 4.18 mmol) in 40 mL of dichloromethane was added N-carbobenzyloxy-L-isoleucine-N-hydroxysuccinamide ester (1.51 g, 4.18 mmol) and the solution stirred under nitrogen atmosphere for 16 hours. The contents were concentrated in vacuo and the residue was redissolved in ethyl acetate. The ethyl acetate solution was washed with an aqueous solution of 5% KHSO$_4$, saturated sodium bicarbonate, and saturated sodium chloride, dried over magnesium sulfate, filtered, and concentrated to yield 2.47 g of crude product. The product was purified by silica gel chromatography using 1 2:1 hexane:ethyl acetate eluant to yield 2.3 g. (84% yield) of Pentanamide, 2-[(carbobenzyloxy) amino]-N-[2-hydroxy-3-[(3-methylpropyl)(4-methoxyphenylsulfonyl)amino]-1-(phenylmethyl)propyl]-3-methyl-,[4-(R*,S*,S*,)].

Part B:

(1.18 g, 1.8 mmol) of the product from Part A was dissolved in 50 mL of methanol, and to this was added 250 mg of 10% Palladium on Carbon while under a stream of nitrogen. The suspension was hydrogenated using 50 psig of hydrogen for 20 hours. The contents were purged with nitrogen and filtered through celite, and concentrated in vacuo to yield 935 mg of Pentanamide, 2S-(amino)-N-[2R-hydroxy-3-[(3-methylpropyl)(4-methoxyphenylsulfonyl) amino]-1-S-(phenylmethyl)propyl]-3S-methyl-, which was used without further purification.

Part C:

(0.935 g, 1.8 mmol) of the amine from Part B was dissolved in 15 mL of dioxane and to this was added (190 mg, 1.85 mmol) of 4-methylmorpholine followed by (0.315 g, 1.8 mmol) of chloroacetic anhydride. The reaction mixture was stirred under nitrogen atmosphere for 3 hours, concentrated in vacuo, and redissolved in ethyl acetate. The ethyl acetate solution was washed with 50 mL of 5% agueous KHSO$_4$, saturated NaHCO$_3$, and saturated NaCl solution, dried over MgSO$_4$, filtered and concentrated to yield 613 mg, (68% yield) of Pentanamide, 2S-[(chloroacetyl)amino]-N-[2R-hydroxy-3-[(3-methylpropyl)(4-methoxyphenylsulfonyl)amino]-1S-(phenylmethyl) propyl]-3S-methyl-, after purification by silica gel chromatography using 1:1 hexane:ethyl acetate.

Part D:

To a solution of the chloroacetamide from Part C; (673 mg, 1.10 mmol) in 20 mL of tetrahydrofuran was added 5 mL of 50 wt % aqueous dimethylamine and the solution was stirred for 1 hour. The reaction was concentrated and the residue was redissolved in 50 mL of ethyl acetate and washed with 25 mL of water. The ethyl acetate layer was dried over magnesium sulfate, filtered and concentrated to yield a crude solid which was purified by silica gel column chromatography using an eluant of 97:3 dichloromethane:methanol to provide 400 mg of Pentanamide, 2S-[[Dimethylamino)acetyl]amino]-N-[2R-hydroxy-3-[(3-methylpropyl)(4-methoxyphenylsulfonyl)amino]-1S-(phenylmethyl)propyl]-3S-methyl-.

EXAMPLE 13A

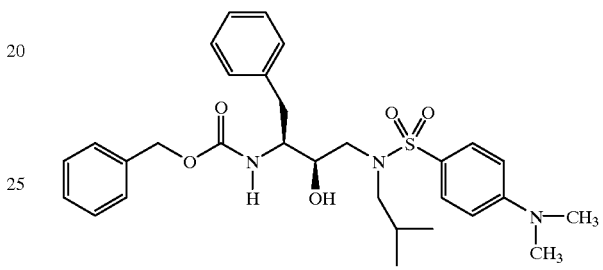

Preparation of Carbamic acid, [2R-hydroxy-3-[[(4-dimethylaminophenyl)sulfonyl](2-methylpropyl) amino]-1S-(phenylmethyl)propyl]-, phenylmethyl ester To a solution of 100 mg (0.19 mmol) of carbamic acid, [2R-hydroxy-3-[[(4-fluorophenyl)sulfonyl](2-methylpropyl)amino]-1S-(phenylmethyl)propyl]-, phenylmethyl ester in 1 mL of pyridine was added 53 μL of triethylamine and 120 μL (p.95 mmol) of 40% aqueous dimethylamine. After heating for 24 hours at 100 C, the solution was cooled, ethyl acetate added, then washed with 5% citric acid, saturated sodium bicarbonate, dried over magnesium sulfate, filtered and concentrated. The resulting solid was recrystallized from ethyl acetate/hexane to afford 10 mg of the desired product; mass spectrum m/e=540 (M+H).

EXAMPLE 13B

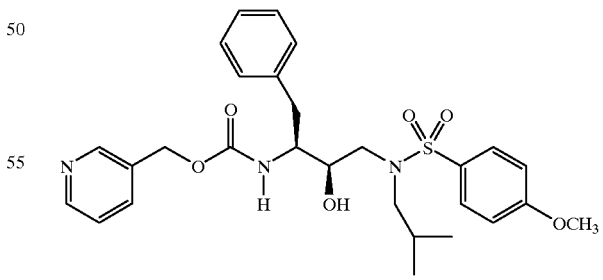

Preparation of Carbamic acid, [2R-hydroxy-3-[[(4-methoxyphenyl)sulfonyl](2-methylopropyl)amino]-1S-(phenylmethyl)propyl]-, 3-pyridylmethyl ester Part A:

A solution of N-benzyloxycarbonyl-3S-amino-1,2-S-epoxy-4-phenylbutane (50 g, 0.168 mol) and isobutylamine (246 g, 3.24 mol) in 650 mL of isopropyl alcohol was refluxed for 1.25 hours. The solution was cooled to room temperature, concentrated in vacuo and then poured into 1 L of stirring hexane whereupon the product crystallized from solution, was collected and air dried to give 57.6 g of N-[3S-benzyloxycarbonylamino-2R-hydroxy-4-phenyl]-N-isobutylamine, mp 108–109.5 C, mass spectrum m/e=371 (M+H).

Part B:

The amine from part A (1.11 g, 3.0 mmol) and triethylamine (324 mg, 3.20 mmol) in 20 mL of methylene chloride was treated with 715 mg(3.46 mmol) of 4-methoxybenzenesulfonyl chloride. The solution was stirred at room temperature for 6 hours, concentrated, dissolved in ethyl acetate, then washed with 1N potassium hydrogen sulfate, saturated sodium bicarbonate, brine, dried over magnesium sulfate, filtered and concentrated to afford a clear oil. This was recrystallized from diethyl ether to afford 1.27 g of carbamic acid, [2R-hydroxy-3-[[(4-methoxyphenyl)sulfonyl](2-methylpropyl)amino]-1S-(phenylmethyl)propyl]-, phenylmethyl ester, mp 97–101 C, mass spectrum m/e=541 (M+H).

Part C:

A solution of 930 mg (3.20 mmol) of the product of part B in 30 mL of methanol was hydrogenated in the presence of 70 mg of a 10% palladium on carbon catalyst under 40 psig for 17 hours, the catalyst was removed by filtration, and the solution concentrated to afford 704 mg of [2R-hydroxy-3-[[(4-methoxyphenyl)sulfonyl](2-methylpropyl)amino]-1S-(phenylmethyl)propylamine, mass spectrum m/e=407 (M+H), which was used directly in the next step without purification.

Part D:

To a solution of 2.5 g (22.9 mmol) of 3-pyridylcarbinol in 100 mL of anhydrous acetonitrile was added 8.8 g (34.4 mmol) of N,N'-disuccinimidyl carbonate and 5.55 mL (68.7 mmol) of pyridine. The solution was stirred for 1 hour and then concentrated in vacuo. The residue was dissolved in ethyl acetate, then washed with saturated sodium bicarbonate, brine, dried over magnesium sulfate, filtered and concentrated to afford 5.3 g of N-Hydroxysuccinimide-3-pyridylmethyl carbonate, mass spectrum m/e=251 (M+H), which was used directly in the next step without purification.

Part E:

To a solution of the amine from part C (2.87 g, 7.0 mmol) and 1.38 mL of triethylamine in 24 mL of anhydrous methylene chloride was added a solution of 1.65 g (6.6 mmol) of N-hydroxysuccinimide-3-pyridyl carbonate from part D in 24 mL of methylene chloride, The solution was stirred for 1 hour, 100 mL of methylene chloride added, then washed with saturated sodium bicarbonate, brine, dried over sodium sulfate, filtered and concentrated to afford 3.69 g of crude product. Chromatography on silica gel using 2% methanol/methylene chloride to afford 3.27 g of carbamic acid, [2R-hydroxy-3-[[(4-methoxyphenyl)sulfonyl](2-methylpropyl)amino]-1S-(phenylmethyl)propyl]-, 3-pyridylmethyl ester, mass spectrum m/e=548 (M+Li).

EXAMPLE 13C

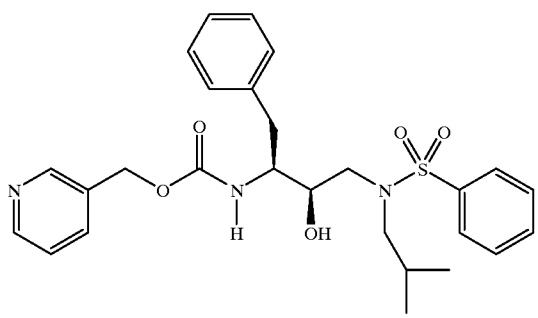

Preparation of Carbamic acid, [2R-hydroxy-3-[(phenylsulfonyl)(2-methylpropyl)amino]-1S-(phenylmethyl)propyl]-, 3-pyridylmethyl ester Part A:

A solution of N-benzyloxycarbonyl-3S-amino-1,2-S-epoxy-4-phenylbutane (50 g, 0.168 mol) and isobutylamine (246 g, 3.24 mol) in 650 mL of isopropyl alcohol was refluxed for 1.25 hours. The solution was cooled to room temperature, concentrated in vacuo and then poured into 1 L of stirring hexane whereupon the product crystallized from solution, was collected and air dried to give 57.6 g of N-[3S-benzyloxycarbonylamino-2R-hydroxy-4-phenyl]-N-isobutylamine, mp 108–109.5 C, mass spectrum m/e=371 (M+H).

Part B:

The amine from part A (0.94 g, 2.5 mmol) and triethylamine (288 mg,2.85 mmol) in 20 mL of methylene chloride was treated with 461 mg(2.61 mmol) of benzenesulfonyl chloride. The solution was stirred at room temperature for 16 hours, concentrated, dissolved in ethyl acetate, then washed with 1N potassium hydrogen sulfate, saturated sodium bicarbonate, brine, dried over magnesium sulfate, filtered and concentrated to afford a clear oil. This was recrystallized from diethyl ether and hexane to afford 0.73 g of carbamic acid, [2R-hydroxy-3-[(phenylsulfonyl)(2-methylpropyl)amino]-1S-(phenylmethyl)propyl]-, phenylmethyl ester, mp 95–99 C, mass spectrum m/e=511 (M+H).

Part C:

A solution of 500 mg of carbamic acid, [2R-hydroxy-3-[(phenylsulfonyl)(2-methylpropyl)amino]-1S-(phenylmethyl)propyl]-, phenylmethyl ester in 20 mL of methanol was hydrogenated in the presence of 250 mg of a 10% palladium on carbon catalyst under 40 psig for 3 hours, the catalyst was removed by filtration, and the solution concentrated to afford 352 mg of [2R-hydroxy-3-[(phenylsulfonyl])2-methylpropyl)amino]-1S-(phenylmethyl)propylamine, mass spectrum m/e=377 (M+H), which was used directly in the next step without purification.

Part D:

To a solution of 1.24 mmol of 5-norbornene-2,3-dicarboximido carbonochloridate (Henklein, P., et. al., Synthesis 1987, 166–167) in 1 mL of anhydrous methylene chloride, was added a solution of 43 μL (2.44 mmol) of 3-pyridylcarbinol and 129 4 μL (1.6 mmol) of pyridine in 1 mL of methylene chloride at 0° C. under a nitrogen atmosphere. After 4 hours at room temperature, 150 mg (0.4 mmol) of [2R-hydroxy-3-[(phenylsulfonyl])2-methylpropyl)amino]-1S-(phenylmethyl)propylamine from Part C above was added and 100 μL of pyridine. After stirring for 15 hours at room temperature, ethyl acetate was added, then washed with 1N hydrochloric acid, saturated sodium bicarbonate, brine, dried over magnesium sulfate, filtered and concentrated to afford 175 mg of crude product. Chromatography over silica gel using 1% methanol/methylene chloride tp afford 69 mg of pure carbamic acid, [2R-hydroxy-3-[(phenylsulfonyl)(2-methylpropyl)amino]-1S-(phenylmethyl)propyl]-, 3-pyridylmethyl ester, mass spectrum m/e=512.2267 (M+H); calcd for $C_{27}H_{33}N_3O_5S$, 512.2219.

EXAMPLE 13D

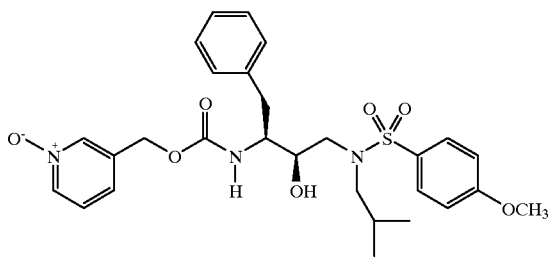

Preparation of Carbamic acid, [2R-hydroxy-3-[[(4-methoxyphenyl)sulfonyl](2-methylpropyl)amino]-1S-(phenylmethyl)-propyl]-, 3-pyridylmethyl ester, N-oxide To a solution of 211 mg (0.39 mmol) of carbamic acid, [2R-hydroxy-3-[[(4-methoxyphenyl)sulfonyl](2-methylpropyl)amino]-1S-(phenylmethyl)propyl]-, 3-pyridylmethyl ester in 5 mL of methylene chloride at 0 C was added 500 mg of 50% 3-chloroperbenzoic acid. After stirring at room temperature for 1 hour, ethyl acetate was added, the solution washed with saturated sodium bicarbonate, 0.2N ammonium hydroxide solution and brine, dried over magnesium sulfate, filtered and concentrated to afford 200 mg of crude product. This was chromatographed on C18 reverse phase material using 20–40% acetonitrile/water, then 100% acetonitrile to afford 90 mg of the desired product, which was then recrystallized from ethyl acetate/isooctane to yield 34 mg of pure carbamic acid, [2R-hydroxy-3-[[(4-methoxyphenyl)sulfonyl](2-methylpropyl)amino]-1S-(phenylmethyl)propyl]-, 3-pyridylmethyl ester, N-oxide; mass spectrum m/e=564 (M+Li).

EXAMPLE 13E

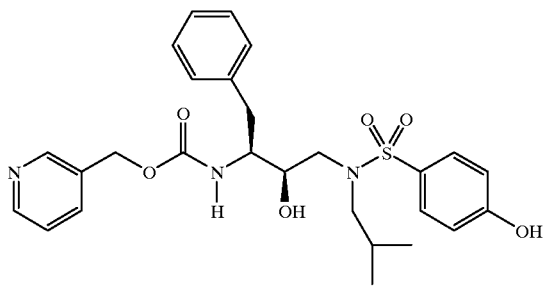

Preparation of Carbamic acid, [2R-hydroxy-3-[[(4-hydroxyphenyl)sulfonyl]-(2-methylpropyl)amino]-1S-(phenylmethyl)propyl]-, 3-pyridylmethyl ester Part A:

A solution of 0.98 g (1.85 mmol) of carbamic acid, [2R-hydroxy-3-[[(4-fluorophenyl)sulfonyl](2-methylpropyl)amino]-1S-(phenylmethyl)propyl]-phenylmethyl ester in 3.8 mL of anhydrous DMF was added to 22 mg (7.4 mmol) of 80% sodium hydride in 2 mL of DMF. To this mixture was added 0.40 g (3.7 mmol) of benzyl alcohol. After 2 hours, the solution was cooled to 0 C, water added, and then ethyl acetate. The organic layer was washed with 5% cirtic acid, saturated sodium bicarbonate and brine, dried over magnesium sulfate, filtered and concentrated to afford 0.90 g of crude material. This was chromatographed on basic alumina using 3% methanol/methylene chloride to afford 0.70 g of 2R-hydroxy-3-[(2-methylpropyl)(4-hydroxyphenyl)sulfonyl] amino-1S-(phenylmethyl)propylamine, cyclic carbamate; mass spectrum m/e=509(M+H).

Part B:

To a solution of 0.65 g (1.28 mmol) of the cyclic carbamate from part A in 15 mL of ethanol, was added 2.6 mL (6.4 mmol) of 2.5N sodium hydroxide solution. After 1 hour at reflux, 4 mL of water was added and the solution refluxed for an additional eight hours. The volatiles were removed, ethyl acetate added, and washed with water, brine, dried over magnesium sulfate, filtered and concentrated to afford 550 mg of crude2R-hydroxy-3-[(2-methylpropyl)(4-hydroxyphenyl)sulfonyl]amino-1S-(phenylmethyl) propylamine.

Part C:

A solution of crude 2R-hydroxy-3-[(2-methylpropyl)(4-benzyloxyphenyl)sulfonyl]amino-1S-(phenylmethyl) propylamine in 10 mL of ethanol was hydrogenated in the presence of 500 mg of a 10% palldium on carbon catalyst under 50 psig of hydrogen for 2 hours. The catalyst was removed by filtration and the solvent removed in vacuo to afford 330 mg of 2R-hydroxy-3-[(2-methylpropyl)(4-hydroxyphenyl) sulfonyl]amino-1S-(phenylmethyl) propylamine, mass spectrum m/e=393 (M+H).

Part D:

To a solution of 320 mg (0.82 mmol) of the amine from part C in 6 mL of DMF, was added 192 mg (0.76 mmol) of N-hydroxysuccinimide-3-pyridylmethyl carbonate. After 15 hours at room temperature, the DMF was removed in vacuo, ethyl acetate added, washed with water, brine, dried with magnesium sulfate, filtered and concentrated to afford 390 mg of crude material. Chromatogrpahy on silica gel using 50–80% ethyl acetate/hexane afforded 180 mg of carbamic acid, [2R-hydroxy-3-[[(4-hydroxyphenyl)sulfonyl](2-methylpropyl)amino]- 1S-(phenylmethyl)propyl]-,3-pyridylmethyl ester, mass spectrum m/e=528(M+H)

EXAMPLE 13F

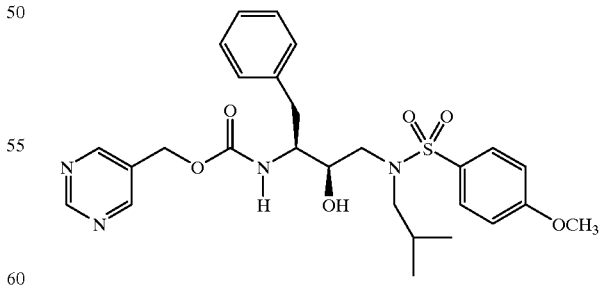

Preparation of Carbamic acid, [2R-hydroxy-3-[[(4-methoxy-phenyl)sulfonyl](2-methylpropyl)amino]-1S-(phenylmethyl)-propyl]-, 5pyrimidylmethyl ester To a solution of 9.5 mg (0.09 mmol) of 5-pyrimidylcarbinol in 1 mL of anhydrous acetonitrile at room temperature, was added 24 mg (0.09 mmol) of N,N'-disuccinimidyl carbonate and 19.1 μL (0.24 mmol) of pyridine. After stirring for 5 hours, 32 mg (0.08 mmol) of 2R-hydroxy-3-[(2-methylpropyl)(4-methoxyphenyl)sulfonyl]amino-1S-(phenylmethyl)propylamine was added and the solution stirred for 48 hours. After concentration in vacuo, methylene chloride was added, then washed with a 1:1 mixture of saturated sodium bicarbonate and brine, dried over magnesium sulfate, filtered and concentrated to give 27 mg of crude product. Chromatography on silica gel using 2% methanol/methylene chloride afforded 22 mg of the desired product, mass spectrum m/e=543(M+H).

EXAMPLE 13G

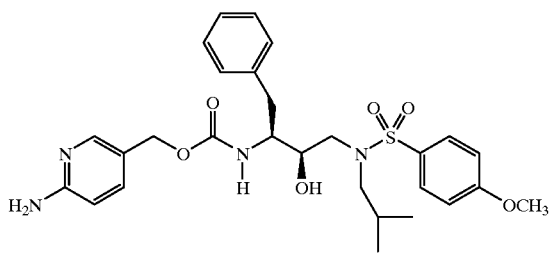

Preparation of Carbamic acid, [2R-hydroxy-3-[[(4-methoxyphenyl)sulfonyl](2-methylpropyl)amino]-1S-(phenylmethyl)propyl]-, 3-(6-aminopyridyl) methyl ester.

Part A. Prepartion of Ethyl 6-Aminonicotinate.

To a suspension of 1.3 g(9.4 mmol) 6-aminonicotinic acid in 100 mL of ethanol, was bubbled in dry hydrochloric acid at 0 C, then the solution was refluxed until all the solids dissolved. The solvents were removed under reduced pressure, the residue dissolved in ethyl acetate, washed with saturated sodium bicarbonate, brine and concentrated to afford 1.37 g of a white solid, m/e=166(M+H).

Part B. Preparation of Ethyl 6-(tert-Butyloxycarbonylamino)nicotinate.

A mixture of 848 mg(5.1 mmol) of ethyl 6-aminonicotinate from part A, 1.11 g(5.1 mmol) of di-tert-butylpyrocarbonate and 0.71 mL(5.1 mmol) of triethylamine in 10 mL of anhydrous toluene was refluxed for 15 hours. The solution was cooled, ethyl acetate added, washed with saturated sodium bicarbonate, brine, dried over anhydrous magnesium sulfate, filtered and concentrated to afford 1.28 g of the desired ethyl 6-(tert-butyloxycarbonylamino) nicotinate, m/e=267(M+H), which was used directly in the next step.

Part C. Preparation of 6-(tert-Butyloxycarbonylamino)-3-pyridylmethanol.

To 4.6 mL(4.6 mmol) of a 1M solution of lithium aluminum hydride in diethyl ether at −40 C under a nitrogen atmosphere, was added a solution of 618 mg(2.3 mmol) of ethyl 6-(tert-butyloxycarbonylamino)nicotinate from part B in 40 mL of anhydrous tetrahydrofuran. After the addition, this was warmed to room temperature, stirred for 3 hours, cooled to 0 C, and 145 μL of water, 145 μL of 20% sodium hydroxide solution and 290 μL of water were successively added. To the resulting mixture was added 50 mL of tetrahydrofuran and stirring continued for 30 minutes. Anhydrous magnesium sulfate was added, the solids removed via filtration and the filtrate concentrated under reduced pressure to afford 460 mg of the desired product, m/e=224(M+), which was used directly in the next step.

Part D. Preparation of Carbamic acid, [2R-hydroxy-3-[[(4-methoxyphenyl)sulfonyl](2-methylpropyl)amino]-1S-(phenylmethyl)propyl]-, 3-[(6-tert-butyloxycarbonylamino)pyridyl]methyl ester.

To a solution of 336 mg (1.5 mmol) of 6-(tert-butyloxycarbonylamino)-3-pyridylmethanol from part C in 14 mL of anhydrous acetonitrile at room temperature under a nitrogen atmosphere, was added 384 mg(1.5 mmol) of N,N'-disuccinimidyl carbonate and 364 μL(4.5 mmol) of anhydrous pyridine. After 4 hours, 406 mg(1 mmol) of 2R-hydroxy-3-[(2-methylpropyl)(4-methoxyphenyl) sulfonyl]amino-1S-(phenylmethyl)propylamine was added and stirring continued for 19 hours. The solvent was removed under reduced pressure, ethyl acetate added, washed with saturated sodium bicarbonate, brine, dried over magnesium sulfate, filtered and concentrated to afford 702 mg of crude product. Chromatography on silica gel using 1% methanol/methylene chloride as eluent afforded 170 mg of the desired carbamic acid, [2R-hydroxy-3-[[(4-methoxyphenyl)sulfonyl](2-methylpropyl)amino]-1S-(phenylmethyl)propyl]-, 3-[(6-tert-butyloxycarbonylamino)pyridyl]methyl ester, m/e=663(M+Li).

Part E. Preparation of Carbamic acid, [2R-hydroxy-3-[[(4-methoxyphenyl)sulfonyl](2-methylpropyl)amino]-1S-(phenylmethyl)propyl]-, 3-(6-aminopyridyl)methyl ester.

To 5 mL of 4N hydrochloric acid in dioxane at room temperature, was added 150 mg(0.23 mmol) of carbamic acid, [2R-hydroxy-3-[[(4-methoxyphenyl)sulfonyl](2-methylpropyl)amino]-1S-(phenylmethyl)propyl]-, 3-[(6-tert-butyloxycarbonylamino)pyridyl]methyl ester from part D. After stirring at room temperature for 28 hours, the solvent was removed under reduced pressure, the resulting solids triturated with diethyl ether, then dissolved in ethyl acetate and saturated sodium bicarbonate solution, separated, the organic layer washed with brine, dried with magnesium sulfate, filtered and concentrated. The residue was chromatographed on silica gel using 2.5% methanol/methylene chloride to yield 59 mg of the desired carbamic acid, [2R-hydroxy-3-[[(4-methoxyphenyl)sulfonyl](2-methylpropyl)amino]-1S-(phenylmethyl)propyl]-, 3-(6-aminopyridyl)methyl ester, m/e=557(M+H).

EXAMPLE 13H

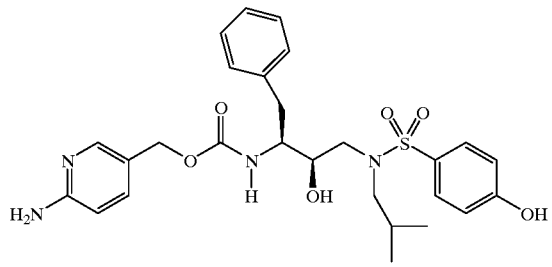

Preparation of Carbamic acid, [2R-hydroxy-3-[[(4-hydroxyphenyl)sulfonyl](2-methylpropyl)amino]-1S-(phenylmethyl)propyl]-, 3-(6-aminopyridyl) methyl ester.

Part A. Preparation of Carbamic acid, [2R-hydroxy-3-[[(4-methoxyphenyl)sulfonyl](2-methylpropyl)amino]- 1S-(phenylmethyl)propyl]-, 3-[(6-tert-butyloxycarbonylamino) pyridyl]methyl ester.

To a solution of 505 mg (2.25 mmol) of 6-(tert-butyloxycarbonylamino)-3-pyridylmethanol from in 20 mL of anhydrous acetonitrile at room temperature under a nitrogen atmosphere, was added 576 mg(2.25 mmol) of N,N'-disuccinimidyl carbonate and 546 μl(6.75 mmol) of anhydrous pyridine. After 1 hour, 837 mg(1.87 mmol) of 2R-hydroxy-3-[(2-methylpropyl)(4-hydroxyphenyl) sulfonyl]amino-1S-(phenylmethyl)propylamine was added and stirring continued for 3 hours. The solvent was removed under reduced pressure, ethyl acetate added, washed with saturated sodium bicarbonate, brine, dried over magnesium sulfate, filtered and concentrated to afford 1.37 g of crude product. Chromatography on silica gel using 1% methanol/ methylene chloride as eluent afforded 830 mg of material which was identified as a mixture of the desired carbamic acid, [2R-hydroxy-3-[[(4-hydroxyphenyl)sulfonyl](2-methylpropyl)amino]-1S-(phenylmethyl)propyl]-, 3-[(6-tert-butyloxycarbonylamino)pyridyl]methyl ester and the cyclic carbamate derived from the 2R-hydroxy-3-[(2-methylpropyl)(4-hydroxyphenyl)sulfonyl]amino-1S-(phenylmethyl)propylamine. The mixture was very difficult to separate, so was used as is in the next step.

Part B. Preparation of Carbamic acid, [2R-hydroxy-3-[[(4-hydroxyphenyl)sulfonyl](2-methylpropyl)amino]-1S-(phenylmethyl)propyl]-, 3-(6-aminopyridyl)methyl ester.

To 830 mg of the mixture from part A, was added 50 mL of a 1:1 mixture of trifluoroacetic acid and methylene chloride. After 2.5 hours at room temperature, the solvent was removed under reduced pressure, ethyl acetate added, washed with saturated sodium bicarbonate, dried over magnesium sulfate, filtered and concentrated to afford 720 mg of crude material. This was chromatgraphed on silica gel using 5% methanol/ethyl acetate as eluent to yield 220 mg of product, which was recrystallized from methylene chloride/ diethyl ether to afford 108 mg of the desired carbamic acid, [2R-hydroxy-3-[[(4-hydroxyphenyl)sulfonyl](2-methylpropyl)amino]-1S-(phenylmethyl)propyl]-, 3-(6-aminopyridyl)methyl ester, m/e=549(M+Li).

EXAMPLE 13I

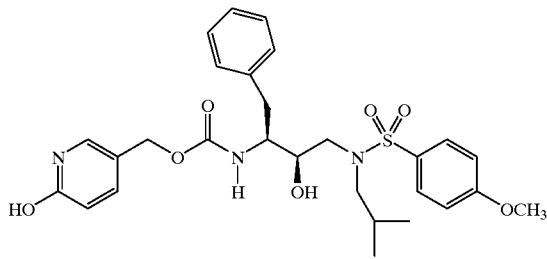

Preparation of Carbamic acid, [2R-hydroxy-3-[[(4-methoxyphenyl)sulfonyl](2-methylpropyl)amino]1S-(phenylmethyl)propyl]-, 3-(6-hydroxypyridyl) methyl ester.

Part A. Preparation of tert-Butyldimethylsilyl 6-(tert-butyldimethylsiloxy)nicotinate.

To a solution of 5.0 g(35.9 mmol) of 6-hydroxynicotinic acid in 200 mL of anhydrous N,N-dimethylformamide at room temperature, was added 8.56 g (125 mmol) of imidazole and then 13.5 g(89 mmol) of tert-butyldimethylsilyl chloride. After 20 hours, the solvent was removed under reduced pressure, ethyl acetate added, washed with water, 5% citric acid, saturated sodium bicarbonate, brine, dried over anhydrous magnesium sulfate, filtered and concentrated to afford 10.5 g of crude material, m/e=368(M+H).

Part B. Preparation of 3-(6-tert-butyldimethylsiloxy) pyridylcarbinol.

To 11 mL of 1M solution of lithium aluminum hydride in diethyl ether at −35 C under a nitrogen atmosphere, was added a solution of 2.0 g(5.46 mmol) of product from part A in 20 mL of anhydrous diethyl ether. After 30 minutes, the reaction was warmed to 0 C and stirred for 40 minutes. The solution was then quenched by the careful addition of 0.42 mL of water, 0.42 mL of 20% sodium hydroxide solution, and 0.84 mL of ater. Ethyl acetate was added, the precipate filtered and the organic phase concentrated to yield 0.93 g of crude 3-(6-tert-butyldimethylsiloxy)pyridylcarbinol, which was used directly in the next step.

Part C. Preparation of Carbamic acid, [2R-hydroxy-3-[[(4-methoxyphenyl)sulfonyl](2-methylpropyl)amino]-1S-(phenylmethyl)propyl]-, 3-(6-hydroxypyridyl)methyl ester.

To a solution of 860 mg(3.6 mmol) of material from part B in 15 mL of anhydrous acetonitrile, was added 919 mg(3.6 mmol) of N,N'disuccinimidyl carbonate and 0.87 mL of pyridine. After 1 hour, 1.42 g(3.5 mmol) of 2R-hydroxy-3-[(2-methylpropyl)(4-methoxyphenyl)sulfonyl]amino-1S-(phenylmethyl)propylamine was added. After 14 hours at room temperature, the solvent was removed under reduced pressure, the residue dissolved in ethyl acetate, washed with 5% citric acid, saturated sodium bicarbonate, brine, dried over magnesium sulfate, filtered and concentrated to afford 2.1 g of crude material. This was directly deprotected by dissolving in 40 mL of 80% acetic acid/water and stirring for 2 hours. The solvents were removed under reduced pressure, the residue dissolved in ethyl acetate, washed with saturated sodium bicarbonate, brine, dried over magnesium sulfate, filtered and concentrated to afford 1.7 g of crude product. This was chromatographed on silica gel using 50–100% ethyl acetate/hexane to provide a fraction of 0.19 g of fairly pure material, which was further purified by reverse phase chromatography using 15–40% acetonitrile/water(0.05% trifluoroacetic acid) to provide 120 mg of the desired carbamic acid, [2R-hydroxy-3-[[(4-methoxyphenyl)sulfonyl](2-methylpropyl)aminon]-1S-(phenylmethyl)propyl]-, 3-(6-hydroxypyridyl)methyl ester, m/e=558(M+H)

EXAMPLE 13J

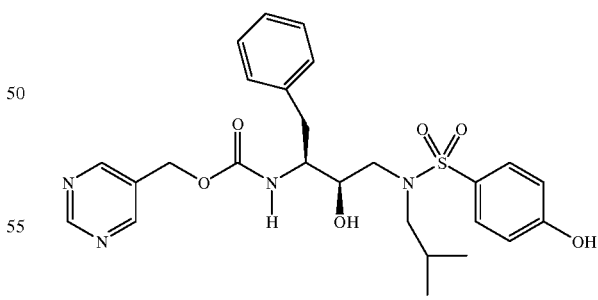

Preparation of Carbamic acid, [2R-hydroxy-3-[[(4-hydroxyphenyl)sulfonyl](2-methylpropyl)amino]-1S-(phenylmethyl)propyyl], 5-pyrimidylmethyl ester.

To a solution of 237 mg (2.15 mmol) of 5-pyrimidylcarbinol in 24 mL of anhydrous acetonitrile , was added 602 mg is (2.35 mmol) of N,N'-disuccinimidyl carbonate and then 0.47 mL of pyridine. After stirring for 4.5 hours, 766 mg(196 mmol) of 2R-hydroxy-3-[(2-methylpropyl)(4-hydroxyphenyl)sulfonyl]amino-1-(phenylmethyl)propyl amine was added. After stirring for 19 hours, the solvent was removed under reduced pressure, ethyl acetate added, washed with 5% citric acid, saturated sodium bicarbonate, brine, dried over anhydrous magnesium sulfate, filtered and concentrated to afford 1.0 g of crude material. Chromatography on silica gel using 50–100% ethyl acetate/hexane as eluent afforded 450 mg of the desired carbamic acid, [2R-hydroxy-3-[[(4-hydroxyphenyl)sulfonyl](2-methylpropyl)amino]-1S-(phenylmethyl)propyl]-, 5-pyrimidylmethyl ester, m/e=529(M+H).

EXAMPLE 14

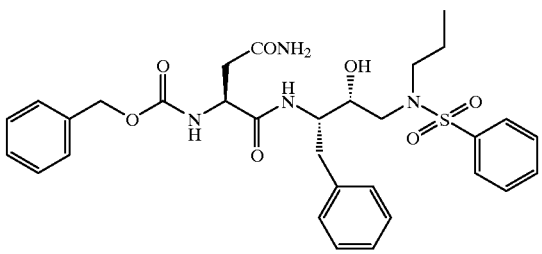

Preparation of phenylmethyl[3-amino-1S-[[2R-hydroxy-3-[(3-propyl) (phenylsulfonyl)amino]-1S-(phenylmethyl)amino]-carbonyl]-3-oxopropyl] carbamate Phenylmethyl[2R-hydroxy-3-[(3-propyl) (phenylsulfonyl)amino]-1S-(phenylmethyl)propyl]-carbamate (200 mg, 0.40 mmol) was deprotected by hydrogenation over 10% palladium on carbon and the resulting free amine was coupled with N-CBZ-L-asparagine (157 mg,0.42 mmol) in the presence of N-hydroxybenzotriazole (114 mg, 0.84 mmol) and EDC (130 mg, 0.67 mmol) to give phenylmethyl [3-amino-1S-[[2R-hydroxy-3-[(3-propyl) (phenylsulfonyl)amino]-1S-(phenylmethyl)amino] carbonyl]-3-oxopropyl]carbamate as a solid. Anal. Calcd for $C_{31}H_{38}N_4O_7S.0.2H_2O$: C,60.61; H,6.30; N,9.12. Found: C,60.27; H,6.16; N,8.93.

EXAMPLE 15A

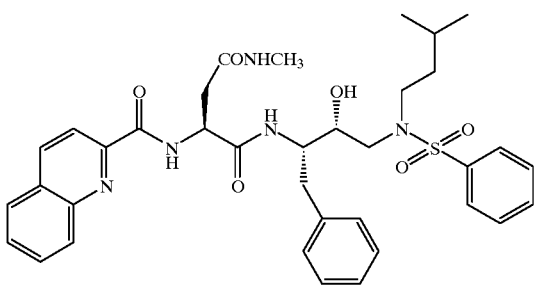

Preparation of N1-[2R-hydroxy-3-[(3-methylbutyl) (phenyl-sulfonyl)amino]-N4-methyl-1S-(phenylmethyl) propyl]-2S-[(2-quinolinylcarbonyl)amino]butanediamide Part A:

N2-[(1,1-dimethylethoxy)carbonyl]-N-methyl-L-asparagine was prepared from Boc-L-aspartic acid alpha-benzyl ester(1.0 g, 3.09 mmol), methylamine.HCl (209 mg, 3.09 mmol), EDC(711 mg, 3.7 mmol), 1-hydroxybenzotriazole (627 mg, 4.63 mmol), and N-methylmorpholine (0.7 mL, 6.3 mmol), in DMF (20 mL). After stirring overnight at r.t., the reaction mixture was diluted with ethyl acetate, washed with water, sat. sodium bicarbonate, 5% citric acid, brine, dried over magnesium sulfate and concentrated to an oil. The oil was taken up in 20 mL dry ethanol, and hydrogenated in the presence of 10% w/w of 10% Pd on C at atmospheric pressure and room temperature overnight. The mixture was filtered through Celite and concentrated to a white solid foam, 670 mg.

Part B:

A solution of phenylmethyl [2R-hydroxy-3-[(3-methylbutyl) (phenylsulfonyl)amino]-1S-(phenylmethyl)-propyl]carbamate (310 mg, 0.59 mmol) in methanol (10 mL) was hydrogenated over 10% palladium on carbon for 3 h., filtered through diatomaceous earth and concentrated to give the product as an oil (214 mg) This free amine (208 mg, 0.53 mmol) was coupled with N2-[(1,1-dimethylethoxy)-carbonyl]-N-methyl-L-asparagine (137 mg, 0.56 mmol) in the presence of N-hydroxybenzotriazole (102 mg, 0.76 mmol) and EDC (130 mg, 0.67 mmol) to yield 290 mg of N1[2R-hydroxy-3-[(3-methylbutyl) (phenylsulfonyl)-amino]-N4-methyl-1S-(phenylmethyl)propyl]-2S-[(1,1-dimethylethoxy-carbonyl) amino]butane diamide.

Part C:

N1[2R-hydroxy-3-[(3-methylbutyl) (phenyl-sulfonyl) amino]-N4-methyl-1S-(phenylmethyl)propyl]-2S-[(1,1-dimethylethoxycarbonyl)-amino]butane diamide(270 mg, 0.43 mmol) was stirred in 4N HCl in dioxane (5 mL) at r.t. for 0.5 h. Solvent and excess reagent were evaporated to dryness. The product was dried in vacuo. This material (125 mg, 0.225 mmol) was then reacted with 2-quinoline carboxylic acid N-hydroxysuccimide ester (61 mg, 0.225 mmol), N-methylmorpholine (50 uL, 0.45 mmol) in methylene chloride (2 mL) for 3 h. The product N1 [2R-hydroxy-3-[(3-methylbutyl) (phenylsulfonyl)amino]-N4-methyl-1S-(phenylmethyl)propyl]-2S-[(2-quinolinylcarbonyl)-amino] butane diamide was purified by silica gel chromatography. Anal. Calcd for $C_{36}H_{43}N_5O_6S.0.2H_2O$: C,63.83; H,6.45; N,10.34. Found: C,63.64; H,6.40; N,10.34.

EXAMPLE 15B

Following the procedures set forth above, the following compound was also prepared:

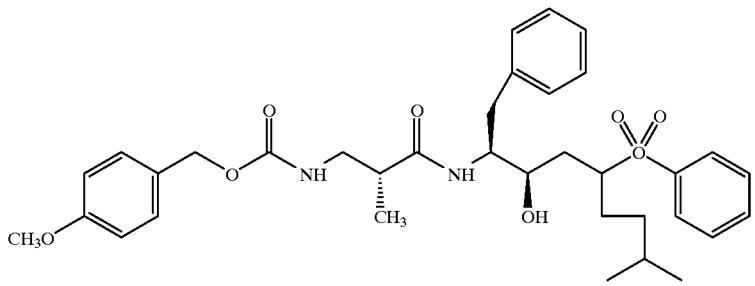

Preparation of Carbamic acid, [3-[[2-hydroxy-3-[(3-methylbutyl)(phenylsutonyl)amino]-1-(phenylmethyl)propyl]amino]-2-methyl-3-oxopropyl]-, (4-methoxyohenyl)methyl ester, [1S-[1R*(S*),2S*]—

Thus, 4.10 g, (7.8 mmol), of Carbamic acid, [2R-hydroxy-3-[(3-methylbutyl) (phenylsulphonyl)amino]-1S-(phenylmethyl) propyl]-, phenylmethyl ester, [R-(R*,S*)]- was hydrogenated in a solution of methanol and ethanol using catalytic Pd/C 10% at 50 psig hydrogen for 3 hours. The catalyst was filtered and the solvents removed in vacuo to yield 3.0 grams of free amine.

In a separate flask, 2.09 g, (7.8 mmol), of N-Moz-AMBA was added to 10 mL of dimethylformamide and 1.58 g, (1.5 equiv.), of N-hydroxybenzoltriazole and the solution was cooled to 5 degrees C. To this solution was added 1.49 g, (7.8 mmol), of EDC and the solution stirred for 30 min. To this was added the free amine in 10 mL of dimethylformamide, and the reaction was stirred for 20 hours. The solvent was removed by evaporation and the crude material was partitioned between ethyl acetate and saturated aqueous sodium bicarbonate. The ethyl acetate layer was washed with 5% potassium hydrogen sulfate and brine, dried over magnesium sulfate, filtered and concentrated to yield 2.58 grams of pure product after recrystallization from ethyl acetate, ether, and hexanes. 52% yield.

EXAMPLE 16A

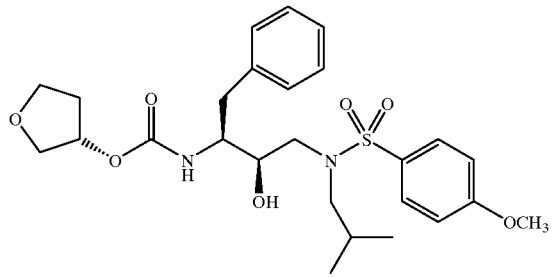

Preparation of Carbamic acid, [2R-hydroxy-3-[(4-methoxyyhenylsulfonyl) (2-methylpronyl)amino]-1S-(phenylmethyl)propyl-, 3-S-tetrahydrofuran-3-yl-ester To a solution of 406 mg (1.0 mmol) of [2R-hydroxy-3-[[(4-methoxyphenyl)sulfonyl](2-methylpropyl)amino]-1S-(phenylmethyl) propylamine in 5.0 mL of dichloromethane containing 150 mg(1.Smmol) of triethylamine was added 280 mg (1.22 mmol) of N-succinimidyl-3-(S)-tetrahydrofuranyl carbonate and the reacton mixture was stirred for 2 hours, an additional 136 mg (0.3 mmol) of amine was added to the mixture and the solution stirred another 2 hours. The contents were diluted with 50 mL of ethyl acetate and washed with 5% aqueous citric acid, saturated sodium bicarbonate, and brine, then dried over magnesium sulfate, filtered and concentrated to yield 330 mg of crude product. Purification by silica gel chromatography using an eluant of 1:1 to 2:1 ethyl acetate/hexanes gradient provided Carbamic acid, [2R-hydroxy-3-[(4-methoxyphenylsulfonyl) (2-methylpropyl) amino]-1S-(phenylmethyl)propyl-, 3-S-tetrahydrofuran-3-yl-ester as a white solid. m/z=521 (M+H) calc. 521.2311 obs. 521.2311.

EXAMPLE 16B

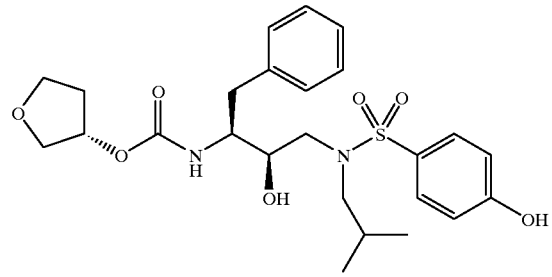

Preparation of Carbamic acid, [2R-hydroxy-3-[(4-hydroxyphenylsulfonyl) (2-methylpropyl)amino]-1S-(phenylmethyl)propyl-, 3-S-tetrahydrofuran-3-yl-ester To a solution of 435 mg (1.0 mmol) of [2R-hydroxy-3-[[(4-hydroxyphenyl)sulfonyl](2-methylpropyl)amino]-1S-(phenylmethyl) propylamine in 3.0 mL of dimethylformamide was added 225 mg (0.98 mmol) of N-succinimidyl-3-(S)-tetrahydrofuranyl carbonate and the solution was stirred overnight. The mixture was diluted with 50 mL of ethyl acetate and washed with 5% aqueous citric acid, saturated sodium bicarbonate, and brine, dried over magnesium sulfate, filtered and concentrated to yield 515 mg of crude product. Purificaton by silica gel chromatography using and eluant of 1:1 ethyl acetate :hexanes provided 315 mg of Carbamic acid, [2R-hydroxy-3-[(4-hydroxyphenylsulfonyl) (2-methylpropyl)amino]-1S-(phenylmethyl)propyl-, 3-S-tetrahydrofuran-3-yl-ester, as a white solid. m.p=HRMS calc. 507.2165, obs. 507.2155.

EXAMPLE 16C

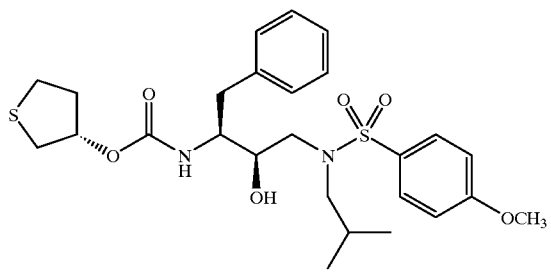

Preparation of Carbamic acid, [2R-hydroxy-3-[(4-methoxyyphenylsulfonyl) (2-methylpronyl)amino]-1S-(phenylmethyl)propyl-, 3-S-tetrahydrothiophen-3-yl-ester To a solution of 215 mg (2.0 mmol) of 3-S-hydroxythiophene, 415 µL of anhydrous pyridine,and 2 mL of dry acetonitrile was added 512 mg (2.0 mmol) of N,N'-Dimethylsuccinimidyl carbonate and this suspension was stirred for 45 minutes. To this clear solution was added a solution of 700 mg (1.7 mmol) of [2R-hydroxy-3-[[(4-methoxyyphenyl)sulfonyl](2-methylpropyl)amino]-1S-(phenylmethyl)propylamine in 2.0 mL of acetonitrile and stirred for 12 hours. the contents were concentrated, and the residue was partitioned between ethyl acetate and 5% aqueous potassium hydrogen sulfate. The organic layer was washed with saturated sodium bicarbonate and then brine, dried over sodium sulfate, filtered and concentrated to yield 780 mg of crude material. Purificaton by silica gel chromatograpy using an eluant of 10:10:1 ethyl acetate: hexane:methanol provided 520 mg of Carbamic acid, [2R-hydroxy-3-[(4-methoxyphenylsulfonyl) (2-methylpropyl)amino]-1S-(phenylmethyl)propyl-, 3-S-tetrahydrothiophen-3-yl-ester, as a crystalline white solid. m.p.=162–3° C., m/z=553 (M+H).

EXAMPLE 16D

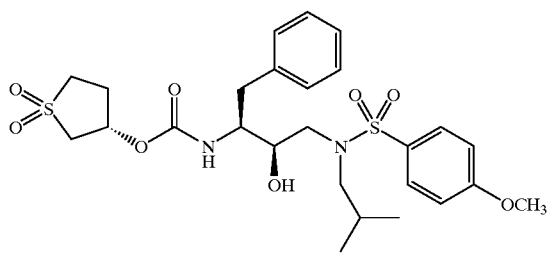

Preparation of Carbamic acid, [2R-hydroxy-3-[(4-methoxyphenylsulfonyl) (2-methylpropyl)amino]-1S-(phenylmethyl)propyl-, 3(S)-1,1-dioxotetrahydrothiophen-3-yl-ester To a solution of 270 mg (0.5 mmol) of Carbamic acid, [2R-hydroxy-3-[(4-methoxyphenylsulfonyl) (2-methylpropyl)amino]-1S-(phenylmethyl)propyl-, 3-S-tetrahydrothiophen-3-yl-ester in 30 mL of dichloromethane was added 400 mg (1.2 mmol) of m-chloroperbenzoic acid (50 wt %) and the mixture was stirred for 12 hours. The contents were diluted with 10 mL of 10% aqueous sodium metabisulfite and stirred for 30 minutes. The organic layer was washed with saturated sodium bicarbonate, dried over sodium sulfate, filtered and concentrated to yield 290 mg of crude product. Purification by silica gel chromatography using an eluant of 10:10:1 ethyl acetate:hexane:methanol provided 260 mg of Carbamic acid, [2R-hydroxy-3-[(4-methoxyphenylsulfonyl) (2-methylpropyl)amino]-1S-(phenylmethyl)propyl-, 3(S)-1,1-dioxotetrahydrothiophen-3-yl-ester, as a white crystalline solid. m.p.=69° C., m/z=569 (M+H).

EXAMPLE 16E

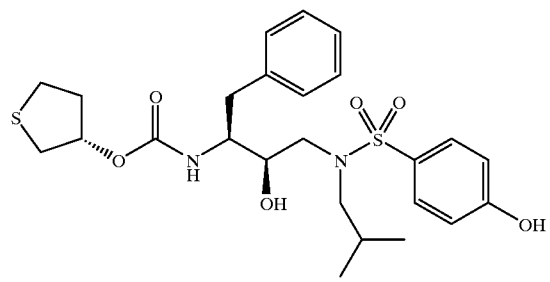

Preparation of Carbamic acid, [2R-hydroxy-3-[(4-hydroxythenylsulfonyl) (2-methylpropyl)amino]-1S-(phenylmethyl)propyl-, 3-S-tetrahydrothiophen-3-yl-ester To a solution of 125 mg (1.2 mmol) of 3-S-hydroxythiophene, 250 µL of anhydrous pyridine,and 1 mL of dry acetonitrile was added 307 mg (1.2 mmol) of N,N'-Dimethylsuccinimidyl carbonate and this suspension was stirred for 45 minutes. To this clear solution was added a solution of 445 mg (1.0 mmol) [2R-hydroxy-3-[[(4-hydroxyphenyl)sulfonyl](2-methylpropyl)amino]-1S-(phenylmethyl) propylamine in 1.0 mL of acetonitrile and stirred for 12 hours. the contents were concentrated, and the residue was partitioned between ethyl acetate and 5% aqueous potassium hydrogen sulfate. The organic layer was washed with saturated sodium bicarbonate and then brine, dried over sodium sulfate, filtered and concentrated to yield 460 mg of crude material. Purificaton by silica gel chromatograpy using an eluant of 10:10:1 ethyl acetate: hexane:methanol provided 235 mg of Carbamic acid, [2R-hydroxy-3-[(4-hydroxyphenylsulfonyl) (2-methylpropyl) amino]-1S-(phenylmethyl)propyl-, 3-S-tetrahydrothiophen-3-yl-ester, as a crystalline white solid. m.p.=184–85° C., m/z=529 (M+Li).

EXAMPLE 16F

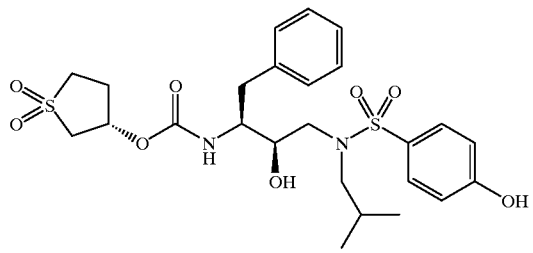

Preparation of Carbamic acid, [2R-hydroxy-3-[(4-hydroxyphenylsulfonyl) (2-methyl-ronyl)amino]-1S-(phenylmethyl)propyl-, 3(S)-1,1-dioxotetrahydrothionhen-3-yl-ester To a solution of 125 mg (0.24 mmol) of Carbamic acid, [2R-hydroxy-3-[(4-hydroxyphenylsulfonyl) (2-methylpropyl)amino]-1S-(phenylmethyl)propyl-, 3-S-tetrahydrothiophen-3-yl-ester in 30 mL of dichloromethane was added 240 mg (0.7 mmol) of m-chloroperbenzoic acid (50 wt %) and the mixture was stirred for 12 hours. The contents were diluted with 5 mL of 10% aqueous sodium metabisulfite and stirred for 30 minutes. The organic layer was washed with saturated sodium bicarbonate, dried over sodium sulfate, filtered and concentrated to yield 110 mg of crude product. Purification by silica gel chromatography using an eluant of 1:1 to 2:1 ethyl acetate:hexane:methanol provided 100 mg of Carbamic acid, [2R-hydroxy-3-[(4-hydroxyphenylsulfonyl) (2-methylpropyl)amino]-1S-(phenylmethyl)propyl-, 3(S)-1,1-dioxotetrahydrothiophen-3-yl-ester, as a white crustalline solid, m.p.=190–1° C., m/z=561 (M+Li).

EXAMPLE 17A

Carbamic acid, [2R-hydroxy-3-[[(4-methoxyphenyl)sulfonyl](methylpropyl)amino]- 1S-(phenylmethyl)propyl]-,5-(thiazolyl)methyl ester can be prepared according to the following procedures.

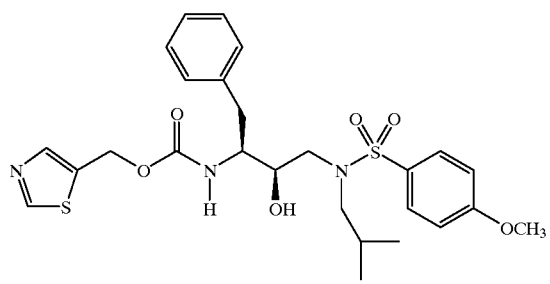

To a solution of 172 mg (1.5 mmol) of 5-hydroxymethylthiazole in 14 mL of anhydrous acetonitrile at room temperatures under a nitrogen atmosphere, is added 384 mg (1.5 mmol) of N,N'-disuccinimidyl carbonate and 364 μL (4.5 mmol) of anhydrous pyridine. After about 4 hourse, 406 mg (1 mmol) of 2R-hydroxy-3-[(2-methylpropyl) (4-methoxyphenyl)sulfonyl]amino-1S-(phenylmethyl)propylamine is added and stirring would be continued for approximately 19 hours. The solvent would be removed under reduced pressure, ethyl acetate added, washed with saturated sodium bicarbonate, brine, dried over magnesium sulfate, filtered and concentrated to afford crude product. The desired carbamic acid, [2R-hydroxy-3-[[(4-methoxyphenyl)sulfonyl](2-methylpropyl)amino]-1S-(phenylmethyl)propyl]-,5-(thiazolyl)methyl ester could be isolated in pure form through chromatography on silica gel using 50–100% ethyl acetate/hexane as eluent.

EXAMPLE 17B

Carbamic acid, [2R-hydroxy-3-[[(4-hydroxyphenyl)sulfonyl](methylpropyl)amino]-1S-(phenylmethyl)propyl]-,5-(thiazolyl)methyl ester can be prepared according to the following procedure

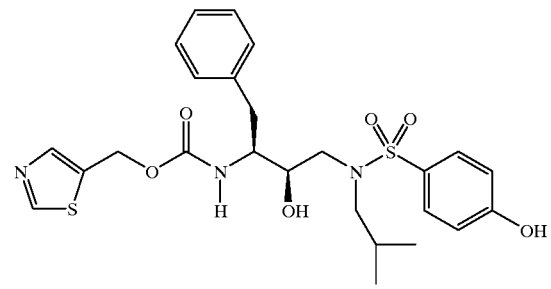

To a solution of 482 mg (4.3 mmol) of 5-(hydroxymethyl) thiazole in 48 mL of anhydrous acetonitrile, is added 1.2 g (4.7 mmol) of N,N'-disuccinimidyl carbonate and then 0.94 mL of pyridine. After stirring for about 4 to 5 hours, 1.53 g (3.92 mmol) of 2R-hydroxy-3-[(2-methylpropyl) (4-hydroxyphenyl)sulfonyl]amino-1S-(phenylmethyl) propylamine is added. After stirring for approximately 19 hours, the solvent would be removed under reduced pressure, theyl acetate added, washed with 5% citric acid, saturated sodium bicarbonate, brine, dried over anhydrous magnesium sulfate, filtered and concentrated to afford crude product. The desired carbamic acid, [2R-hydroxy-3-[[(4-hydroxyphenyl)sulfonyl](2-methylpropyl)amino]-1S-(phenylmethyl)pro,5-(thiazolyl)methyl ester could be isolated in pure form through chromatography on silica gel using 50–100% ethyl acetate/hexane as eluent.

EXAMPLE 18

Following the procedures of Examples 1–16, the compounds shown in Tables 3, 5A and 5B were prepared and in Tables 4 through 17 can be prepared.

TABLE 3

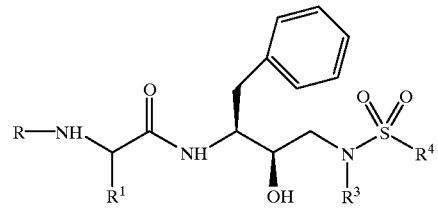

| Entry No. | R | R¹ | R³ | R⁴ |
|---|---|---|---|---|
| 1 | Cbz | t-Butyl | i-Amyl | Methyl |
| 2 | N,N-Dimethylglycine | t-Butyl | i-Amyl | Methyl |
| 3 | Cbz | i-Propyl | i-Amyl | Phenyl |
| 4 | Cbz | sec-Butyl | i-Amyl | Phenyl |
| 5 | Cbz | $CH_2C(O)NH_2$ | n-Propyl | Phenyl |
| 6 | N-Methylglycine | t-Butyl | i-Amyl | Phenyl |
| 7 | Cbz | t-Butyl | i-Butyl | Phenyl |
| 8 | N,N-Dimethylglycine | t-Butyl | i-Amyl | Phenyl |
| 9 | N-Methylglycine | t-Butyl | i-Amyl | Phenyl |
| 10 | N,N-Dimethylglycine | t-Butyl | i-Butyl | (4-OCH₃) Phenyl |
| 11 | N-Methylglycine | t-Butyl | i-Butyl | (4-OCH₃) Phenyl |

TABLE 4

| Entry No. | R | R³ | R⁴ |
|---|---|---|---|
| 1 | Cbz[a] | CH₃ | n-Butyl |
| 2 | Cbz | i-Butyl | CH₃ |
| 3 | Cbz | i-Butyl | n-Butyl |
| 4 | Q[b] | i-Butyl | n-Butyl |
| 5 | Cbz | i-Propyl | n-Butyl |
| 6 | Q | i-Propyl | n-Butyl |
| 7 | Cbz | C₆H₅ | n-Butyl |
| 8 | Cbz | —CH₂-cyclohexyl | n-Butyl |
| 9 | Cbz | —CH₂-phenyl | n-Butyl |
| 10 | Q | —CH₂-phenyl | n-Butyl |
| 11 | Cbz | cyclohexyl | n-Butyl |
| 12 | Cbz | i-Butyl | n-Propyl |
| 13 | Cbz | i-Butyl | —CH₂CH(CH₃)₂ |
| 14 | Cbz | (R)—CH(CH₃)-phenyl | n-Butyl |
| 15 | Cbz | CH₂-cyclohexyl | i-Propyl |
| 16 | Cbz | —CH₂-cyclohexyl | —CH₂CH₂CH(CH₃)₂ |
| 17 | Cbz | i-Butyl | —CH₂CH₃ |
| 18 | Cbz | i-Butyl | —CH(CH₃)₂ |
| 19 | Cbz | i-Butyl | cyclohexyl |
| 20 | Q | -Butyl | cyclohexyl |

TABLE 4-continued

[Structure: R-NH-CH(CH2CONH2)-C(=O)-NH-CH(CH2C6H5)-CH(OH)-CH2-N(R3)-S(=O)2-R4]

| Entry No. | R | R3 | R4 |
|---|---|---|---|
| 21 | Cbz | —CH2-cyclohexyl | —(CH2)2CH(CH3)2 |
| 22 | Cbz | (CH2)2CH(CH3)2 | —CH(CH3)2 |
| 23 | Q | i-Butyl | —CH(CH3)2 |
| 24 | Cbz | i-Butyl | —C(CH3)3 |
| 25 | Q | i-Butyl | —C(CH3)3 |
| 26 | Cbz | —CH2-(2-naphthyl) | —C(CH3)3 |
| 27 | Q | —CH2-(2-naphthyl) | —C(CH3)3 |
| 28 | Cbz | —(CH2)2CH(CH3)2 | —C(CH3)3 |
| 29 | Q | —(CH2)2CH(CH3)2 | —C(CH3)3 |
| 30 | Cbz | —CH2C6H5 | —C(CH3)3 |
| 31 | Q | —CH2C6H5 | —C(CH3)3 |
| 32 | Cbz | —(CH2)2C6H5 | —C(CH3)3 |
| 33 | Cbz | —(CH2)2C6H5 | —C(CH3)3 |
| 34 | Cbz | n-Butyl | —C(CH3)3 |
| 35 | Cbz | n-Pentyl | —C(CH3)3 |
| 36 | Cbz | n-Hexyl | —C(CH3)3 |
| 37 | Cbz | —CH2C6H5 | —C(CH3)3 |
| 38 | Cbz | —CH2C(CH3)3 | —C(CH3)3 |
| 39 | Q | —CH2C(CH3)3 | —C(CH3)3 |
| 40 | Cbz | —CH2CH2-morpholino | —C(CH3)3 |
| 41 | Cbz | —CH2C6H5OCH3(para) | —C(CH3)3 |
| 42 | Cbz | —CH2-(3-pyridyl) | —C(CH3)3 |
| 43 | Cbz | —CH2-(4-pyridyl) | —C(CH3)3 |
| 44 | Cbz | —(CH2)2C(CH3)3 | —C(CH3)3 |
| 45 | Q | —(CH2)2C(CH3)3 | —C(CH3)3 |
| 46 | Cbz | —(CH2)4OH | —C(CH3)3 |
| 47 | Q | —(CH2)4OH | —C(CH3)3 |

TABLE 4-continued
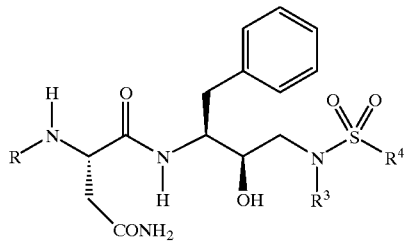
| Entry No. | R | R³ | R⁴ |
|---|---|---|---|
| 48 | Q | —CH₂—C₆H₄—F | —C(CH₃)₃ |
| 49 | Q | —CH₂-(4-pyridyl) | —C(CH₃)₃ |
| 50 | Cbz | —CH₂CH(CH₃)₂ | —C₆H₅ |
| 51 | 2-acetylquinoline | —CH₂CH(CH₃)₂ | —C₆H₅ |
| 52 | (CH₃)₂N-CH₂-C(O)- | —CH₂CH(CH₃)₂ | —C₆H₅ |
| 53 | (pyrimidin-2-ylthio)-CH₂-C(O)- | —CH₂CH(CH₃)₂ | —C₆H₅ |
| 54 | 2-acetylbenzofuran | —CH₂CH(CH₃)₂ | —C₆H₅ |
| 55 | CH₃-C(O)- | —CH₂CH(CH₃)₂ | —C₆H₅ |
| 56 | 5-acetylbenzimidazole | —CH₂CH(CH₃)₂ | —C₆H₅ |
| 57 | 2-acetylpyridine | —CH₂CH(CH₃)₂ | —C₆H₅ |

TABLE 4-continued
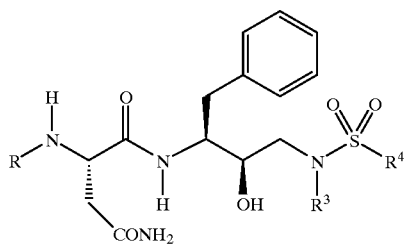
| Entry No. | R | R³ | R⁴ |
|---|---|---|---|
| 58 | 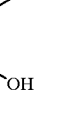 | —CH₂CH(CH₃)₂ | —C₆H₅ |
| 59 |  | —CH₂CH(CH₃)₂ | —C₆H₅ |
| 60 | 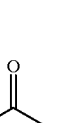 | —CH₂CH(CH₃)₂ | —C₆H₅ |
| 61 |  | —CH₂CH(CH₃)₂ | —C₆H₅ |
| 62 | 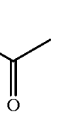 | —CH₂CH(CH₃)₂ | —C₆H₅ |
| 63 | 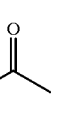 | —CH₂CH(CH₃)₂ | —C₆H₅ |
| 64 | 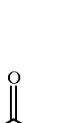 | —CH₂CH(CH₃)₂ | —C₆H₅ |

TABLE 4-continued
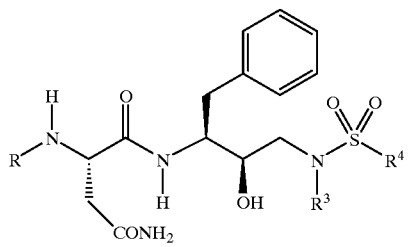
| Entry No. | R | R³ | R⁴ |
|---|---|---|---|
| 65 | 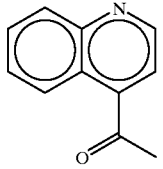 | —CH₂CH(CH₃)₂ | —C₆H₅ |
| 66 | 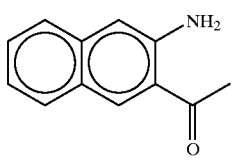 | —CH₂CH(CH₃)₂ | —C₆H₅ |
| 67 | 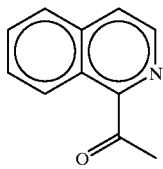 | —CH₂CH(CH₃)₂ | —C₆H₅ |
| 68 | 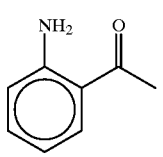 | —CH₂CH(CH₃)₂ | —C₆H₅ |
| 69 | 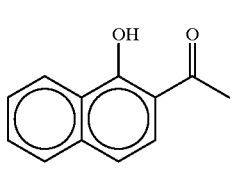 | —CH₂CH(CH₃)₂ | —C₆H₅ |
| 70 | Q | —CH₂Ph | —Ph |
| 71 | Q | 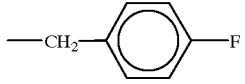 | —Ph |
| 72 | Q | 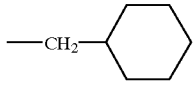 | —Ph |
| 73 | Q | 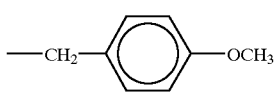 | —Ph |

TABLE 4-continued

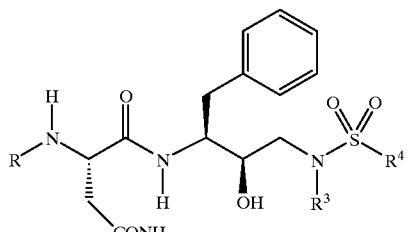

| Entry No. | R | R³ | R⁴ |
|---|---|---|---|
| 74 | Q | 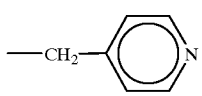 —CH₂-(4-pyridyl) | —Ph |
| 75 | Q | 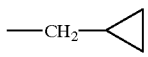 —CH₂-cyclopropyl | —Ph |
| 76 | Q | —CH₂CH=CH₂ | —Ph |
| 77 | Q |  phenyl | —Ph |
| 78 | Q | 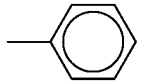 cyclohexyl | —Ph |
| 79 | Q | —CH₂CH₂Ph | —Ph |
| 80 | Q | —CH₂CH₂CH₂CH₂OH | —Ph |
| 81 | Q | —CH₂CH₂N(CH₃)₂ | —Ph |
| 82 | Q | 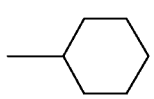 —CH₂CH₂-morpholine | —Ph |
| 83 | Q | —CH₃ | —Ph |
| 84 | Q | —CH₂CH₂CH₂SCH₃ | —Ph |
| 85 | Q | —CH₂CH₂CH₂S(O)₂CH₃ | —Ph |
| 86 | Q | —CH₂CH₂CH₂CH(CH₃)₂ | 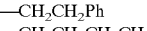 phenyl |
| 87 | Q | —CH₂CH₂CH(CH₃)₂ | 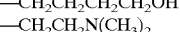 —CH₂-phenyl |
| 88 | Q | —CH₂CH₂CH(CH₃)₂ | —CH₂CH₂CH₃ |
| 89 | Q | —CH₂CH₂CH₂CH(CH₃)₂ | —CH₃ |
| 90 | Q | —CH₂CH₂CH(CH₃)₂ |  4-fluorophenyl |
| 91 | Q | —CH₂CH₂CH(CH₃)₂ | 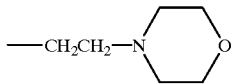 naphthyl |

TABLE 4-continued
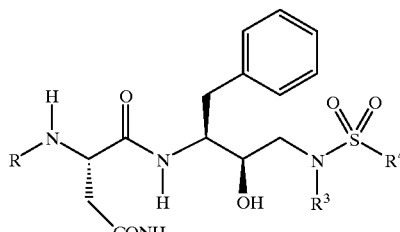
| Entry No. | R | R³ | R⁴ |
|---|---|---|---|
| 92 | Q | —CH₂CH₂CH(CH₃)₂ | 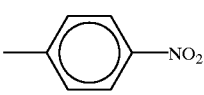 4-NO₂-C₆H₄— |
| 93 | Q | —CH₂CH₂CH(CH₃)₂ | 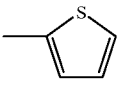 2-thienyl |
| 94 | Q | —CH₂CH₂CH(CH₃)₂ | 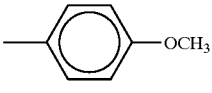 4-OCH₃-C₆H₄— |
| 95 | Q | —CH₂CH₂CH(CH₃)₂ | 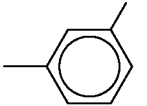 3-NO₂-C₆H₄— |
| 96 | Q | —CH₂CH₂CH(CH₃)₂ | 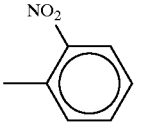 2-NO₂-C₆H₄— |
| 97 | Q | —CH₂CH₂CH(CH₃)₂ | 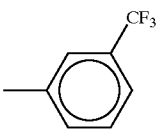 3-CF₃-C₆H₄— |
| 98 | Q | —CH₂CH₂CH(CH₃)₂ | 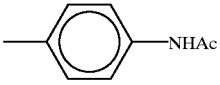 4-NHAc-C₆H₄— |
| 99 | Q | —CH₂CH₂CH(CH₃)₂ |  4-Cl-C₆H₄— |
| 100 | Q | —CH₂CH₂CH(CH₃)₂ | 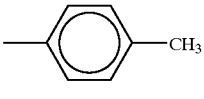 4-CH₃-C₆H₄— |
| 101 | Q | —CH₂CH₂CH(CH₃)₂ | 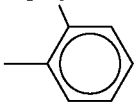 2-CO₂CH₃-C₆H₄— |

TABLE 4-continued

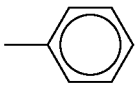

| Entry No. | R | R³ | R⁴ |
|---|---|---|---|
| 102 | Q | —CH₂CH₂CH(CH₃)₂ |  phenyl |
| 103 | Q | —CH₂CH(CH₃)₂ | 4-F-phenyl |
| 104 | Q | —CH₂CH(CH₃)₂ | 4-NHAc-phenyl |
| 105 | Q | —CH₂CH(CH₃)₂ | 4-CH₃-phenyl |
| 106 | Q | —CH₂CH₂CH₃ | 4-OCH₃-phenyl |
| 107 | Q | —CH₂CH₂CH₂CH₃ | 4-OCH₃-phenyl |

ᵃbenzyloxycarbonyl
ᵇ2-quinolinylcarbonyl

TABLE 5

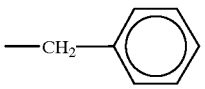

| Entry | A | R³ | R⁴ |
|---|---|---|---|
| 1 | Cbz-Val | i-amyl | —C₆H₅ |
| 2 | Cbz-Leu | i-amyl | —C₆H₅ |
| 3 | Cbz-Ile | i-amyl | —C₆H₅ |
| 4 | Ac-D-homo-Phe | i-Bu | methyl |
| 5 | Qui-Orn(g-Cbz) | —CH₂-phenyl | —C₆H₅ |
| 6 | Cbz-Asn | —CH₂CH=CH₂ | —C₆H₅ |

TABLE 5-continued

[Structure: A-NH-CH(CH2Ph)-CH(OH)-CH2-N(R3)-SO2-R4]

| Entry | A | R³ | R⁴ |
|---|---|---|---|
| 7 | Acetyl-t-BuGly | i-amyl | —C₆H₅ |
| 8 | Acetyl-Phe | i-amyl | —C₆H₅ |
| 9 | Acetyl-Ile | i-amyl | —C₆H₅ |
| 10 | Acetyl-Leu | i-amyl | —C₆H₅ |
| 11 | Acetyl-His | i-amyl | —C₆H₅ |
| 12 | Acetyl-Thr | i-amyl | —C₆H₅ |
| 13 | Acetyl-NHCH(C(CH₃)₂(SCH₃))C(O)— | i-amyl | —C₆H₅ |
| 14 | Cbz-Asn | i-amyl | —C₆H₅ |
| 15 | Cbz-Ala | i-amyl | —C₆H₅ |
| 16 | (N,N-dimethylglycinyl)Val | i-amyl | —C₆H₅ |
| 17 | (N-methylglycinyl)Val | i-amyl | —C₆H₅ |
| 18 | (N,N-dimethylglycinyl)Ile | i-amyl | —C₆H₅ |
| 19 | (N-methylglycinyl)Ile | i-amyl | —C₆H₅ |
| 20 | Cbz-Ala | i-amyl | —C₆H₅ |
| 21 | Cbz-beta-cyanoAla | i-amyl | —C₆H₅ |
| 22 | Cbz-t-BuGly | i-amyl | —C₆H₅ |
| 23 | Q-t-BuGly | i-amyl | —C₆H₅ |
| 24 | Q-SCH₃Cys | i-amyl | —C₆H₅ |
| 25 | Cbz-SCH₃Cys | i-amyl | —C₆H₅ |
| 26 | Q-Asp | i-amyl | —C₆H₅ |
| 27 | Cbz-(NHCH(C(CH₃)₂(SCH₃))C(O)— | i-amyl | —C₆H₅ |
| 28 | Cbz-EtGly | i-amyl | —C₆H₅ |
| 29 | Cbz-PrGly | i-amyl | —C₆H₅ |
| 30 | Cbz-Thr | i-amyl | —C₆H₅ |
| 31 | Q-Phe | i-amyl | —C₆H₅ |
| 32 | Cbz-Phe | i-amyl | —C₆H₅ |
| 33 | CH2=CHCH2—O—C(O)— | i-Butyl | —C₆H₄-OCH₃ (p-methoxyphenyl) |

TABLE 5A

[Structure: R7-C(O)-NH-CH(CH2Ph)-CH(OH)-CH2-N(R3)-SO2-R4]

| Entry | R³ | R⁴ | R⁷ | MOL FORM | CALC M + H | FOUND |
|---|---|---|---|---|---|---|
| 1 | —CH₂CH(CH₃)₂ (isobutyl) | p-methoxyphenyl | cyclopentyl | C₂₇H₃₈N₂O₅S | 503.2661 | 503.2624 |

TABLE 5A-continued

| Entry | R³ | R⁴ | R⁷ | MOL FORM | CALC M + H | FOUND |
|---|---|---|---|---|---|---|
| 2 | | | cyclohexyl-CH₂- | $C_{28}H_{40}N_2O_5S$ | 517.2736 | 517.2777 |
| 3 | | | cycloheptyl-CH₂- | $C_{29}H_{42}N_2O_5S$ | 531.2893 | 531.2916 |
| 4 | | | tetrahydronaphthyl-CH₂- | $C_{32}H_{40}N_2O_5S$ | 565.2736 | 565.2731 |
| 5 | | | 5-methylindol-yl | $C_{30}H_{35}N_3O_5S$ | 550.2376 | 550.2427 |
| 6 | -CH₂CH(CH₃)₂ | 4-CH₃O-C₆H₄- | 2,4,5-trimethylphenyl | $C_{30}H_{38}N_2O_5S$ | 539 (M + H) | 539 |
| 7 | | | 2,4-dimethylphenyl | $C_{29}H_{36}N_2O_5S$ | ? | ? |
| 8 | | | | $C_{30}H_{38}N_2O_5S$ | 539.2580 (M + H) | 539.2591 |
| 9 | -CH₂CH(CH₃)₂ | 4-CH₃O-C₆H₄- | pyridin-3-yl-CH₂- | $C_{27}H_{33}N_3O_5S$ | 512.2219 | 512.2271 |
| 10 | | | 2,3-dimethylpyridin-yl | $C_{28}H_{35}N_3O_5S$ | 526.2376 | 526.2388 |

TABLE 5A-continued

[Structure: R7-C(=O)-NH-CH(CH2-Ph)-CH(OH)-CH2-N(R3)-S(=O)2-R4]

| Entry | R³ | R⁴ | R⁷ | MOL FORM | CALC M + H | FOUND |
|---|---|---|---|---|---|---|
| 11 | | | 4-pyridyl-CH2- | C27H33N3O5S | 512.2219 | 512.2287 |
| 12 | | | 2-Cl-C6H4-CH2- | C28H33N2O5ClS | 545.1877 | 545.1887 |
| 13 | | | 2-(CH2CH3)-C6H4-CH2- | C30H38N2O5S | 539.2580 | 539.2592 |
| 14 | | | 2-(CH2(CH3)2)-C6H4-CH2- | C31H40N2O5S | 553.2736 | 553.2714 |
| 15 | | | 2,3-(CH3)2-C6H3-CH2- | C30H38N2O5S | 539.2580 | 539.2632 |
| 16 | | | 2,3,(CH3)2-C6H3-CH2- (H3C, CH3 shown) | C30H38N2O5S | 539 (M + H) | 539 |
| 17 | CH2CH(CH3)CH3 | 4-OCH3-C6H4- | 2-(SO2CH3)-C6H4-CH2- | C29H36N2O7S2 | 589.2042 (M + H) | 589.2086 |
| 18 | | | 3-(H3CSO2)-C6H4-CH2- | C29H36N2O7S2 | 595.2124 (M + Li) | 595.2103 |

TABLE 5A-continued

Structure: R7-C(=O)-NH-CH(CH2Ph)-CH(OH)-CH2-N(R3)-SO2-R4

| Entry | R³ | R⁴ | R⁷ | MOL FORM | CALC M + H | FOUND |
|---|---|---|---|---|---|---|
| 19 | | | 4-(H₃CSO₂)-C₆H₄- | C₂₉H₃₆N₂O₇S₂ | 595.2124 (M + Li) | 595.2191 |
| 20 | | | 2-methyl-(CH₂SO₂CH₃)-phenyl | C₃₀H₃₈N₂O₇S₂ | 609.2281 (M + Li) | 609.2313 |
| 21 | | | 3-methyl-(H₃CSO₂CH₂)-phenyl | C₃₀H₃₈N₂O₇S₂ | 603.2199 (M + H) | 603.2247 |
| 22 | | | 4-methyl-(H₃CSO₂CH₂)-phenyl | C₃₀H₃₈N₂O₇S₂ | 603.2199 (M + H) | 603.2266 |
| 23 | CH₂CH(CH₃)CH₃ (isobutyl) | phenyl | phenyl | | | |
| 24 | CH₂CH(CH₃)₂ (isobutyl) | phenyl | phenyl | C₂₇H₃₂N₂O₄S | 481.2161 | 481.2213 |
| 25 | CH₂CH(CH₃)₂ | 4-OCH₃-phenyl | phenyl | C₂₈H₃₅N₂O₅S | 511.2267 | 511.2319 |
| 26 | CH₂CH(CH₃)₂ | 4-OCH₃-phenyl | 2-methylphenyl | C₂₉H₃₆N₂O₅S | 525.2423 | 525.2469 |
| 27 | | | 3-methylphenyl | C₂₉H₃₆N₂O₅S | 525.2428 | 525.2464 |

TABLE 5A-continued
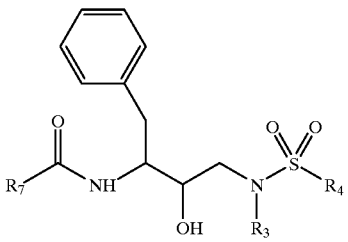
| | | | | MASS MEASUREMENT | | |
| --- | --- | --- | --- | --- | --- | --- |
| Entry | R³ | R⁴ | R⁷ | MOL FORM | CALC M + H | FOUND |
| 28 | | | 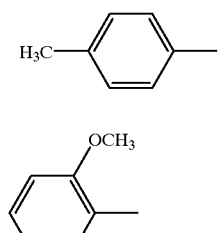 | $C_{29}H_{36}N_2O_5S$ | 525.2423 | 525.2432 |
| 29 | | | 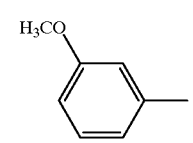 | $C_{29}H_{36}N_2O_6S$ | 541.2372 | 541.2332 |
| 30 | | | 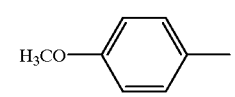 | $C_{29}H_{36}N_2O_6S$ | 541.2372 | 541.2355 |
| 31 | | | 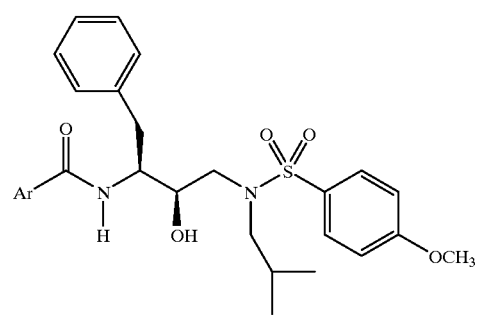 | $C_{29}H_{36}N_2O_6S$ | 541.2372 | 541.2329 |
TABLE 5B
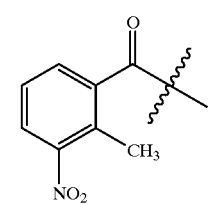
| Entry | A | Molecular Formula | Mass Spectrum |
| --- | --- | --- | --- |
| | | $C_{29}H_{35}N_3O_7S$ | 576 (M + Li) |

TABLE 5B-continued

[Structure: Ar-C(=O)-NH-CH(CH2Ph)-CH(OH)-CH2-N(iBu)-SO2-C6H4-OCH3]

| Entry | A | Molecular Formula | Mass Spectrum |
|---|---|---|---|
| | 3-amino-2-methylbenzoyl | $C_{29}H_{37}N_3O_5S$ | 540 (M + H) |
| | 3-dimethylamino-2-methylbenzoyl | $C_{31}H_{41}N_3O_5S$ | 568 (M + H) |
| | 4-nitro-2-methylbenzoyl | $C_{29}H_{35}N_3O_7S$ | 570 (M + H) |
| | 4-amino-2-methylbenzoyl | $C_{29}H_{37}N_3O_5S$ | 540 (M + H) |
| | 4-dimethylamino-2-methylbenzoyl | $C_{31}H_{41}N_3O_5S$ | 568 (M + H) |
| | 5-nitro-2-methylbenzoyl | $C_{29}H_{35}N_3O_7S$ | 570 (M + H) |

TABLE 5B-continued

| Entry | A | Molecular Formula | Mass Spectrum |
|---|---|---|---|
| | 5-amino-2-methylbenzoyl group (H₂N-, CH₃-substituted phenyl ketone) | $C_{29}H_{37}N_3O_5S$ | 546 (M + Li) |
| | 5-(dimethylamino)-2-methylbenzoyl group (Me₂N-, CH₃-substituted phenyl ketone) | $C_{31}H_{41}N_3O_5S$ | 574 (M + Li) |

TABLE 6

| Entry | R¹ |
|---|---|
| 1 | $CH_2SO_2CH_3$ |
| 2 | (R)—CH(OH)CH₃ |
| 3 | CH(CH₃)₂ |
| 4 | (R,S)CH₂SOCH₃ |
| 5 | $CH_2SO_2NH_2$ |
| 6 | CH₂SCH₃ |
| 7 | CH₂CH(CH₃)₂ |
| 8 | CH₂CH₂C(O)NH₂ |
| 9 | (S)—CH(OH)CH₃ |
| 10 | —CH₂C≡C—H |

TABLE 7

| Entry | R² | A |
|---|---|---|
| 1 | n-Bu | Cbz-Asn |
| 2 | cyclohexylmethyl | Cbz-Asn |
| 3 | n-Bu | Boc |
| 4 | n-Bu | Cbz |
| 5 | C₆H₅CH₂ | Boc |
| 6 | P-F-C₆H₅CH₂ | Cbz |
| 7 | C₆H₅CH₂ | benzoyl |
| 8 | cyclohexylmethyl | Cbz |
| 9 | n-Bu | Q-Asn |
| 10 | cyclohexylmethyl | Q-Asn |
| 11 | C₆H₅CH₂ | Cbz-Ile |
| 12 | C₆H₅CH₂ | Q-Ile |
| 13 | P-F-C₆H₅CH₂ | Cbz-t-BuGly |
| 14 | C₆H₅CH₂ | Q-t-BuGly |
| 15 | C₆H₅CH₂ | Cbz-Val |
| 16 | C₆H₅CH₂ | Q-Val |
| 17 | 2-naphthylmethyl | Cbz-Asn |
| 18 | 2-naphthylmethyl | Q-Asn |
| 19 | 2-naphthylmethyl | Cbz |
| 20 | n-Bu | Cbz-Val |
| 21 | n-Bu | Q-Val |
| 22 | n-Bu | Q-Ile |
| 23 | n-Bu | Cbz-t-BuGly |
| 24 | n-BU | Q-t-BuGly |

TABLE 7-continued
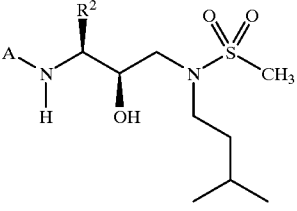
| Entry | R² | A |
|---|---|---|
| 25 | p-F(C₆H₄)CH₂ | Q-Asn |
| 26 | p-F(C₆H₄)CH₂ | Cbz |
| 27 | p-F(C₆H₄)CH₂ | Cbz-Asn |
| 28 | C₆H₅CH₂ | Cbz-propargylglycine |
| 29 | C₆H₅CH₂ | Q-propargylglycine |
| 30 | C₆H₅CH₂ | acetylpropargylglycine |
TABLE 8
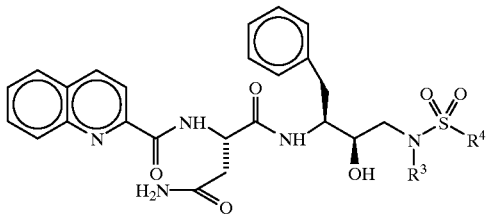
| Entry | R³ | R⁴ |
|---|---|---|
| 1 | —CH₂CH(CH₃)₂ | —C(CH₃)₂ |
TABLE 8-continued
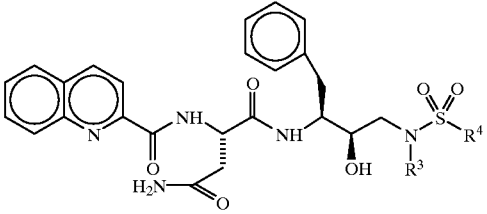
| Entry | R³ | R⁴ |
|---|---|---|
| 2 | —CH₂CH₂CH(CH₃)₂ | 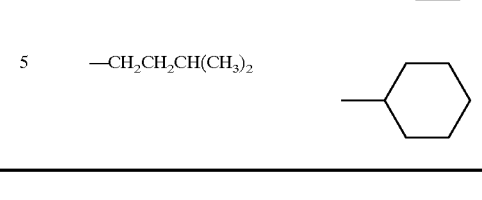 |
| 3 | —CH₂CH₂CH(CH₃)₂ | |
| 4 | —CH₂CH₂CH(CH₃)₂ | |
| 5 | —CH₂CH₂CH(CH₃)₂ | |
TABLE 9
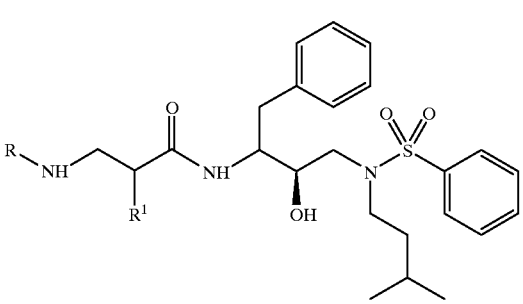
| Entry | R | R¹ |
|---|---|---|
| 1 | 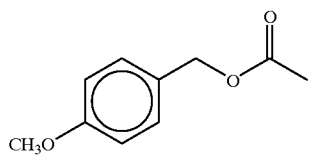 | —CH₃ |

TABLE 9-continued
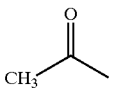
| Entry | R | R¹ |
|---|---|---|
| 2 | 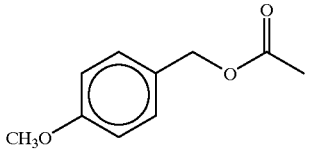 | —CH₃ |
| 3 | 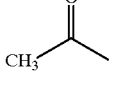 | —CH(CH₃)₂ |
| 4 | 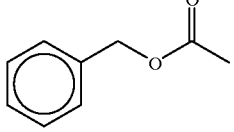 | —CH(CH₃)₂ |
| 5 | 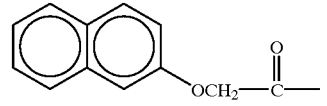 | —C(CH₃)₃ |
| 6 | 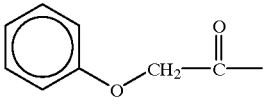 | —CH₃ |
| 7 | 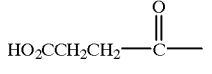 | —CH₃ |
| 8 | 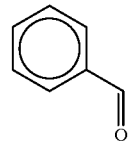 | —CH₃ |
| 9 | 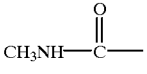 | —CH₃ |
| 10 | 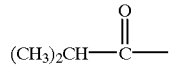 | —CH₃ |
| 11 | (CH₃)₂CH—C(=O)— | —CH₃ |

TABLE 9-continued

[Structure shown: R-NH-CH(R¹)-C(=O)-NH-CH(CH₂-phenyl)-CH(OH)-CH₂-N(SO₂-phenyl)(CH₂CH₂CH(CH₃)₂)]

| Entry | R | R¹ |
|---|---|---|
| 12 | CH₃OCH₂-C(=O)- | —CH₃ |
| 13 | (CH₃)₂NCH₂-C(=O)- | —CH₃ |
| 14 | CH₃CH(OH)-C(=O)- | —CH₃ |
| 15 | [Structure: 4-methoxybenzyl-OC(=O)NH-cyclohexyl-C(=O)-NH-CH(CH₂Ph)-CH(OH)-CH₂-N(SO₂Ph)(isopentyl)] | |
| 16 | [Structure: benzyl-OC(=O)NH-cyclobutyl-C(=O)-NH-CH(CH₂Ph)-CH(OH)-CH₂-N(SO₂CH₃)(isopentyl)] | |

TABLE 10

[Structure: R-NH-C(R1")(R1')-C(R1)(H)-C(=O)-NH-CH(CH2-Ph)-CH(OH)-CH2-N(SO2Ph)(CH2CH2CH(CH3)2)]

| Entry | R¹ | R¹' | R¹" | R |
|-------|----|----|-----|---|
| 1 | H | H | H | C6H5-CH2-O-C(=O)- |
| 2 | H | H | H | CH3-C(=O)- |
| 3 | H | CH3 | H | 4-CH3O-C6H4-CH2-O-C(=O)- |
| 4 | H | CH3 | CH3 | C6H5-CH2-O-C(=O)- |
| 5 | H | H | CO2CH3 | C6H5-CH2-O-C(=O)- |
| 6 | H | H | H | 4-CH3O-C6H4-CH2-O-C(=O)- |
| 7 | H | H | H | H2N-C(=O)- |
| 8 | H | H | CONH2 | Cbz |
| 9 | H | H | CONH2 | 2-quinolinylcarbonyl |

TABLE 11

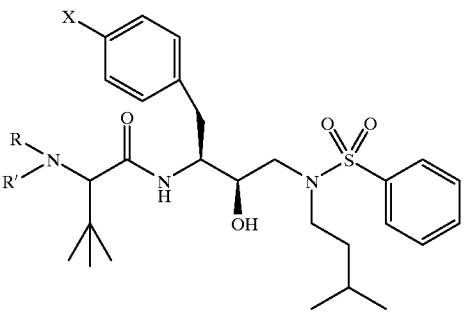

| Entry | R | R' | X |
|---|---|---|---|
| 1 | R=H | R'=H | X=H |
| 2 | R=Me | R'=Me | X=H |
| 3 | R=H | R'=Me | X=H |
| 4 | R=Me | R'=Ne | X=F |
| 5 | R=H | R'=Me | X=F |
| 6 | R=Cbz | R'=Me | X=H |
| 7 | R=H | R'=Bz | X=H |
| 8 | R+R'=pyrrole | | X=H |

TABLE 12

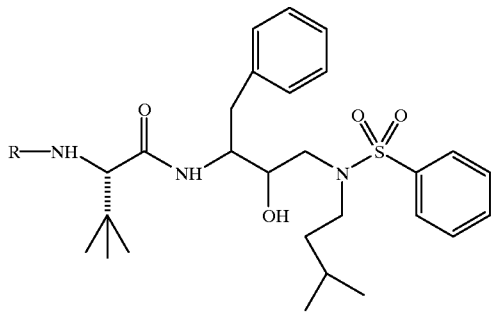

| Entry | Acyl Group (R) |
|---|---|
| 1 | benzyloxycarbonyl |
| 2 | tert-butoxycarbonyl |

TABLE 12-continued

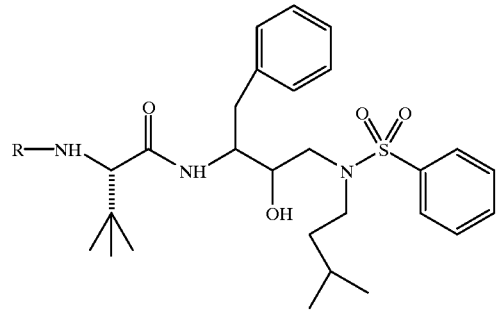

| Entry | Acyl Group (R) |
|---|---|
| 3 | acetyl |
| 4 | 2-quinoylcarbonyl |
| 5 | phenoxyacetyl |
| 6 | benzoyl |
| 7 | methyloxaloyl |
| 8 | pivaloyl |
| 9 | trifluoracetyl |
| 10 | bromoacetyl |
| 11 | hydroxyacetyl |
| 12 | morpholinylacetyl |
| 13 | N,N-dimethylaminoacetyl |
| 14 | N-benzylaminoacetyl |
| 15 | N-phenylaminoacetyl |
| 16 | N-benzyl-N-methylaminoacetyl |
| 17 | N-methyl-N-(2-hydroxyethyl)aminoacetyl |
| 18 | N-methylcarbamoyl |
| 19 | 3-methylbutyryl |
| 20 | N-isobutylcarbamoyl |
| 21 | succinoyl (3-carboxypropionyl) |
| 22 | carbamoyl |
| 23 | N-(2-indanyl)aminoacetyl |

TABLE 13

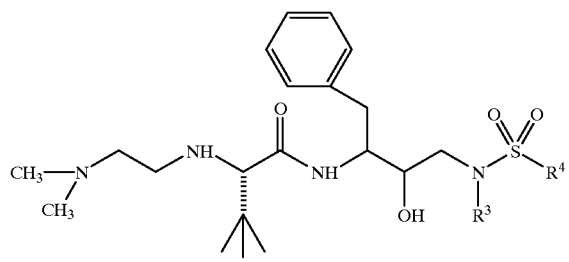

| Entry | $R^3$ | $R^4$ |
|---|---|---|
| 1 | —$CH_3$ | —n-Butyl |
| 2 | —i-Butyl | —$CH_3$ |
| 3 | —i-Butyl | —n-Butyl |
| 4 | —i-Propyl | —n-Butyl |
| 5 | —$C_6H_5$ | —n-Butyl |

TABLE 13-continued

[Structure: CH₃(CH₃)N-CH₂CH₂-NH-CH(iPr)-C(=O)-NH-CH(CH₂Ph)-CH(OH)-CH₂-N(R³)-S(=O)₂-R⁴]

| Entry | R³ | R⁴ |
|---|---|---|
| 6 | —CH₂-cyclohexyl | —n-Butyl |
| 7 | —CH₂-phenyl | —n-Butyl |
| 8 | cyclohexyl | —n-Butyl |
| 9 | —i-Butyl | —n-Propyl |
| 10 | —i-Butyl | —CH₂CH(CH₃)₂ |
| 11 | —(R)—CH(CH₃)-phenyl | —n-Butyl |
| 12 | —CH₂-cyclohexyl | —i-Propyl |
| 13 | —CH₂-cyclohexyl | —CH₂CH₂CH(CH₃)₂ |
| 14 | i-Butyl | —CH₂CH₃ |
| 15 | i-Butyl | —CH(CH₃)₂ |
| 16 | i-Butyl | cyclohexyl |
| 17 | —CH₂-cyclohexyl | —(CH₂)₂CH(CH₃)₂ |
| 18 | (CH₂)₂CH(CH₃)₂ | —CH(CH₃)₂ |
| 19 | i-Butyl | —CH(CH₃)₂ |
| 20 | i-Butyl | —C(CH₃)₃ |
| 21 | —CH₂-naphthyl | —C(CH₃)₃ |
| 22 | —(CH₂)₂CH(CH₃)₂ | —C(CH₃)₃ |
| 23 | —CH₂C6H5 | —C(CH₃)₃ |

TABLE 13-continued

| Entry | R³ | R⁴ |
|---|---|---|
| 24 | —(CH₂)₂C₆H₅ | —C(CH₃)₃ |
| 25 | n-Butyl | —C(CH₃)₃ |
| 26 | n-Pentyl | —C(CH₃)₃ |
| 27 | n-Hexyl | —C(CH₃)₃ |
| 28 | —CH₂-C₆H₅ (benzyl) | —C(CH₃)₃ |
| 29 | —CH₂C(CH₃)₃ | —C(CH₃)₃ |
| 30 | —CH₂CH₂-morpholinyl | —C(CH₃)₃ |
| 31 | —CH₂C₆H₅OCH₃(para) | —C(CH₃)₃ |
| 32 | —CH₂-(3-pyridyl) | —C(CH₃)₃ |
| 33 | —CH₂-(4-pyridyl) | —C(CH₃)₃ |
| 34 | —(CH₂)₂C(CH₃)₃ | —C(CH₃)₃ |
| 35 | —(CH₂)₄OH | —C(CH₃)₃ |
| 36 | —CH₂-(4-fluorophenyl) | —C(CH₃)₃ |
| 37 | —CH₂-(4-pyridyl) | —C(CH₃)₃ |
| 38 | —CH₂CH(CH₃)₂ | —C₆H₅ |
| 39 | i-amyl | —CH₂C(CH₃)₃ |
| 40 | cyclohexyl | —CH₂C(CH₃)₃ |
| 41 | CH₃-cyclohexyl | —CH₂C(CH₃)₃ |
| 42 | i-butyl | —CH₂C(CH₃)₃ |
| 43 | —CH₂Ph | —Ph |

TABLE 13-continued
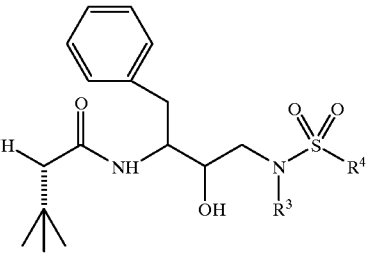
| Entry | R³ | R⁴ |
|---|---|---|
| 44 | 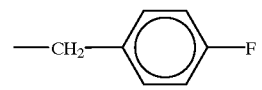 | —Ph |
| 45 | 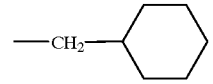 | —Ph |
| 46 | 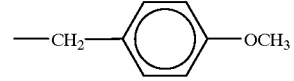 | —Ph |
| 47 | 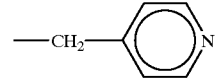 | —Ph |
| 48 | 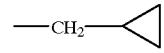 | —Ph |
| 49 | —CH₂CH=CH₂ | —Ph |
| 50 | 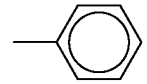 | —Ph |
| 51 | 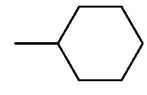 | —Ph |
| 52 | —CH₂CH₂Ph | —Ph |
| 53 | —CH₂CH₂CH₂CH₂OH | —Ph |
| 54 | —CH₂CH₂N(CH₃)₂ | —Ph |
| 55 | 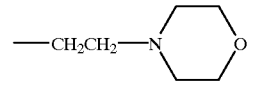 | —Ph |
| 56 | —CH₃ | —Ph |
| 57 | —CH₂CH₂CH₂SCH₃ | —Ph |
| 58 | —CH₂CH₂CH₂S(O)₂CH₃ | —Ph |
| 59 | —CH₂CH₂CH(CH₃)₂ | 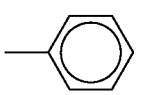 |
| 60 | —CH₂CH₂CH(CH₃)₂ | 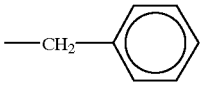 |

TABLE 13-continued
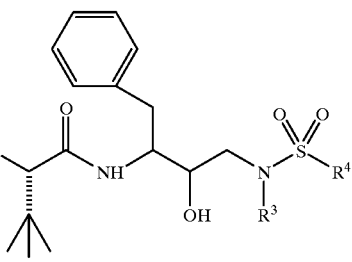
| Entry | R³ | R⁴ |
|---|---|---|
| 61 | —CH₂CH₂CH(CH₃)₂ | —CH₂CH₂CH₃ |
| 62 | —CH₂CH₂CH(CH₃)₂ | —CH₃ |
| 63 | —CH₂CH₂CH(CH₃)₂ |  4-F-C₆H₄— |
| 64 | —CH₂CH₂CH(CH₃)₂ | 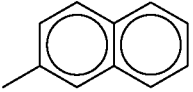 2-naphthyl |
| 65 | —CH₂CH₂CH(CH₃)₂ |  4-NO₂-C₆H₄— |
| 66 | —CH₂CH₂CH(CH₃)₂ | 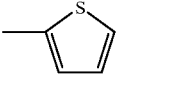 2-thienyl |
| 67 | —CH₂CH₂CH(CH₃)₂ |  4-OCH₃-C₆H₄— |
| 68 | —CH₂CH₂CH(CH₃)₂ | 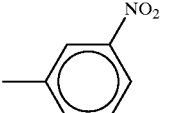 3-NO₂-C₆H₄— |
| 69 | —CH₂CH₂CH(CH₃)₂ | 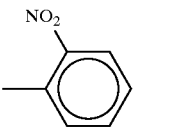 2-NO₂-C₆H₄— |
| 70 | —CH₂CH₂CH(CH₃)₂ | 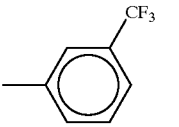 3-CF₃-C₆H₄— |
| 71 | —CH₂CH₂CH(CH₃)₂ |  4-NHAc-C₆H₄— |

TABLE 13-continued
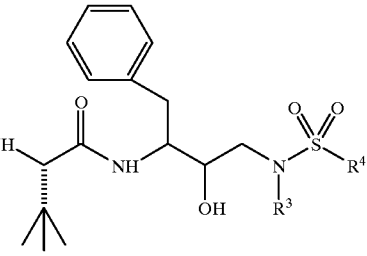
| Entry | R³ | R⁴ |
|---|---|---|
| 72 | —CH₂CH₂CH(CH₃)₂ |  4-Cl-phenyl |
| 73 | —CH₂CH₂CH(CH₃)₂ | 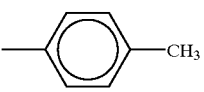 4-CH₃-phenyl |
| 74 | —CH₂CH₂CH(CH₃)₂ | 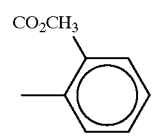 2-CO₂CH₃-phenyl |
| 75 | —CH₂CH(CH₃)₂ | 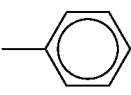 phenyl |
| 76 | —CH₂CH(CH₃)₂ | 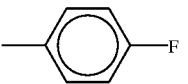 4-F-phenyl |
| 77 | —CH₂CH(CH₃)₂ | 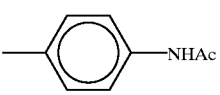 4-NHAc-phenyl |
| 78 | —CH₂CH(CH₃)₂ | 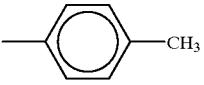 4-CH₃-phenyl |
| 79 | —CH₂CH₂CH₃ | 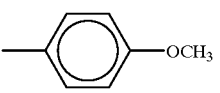 4-OCH₃-phenyl |
| 80 | —CH₂CH₂CH₂CH₃ | 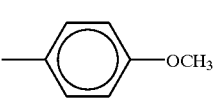 4-OCH₃-phenyl |
ᵃbenzyloxycarbonyl
ᵇ2-quinolinylcarbonyl

TABLE 14
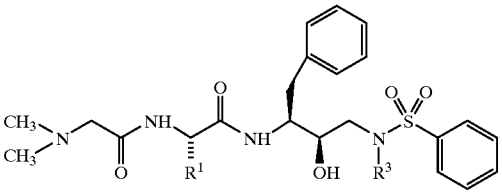
| Entry | R¹ | R³ |
|---|---|---|
| 1 | C(CH₃)₃ | CH₂CH₂CH(CH₃)₂ |
| 2 | CH₂C≡CH | CH₂CH₂CH(CH₃)₂ |
| 3 | C(CH₃)₂(SCH₃) | CH₂CH₂CH(CH₃)₂ |
| 4 | C(CH₃)₂(S[O]CH₃) | CH₂CH₂CH(CH₃)₂ |
| 5 | C(CH₃)₂(S[O]₂CH₃) | CH₂CH₂CH(CH₃)₂ |
| 6 | C(CH₃)₃ | CH₂CH(CH₃)₂ |
| 7 | C(CH₃)₃ | 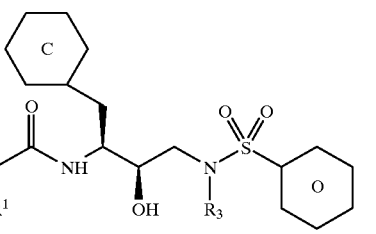 |
| 8 | CH(CH₃)₂ | CH₂CH(CH₃)₂ |
| 9 | CH(CH₂CH₃)(CH₃) | CH₂CH(CH₃)₂ |
TABLE 14A
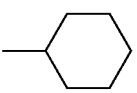
| Entry | R¹ | R³ |
|---|---|---|
| 1 | C(CH₃)SCH₃ | CH₂CH₂CH(CH₃)₂ |

TABLE 15
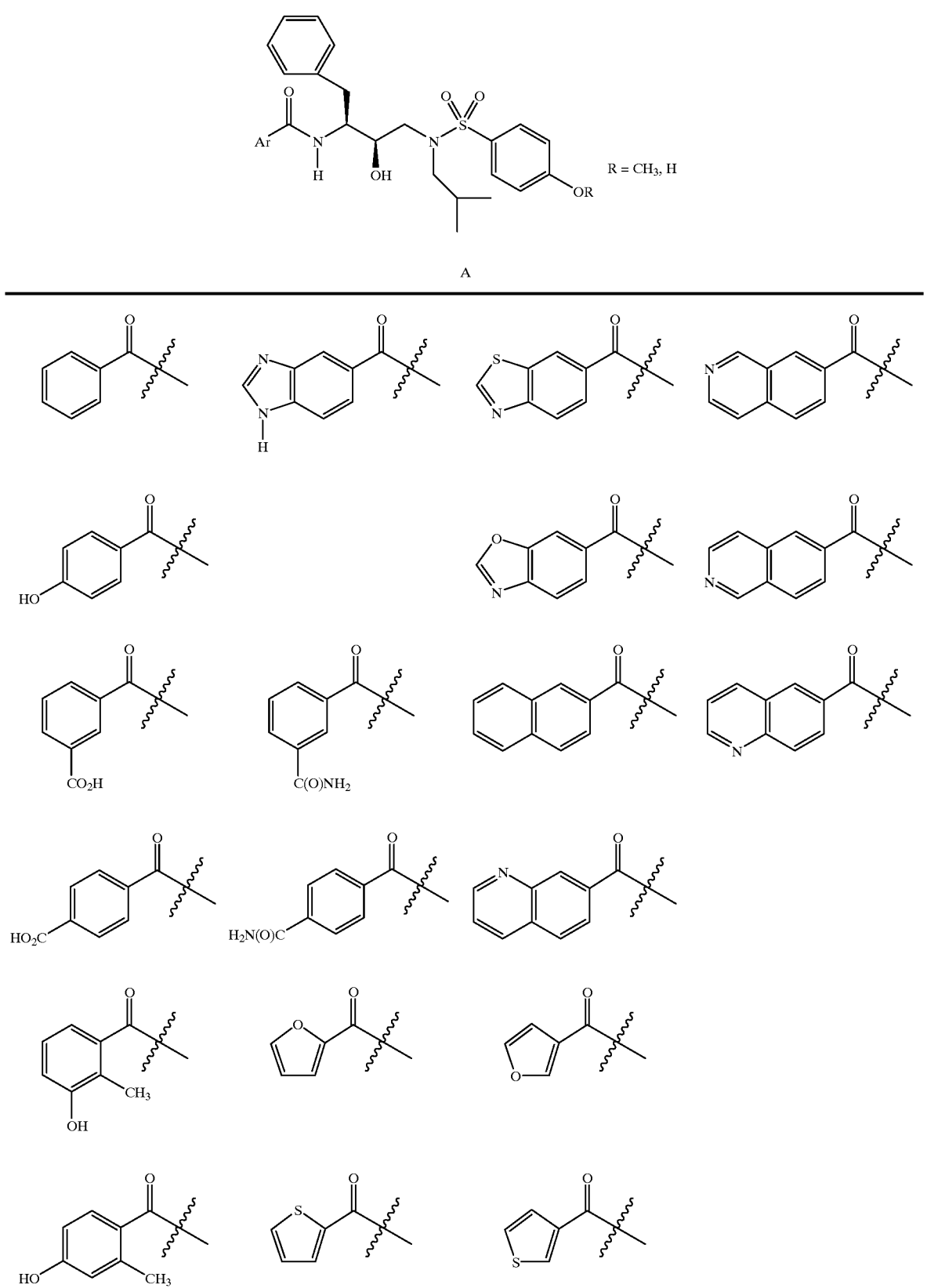

TABLE 15-continued
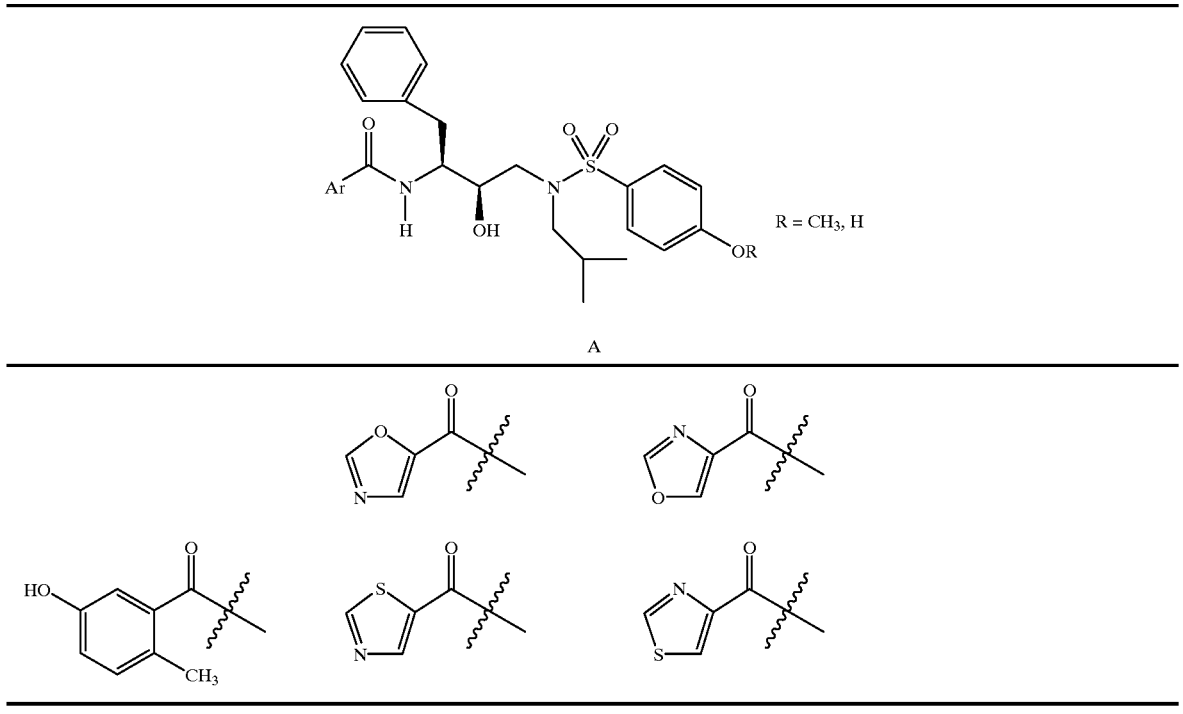
TABLE 16
TABLE 16-continued
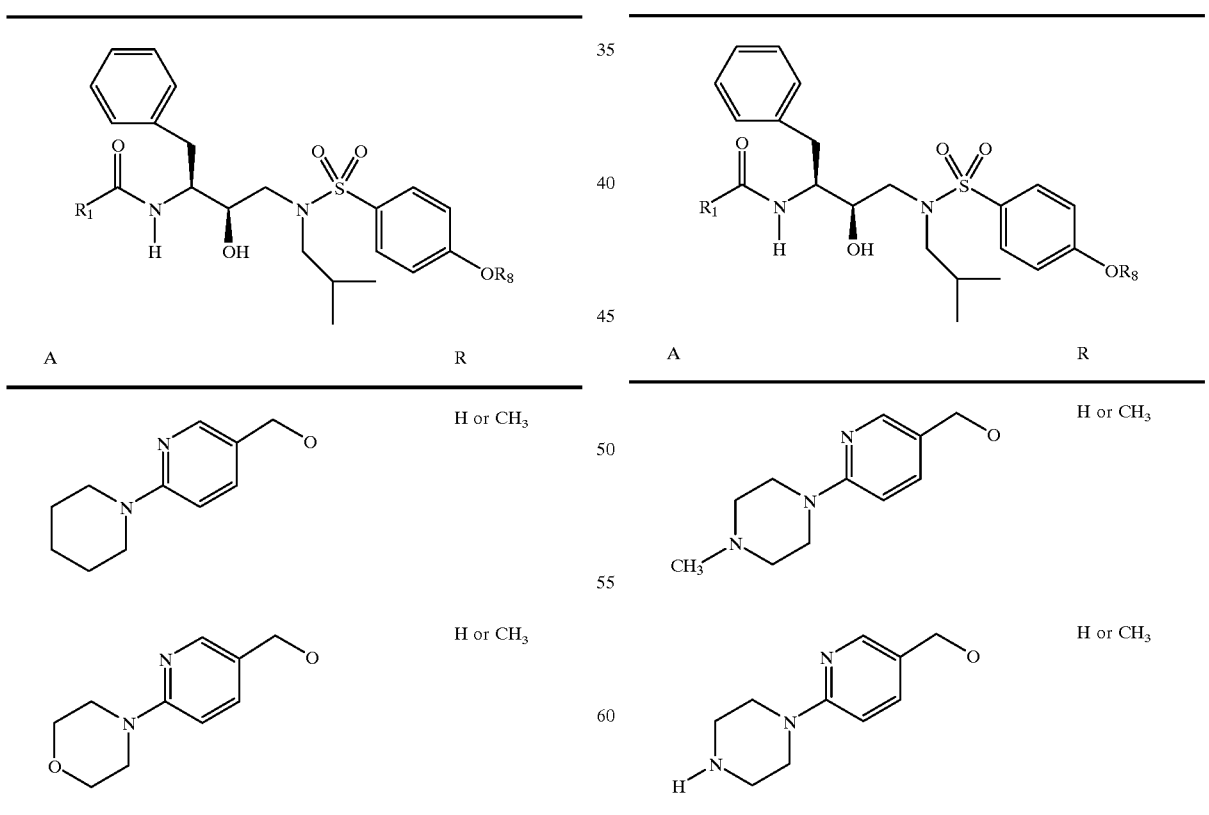

TABLE 16-continued
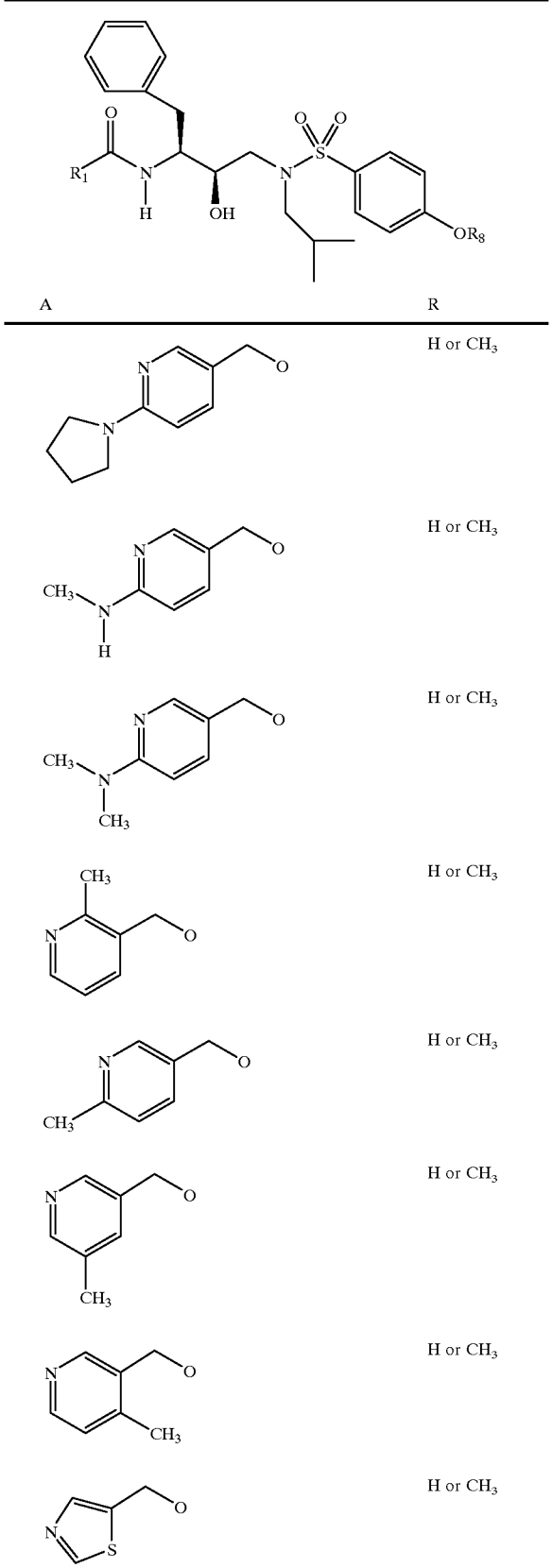
TABLE 16-continued
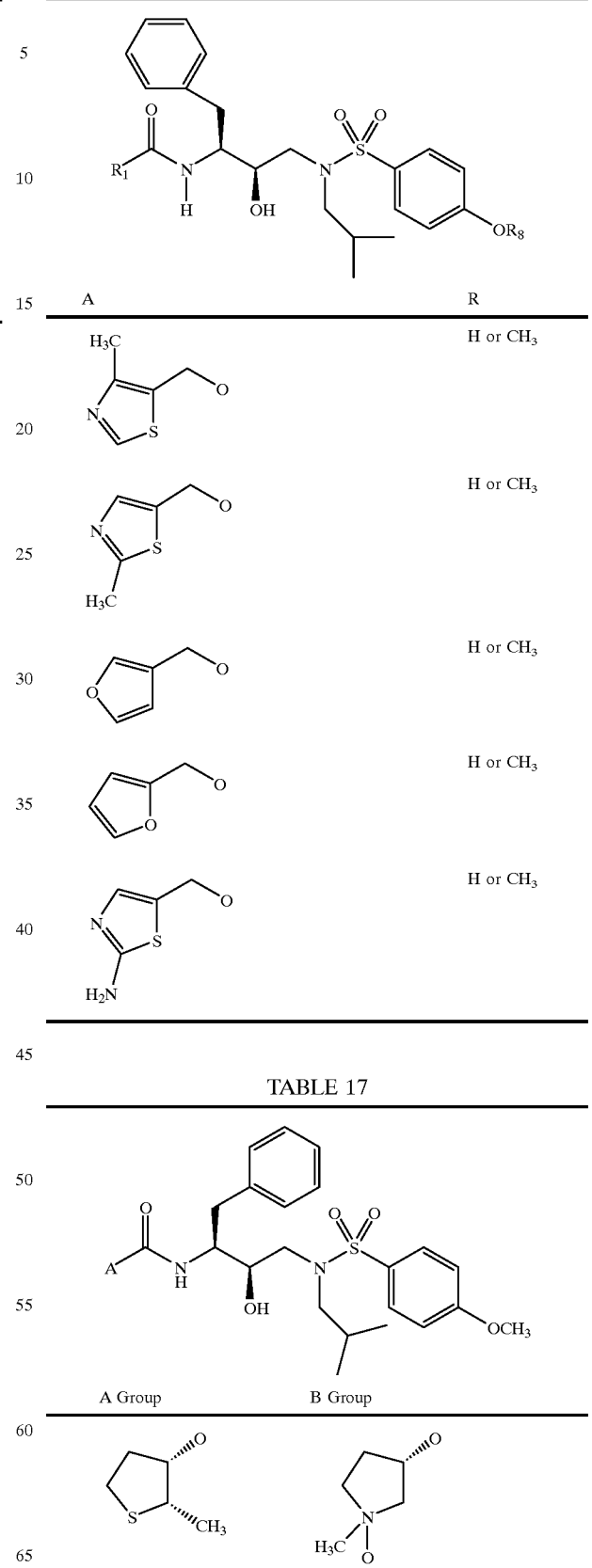
TABLE 17
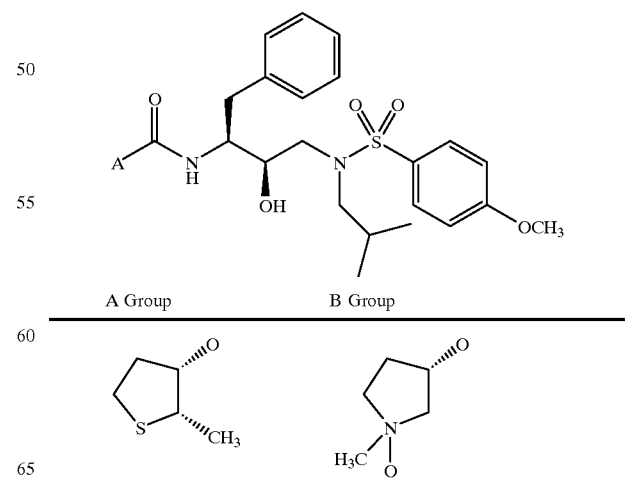

TABLE 17-continued
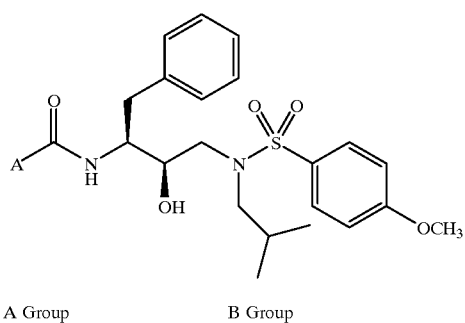
| A Group | B Group |
|---|---|
| 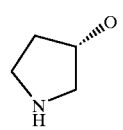 | |
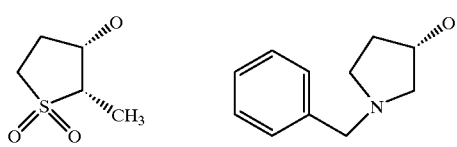
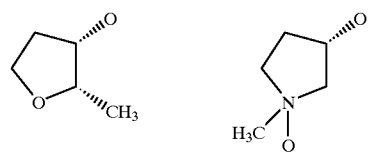
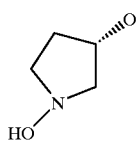
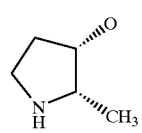
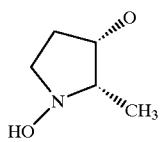
TABLE 17A
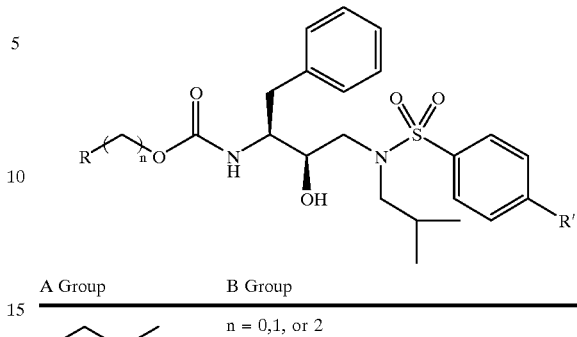
| A Group | B Group |
|---|---|
| 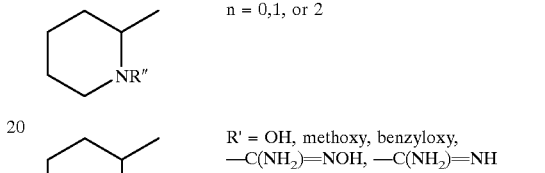 | n = 0, 1, or 2 |
| | R' = OH, methoxy, benzyloxy, —C(NH$_2$)=NOH, —C(NH$_2$)=NH |
| 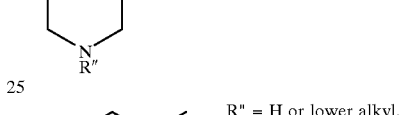 | R" = H or lower alkyl. |
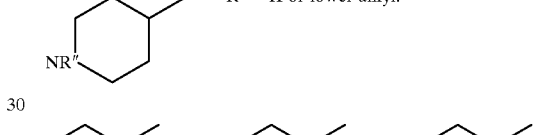
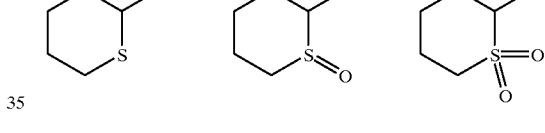
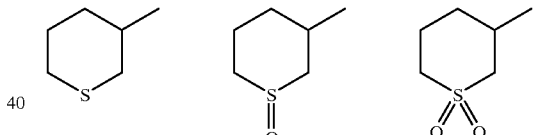
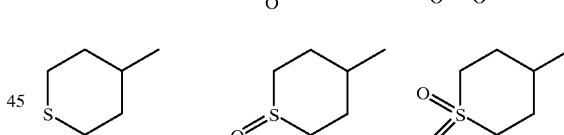
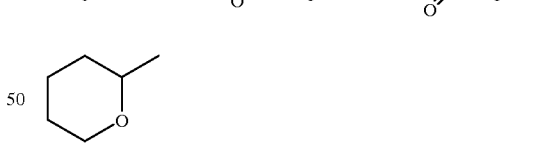

TABLE 17B
R = H or OH
$R^1$ = $CH_3$, $NH_2$, F, Cl or Br
$R^2$ = H or $CH_3$
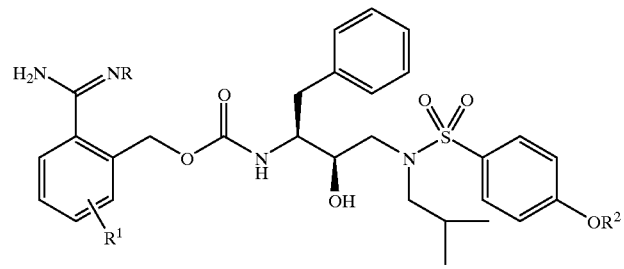
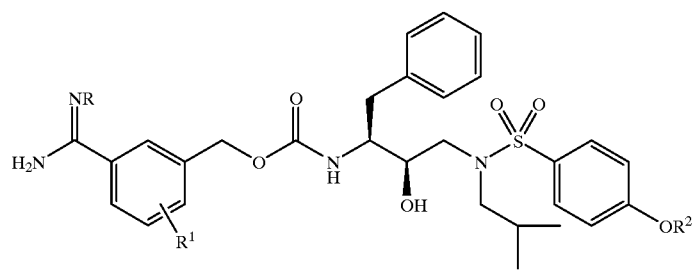
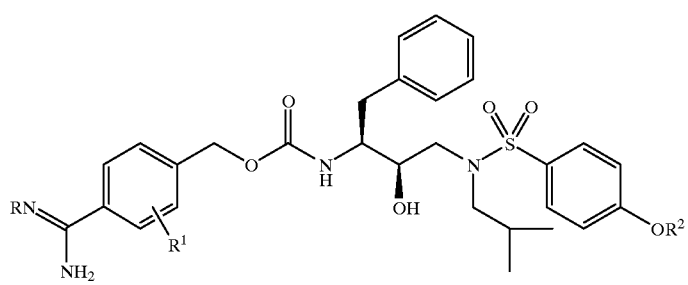
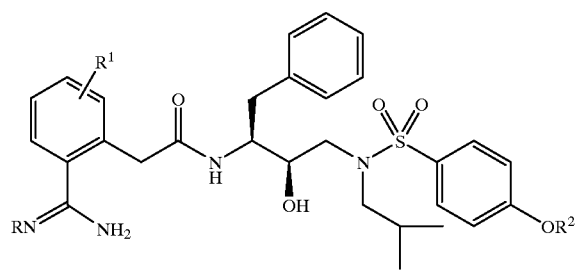
TABLE 17B-1
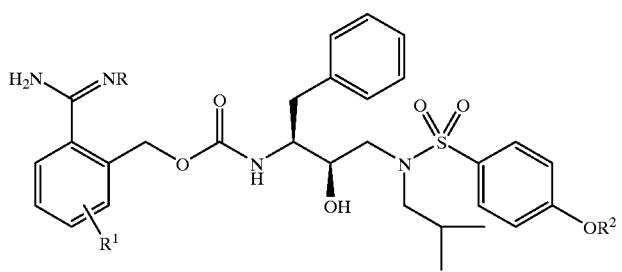

TABLE 17B-1-continued
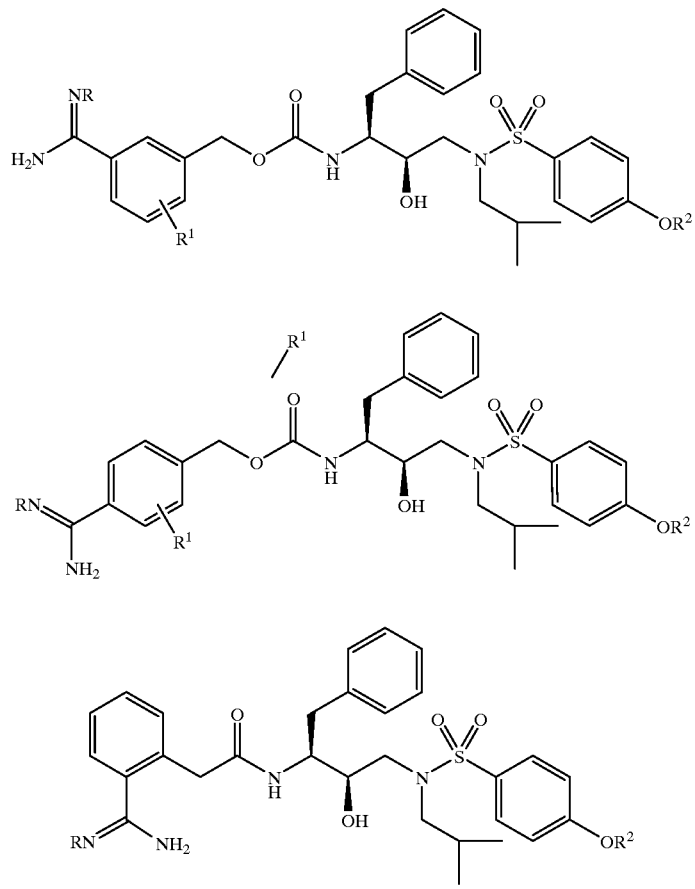
TABLE 17B-2
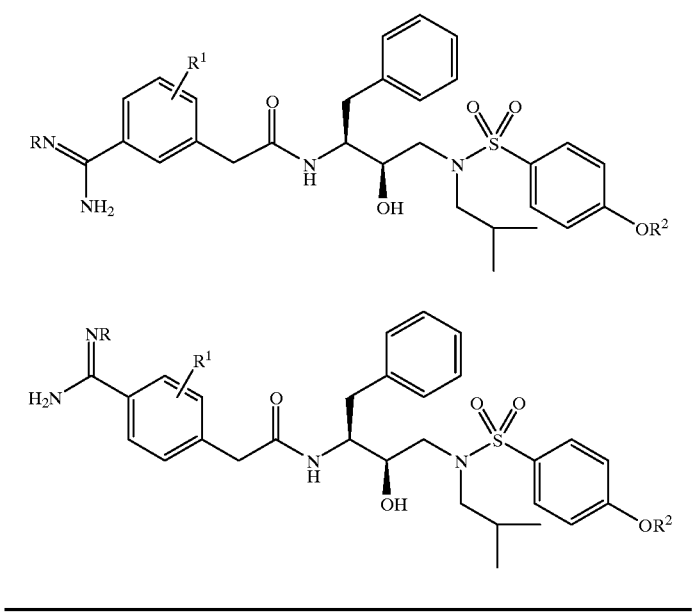

EXAMPLE 19

The compounds of the present invention are effective HIV protease inhibitors. Utilizing an enzyme assay as described below, the compounds set forth in the examples herein disclosed inhibited the HIV enzyme. The preferred compounds of the present invention and their calculated $IC_{50}$ (inhibiting concentration 50%, i.e., the concentration at which the inhibitor compound reduces enzyme activity by 50%) values are shown in Tables 18 through 21. The enzyme method is described below. The substrate is 2-Ile-Nle-Phe (p-$NO_2$)-Gln-Arg$NH_2$. The positive control is MVT-101 (Miller, M. et al, *Science*, 246, 1149 (1989)] The assay conditions are as follows:

Assay Buffer:
  20 mM sodium phosphate, pH 6.4
  20% glycerol
  1 mM EDTA
  1 mM DTT
  0.1% CHAPS.

The above described substrate is dissolved in DMSO, then diluted 10 fold in assay buffer. Final substrate concentration in the assay is 80 $\mu$M.

HIV protease is diluted in the assay buffer to a final enzyme concentration of 12.3 nanomolar, based on a molecular weight of 10,780.

The final concentration of DMSO is 14% and the final concentration of glycerol is 18%. The test compound is dissolved in DMSO and diluted in DMSO to 10× the test concentration; 10 $\mu$l of the enzyme preparation is added, the materials mixed and then the mixture is incubated at ambient temperature for 15 minutes. The enzyme reaction is initiated by the addition of 40 $\mu$l of substrate. The increase in fluorescence is monitored at 4 time points (0, 8, 16 and 24 minutes) at ambient temperature. Each assay is carried out in duplicate wells.

The preceding examples can be repeated with similar success by substituting the generically or specifically described reactants and/or operating conditions of this invention for those used in the preceding examples.

TABLE 18A

| Entry | Compound | $IC_{50}$ (namomolar) |
|---|---|---|
| 1 | | 16 |
| 2 | | 1.5 |
| 3 | | 1.4 |

TABLE 18A-continued
| Entry | Compound | IC$_{50}$ (namomolar) |
|---|---|---|
| 4 | 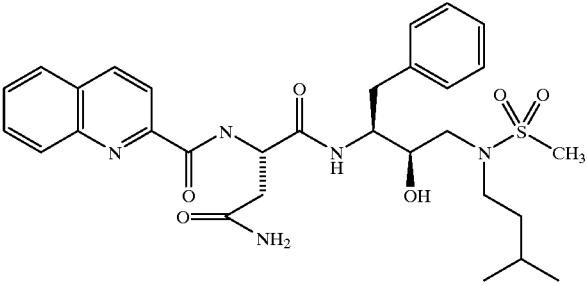 | 27 |
| 5 | 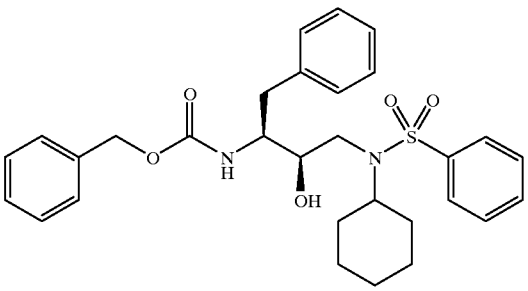 | 19 |
| 6 | 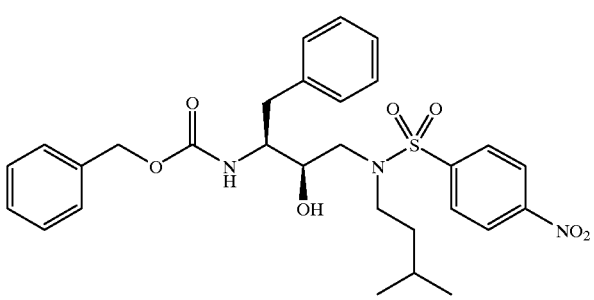 | 10 |
| 7 | 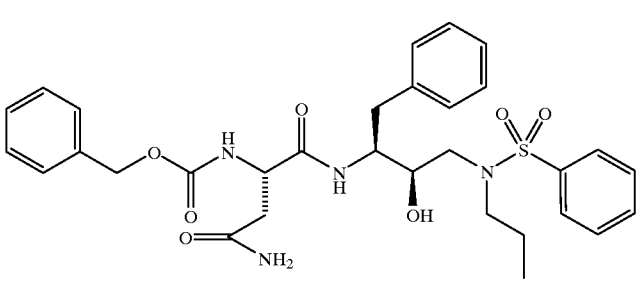 | 3.6 |
| 8 | 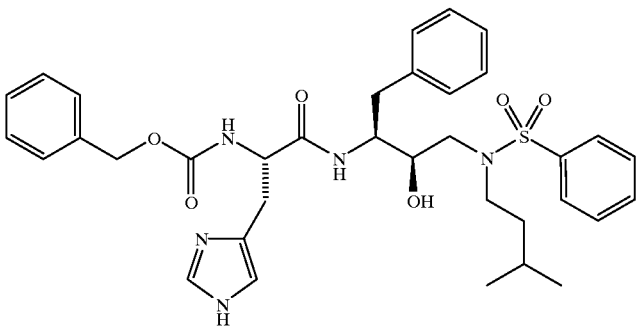 | 4.2 |

TABLE 18A-continued

| Entry | Compound | IC$_{50}$ (namomolar) |
|---|---|---|
| 9 | | 3.5 |
| 10 | | 100 |
| 11 | | 81 |
| 12 | | 20 |

| TABLE 19B | | | | | TABLE 19B-continued | | | |
|---|---|---|---|---|---|---|---|---|
| Ex. | Table | Entry | IC$_{50}$ (uM) or % inhib | | Ex. | Table | Entry | IC$_{50}$ (uM) or % inhib |
| 6 | 1a | 1 | 0.011 | | 6 | 1a | 41 | 24% @ 1 uM, 74% @ 10 uM |
| 6 | 1a | 2 | 0.010 | | 6 | 1a | 50 | 42% @ 1 uM, 89% @ 10 uM |
| 6 | 1a | 3 | 38% @ 1 uM, 79% @ 10 uM | | 6 | 1a | 51 | 31% @ 1 uM, 76% @ 10 uM |
| 6 | 1a | 4 | 0.016 | | 6 | 1a | 52 | 39% @ 1 uM, 81% @ 10 uM |
| 6 | 1a | 5 | 0.10 | | 6 | 1a | 53 | 0.049 |
| 6 | 1a | 6 | 36% @ 10 uM | | 6 | 1a | 54 | 0.0028 |
| 6 | 1a | 7 | 0.0096 | | 6 | 1a | 55 | 0.10 |
| 6 | 1a | 39 | 0.016 | | 6 | 1a | 56 | 0.0036 |
| 6 | 1a | 40 | 0.21 | | 16 | 3 | 1 | 0.081 |

TABLE 19B-continued

| Ex. | Table | Entry | IC$_{50}$ (uM) or % inhib |
|---|---|---|---|
| 16 | 3 | 2 | 38% @ 0.1 uM, 90% @ 1.0 uM |
| 16 | 3 | 4 | 0.0024 |
| 16 | 3 | 6 | 0.0018 |
| 16 | 3 | 8 | 0.003 |
| 16 | 3 | 10 | 0.0025 |
| 16 | 3 | 12 | 0.0016 |
| 16 | 4 | 102 | 0.0015 |
| 16 | 5 | 1 | 0.0014 |
| 16 | 5 | 14 | 0.0022 |
| 16 | 5 | 22 | 0.0018 |
| 16 | 5 | 33 | 0.0044 |
| 16 | 5 | 34 | 0.0020 |
| 16 | 7 | 31 | 0.0028 |
| 16 | 7 | 32 | 0.0015 |
| 16 | 11 | 1 | 0.13 |
| 16 | 11 | 9 | 41% @ 0.1 uM, 86% @ 1 uM |
| 16 | 12 | 10 | 0.0033 |
| 16 | 14 | 3 | 0.0049 |
| 16 | 14 | 10 | 0.0032 |

TABLE 20

| Table | Entry | IC$_{50}$ (uM) or % inhibtion |
|---|---|---|
| 1A | 3 | 0.02 |
| 5A | 1 | 0.04 |
| 5A | 3 | 0.02 |
| 5A | 4 | 0.01 |
| 5A | 5 | 0.026 |
| 5A | 6 | 0.023 |
| 5A | 7 | 0.007 |
| 5A | 9 | 0.067 |
| 5A | 11 | 0.018 |
| 5A | 12 | 0.006 |
| 5A | 13 | 0.0098 |
| 5A | 14 | 0.049 |
| 5A | 16 | 0.008 |
| 5A | 17 | 59% @ 10 µM |
| 5A | 18 | 0.13 |
| 5A | 19 | 0.092 |
| 5A | 20 | 85% @ 1 µM |
| 5A | 22 | 63% @ 1 µM |
| 5A | 24 | 0.047 |
| 5A | 25 | 0.014 |
| 5A | 26 | 0.005 |
| 5A | 28 | 0.015 |
| 5A | 29 | 0.19 |
| 5A | 30 | 0.03 |
| 5A | 31 | 0.02 |

EXAMPLE 20

The effectiveness of the compounds listed in Table 15 were determined in the above-described enzyme assay and in a CEM cell assay.

The HIV inhibition assay method of acutely infected cells is an automated tetrazolium based calorimetric assay essentially that reported by Pauwles et al, *J. Virol. Methods*, 20, 309–321 (1988). Assays were performed in 96-well tissue culture plates. CEM cells, a CD4+ cell line, were grown in RPMI-1640 medium (Gibco) supplemented with a 10% fetal calf serum and were then treated with polybrene (2 µg/ml). An 80 µl volume of medium containing 1×10$^4$ cells was dispensed into each well of the tissue culture plate. To each well was added a 100 µl volume of test compound dissolved in tissue culture medium (or medium without test compound as a control) to achieve the desired final concentration and the cells were incubated at 37° C. for 1 hour. A frozen culture of HIV-1 was diluted in culture medium to a concentration of 5×10$^4$ TCID$_{50}$ per ml (TCID$_{50}$=the dose of virus that infects 50% of cells in tissue culture), and a 20 µL volume of the virus sample (containing 1000 TCID$_{50}$ of virus) was added to wells containing test compound and to wells containing only medium (infected control cells). Several wells received culture medium without virus (uninfected control cells). Likewise, the intrinsic toxicity of the test compound was determined by adding medium without virus to several wells containing test compound. In summary, the tissue culture plates contained the following experiments:

|  | Cells | Drug | Virus |
|---|---|---|---|
| 1. | + | − | − |
| 2. | + | + | − |
| 3. | + | − | + |
| 4. | + | + | + |

In experiments 2 and 4 the final concentrations of test compounds were 1, 10, 100 and 500 µg/ml. Either azidothymidine (AZT) or dideoxyinosine (ddI) was included as a positive drug control. Test compounds were dissolved in DMSO and diluted into tissue culture medium so that the final DMSO concentration did not exceed 1.5% in any case. DMSO was added to all control wells at an appropriate concentration.

Following the addition of virus, cells were incubated at 37° C. in a humidified, 5% CO$_2$ atmosphere for 7 days. Test compounds could be added on days 0, 2 and 5 if desired. On day 7, post-infection, the cells in each well were resuspended and a 100 µl sample of each cell suspension was removed for assay. A 20 µL volume of a 5 mg/ml solution of 3-(4,5-dimethylthiazol-2-yl)-2,5-diphenyltetrazolium bromide (MTT) was added to each 100 µL cell suspension, and the cells were incubated for 4 hours at 27° C. in a 5% CO$_2$ environment. During this incubation, MTT is metabolically reduced by living cells resulting in the production in the cell of a colored formazan product. To each sample was added 100 µl of 10% sodium dodecylsulfate in 0.01 N HCl to lyse the cells, and samples were incubated overnight. The absorbance at 590 nm was determined for each sample using a Molecular Devices microplate reader. Absorbance values for each set of wells is compared to assess viral control infection, uninfected control cell response as well as test compound by cytotoxicity and antiviral efficacy.

TABLE 21

| Entry | Compound | IC$_{50}$ (nM) | EC$_{50}$ (nM) | TD$_{50}$ (nM) |
|---|---|---|---|---|
| 1 | | 16 | 55 | 27 |
| 2 | | 1 | 5 | 203 |
| 3 | | 1 | 11 | 780 |
| 4 | | 27 | 64 | 28 |

TABLE 21-continued

| Entry | Compound | IC$_{50}$ (nM) | EC$_{50}$ (nM) | TD$_{50}$ (nM) |
|---|---|---|---|---|
| 5 | | 19 | 88 | 11 |
| 6 | | >100 | 380 | 425 |
| 7 | | 3 | 25 | 39 |
| 8 | | 85 | 1200 | 24 |

TABLE 21-continued

| Entry | Compound | IC$_{50}$ (nM) | EC$_{50}$ (nM) | TD$_{50}$ (nM) |
|---|---|---|---|---|
| 9 | | 53 | 398 | 15 |
| 10 | | 45 | 700 | 12 |
| 11 | | 3 | 11 | 54 |
| 12 | | 2 | 12 | 7.5 |

TABLE 21-continued

| Entry | Compound | IC$_{50}$ (nM) | EC$_{50}$ (nM) | TD$_{50}$ (nM) |
|---|---|---|---|---|
| 13 | | 3 | <16 | |
| 14 | | 4 | 15 | 55,000 |
| 15 | | 5 | 38 | |
| 16 | | 9 | 80 | 62.000 |

TABLE 21-continued

| Entry | Compound | IC$_{50}$ (nM) | EC$_{50}$ (nM) | TD$_{50}$ (nM) |
|---|---|---|---|---|
| 17 | | 4 | 5 | 59,000 |
| 18 | | 8 | | |
| 19 | | 4 | | |
| 20 | | 4 | | |

TABLE 21-continued

| Entry | Compound | IC$_{50}$ (nM) | EC$_{50}$ (nM) | TD$_{50}$ (nM) |
|---|---|---|---|---|
| 21 | (pyridin-2-ylmethyl carbamate structure) | 73 | | |
| 22 | (pyridin-4-ylmethyl carbamate structure) | 15 | 18 | 31,000 |
| 23 | (pyrimidin-5-ylmethyl carbamate structure) | 2 | | |
| 24 | (benzyl carbamate structure) | 3 | | |

TABLE 21-continued
| Entry | Compound | IC$_{50}$ (nM) | EC$_{50}$ (nM) | TD$_{50}$ (nM) |
|---|---|---|---|---|
| 25 | 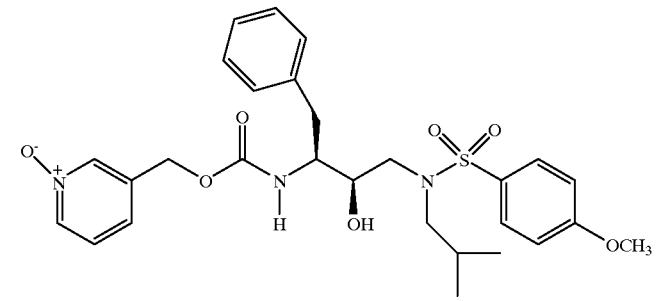 | 60 | 120 | 167,000 |
| 26 | 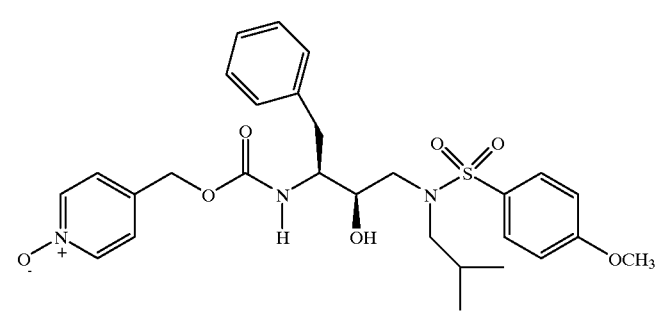 | | | |
| 27 | 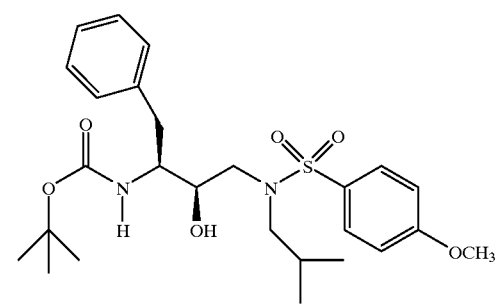 | 5 | 177 | 300,000 |
| 28 | 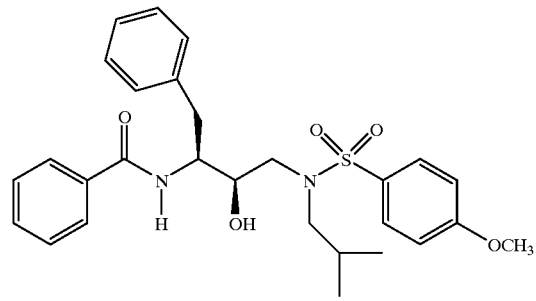 | 14 | 76 | 213,000 |

TABLE 21-continued

| Entry | Compound | IC$_{50}$ (nM) | EC$_{50}$ (nM) | TD$_{50}$ (nM) |
|---|---|---|---|---|
| 29 | | 5 | 105 | 196,000 |
| 30 | | 6 | 154 | 154,000 |
| 31 | | 10 | | |
| 32 | | 5 | 98 | 17,000 |

TABLE 21-continued

| Entry | Compound | IC$_{50}$ (nM) | EC$_{50}$ (nM) | TD$_{50}$ (nM) |
|---|---|---|---|---|
| 33 | | 18 | 68 | |
| 34 | | 67 | 188 | |
| 35 | | | | |
| 36 | | 310 | 898 | |

TABLE 21-continued

| Entry | Compound | IC$_{50}$ (nM) | EC$_{50}$ (nM) | TD$_{50}$ (nM) |
|---|---|---|---|---|
| 37 | | 7 | <20 | |
| 38 | | 4 | 1,100 | |
| 39 | | 16 | 269 | |
| 40 | | 3 | | |

TABLE 21-continued

| Entry | Compound | IC$_{50}$ (nM) | EC$_{50}$ (nM) | TD$_{50}$ (nM) |
|---|---|---|---|---|
| 41 | pyrimidin-5-ylmethyl carbamate of (2S,3R)-3-amino-1-[N-isobutyl-N-(4-hydroxybenzenesulfonyl)amino]-4-phenyl-2-butanol | 3 | 11 | |
| 42 | (3S)-tetrahydrothiophen-3-yl carbamate of (2S,3R)-3-amino-1-[N-isobutyl-N-(4-hydroxybenzenesulfonyl)amino]-4-phenyl-2-butanol | 2 | | |
| 43 | (3S)-1,1-dioxo-tetrahydrothiophen-3-yl carbamate of (2S,3R)-3-amino-1-[N-isobutyl-N-(4-hydroxybenzenesulfonyl)amino]-4-phenyl-2-butanol | 4 | | |
| 44 | (3S)-tetrahydrofuran-3-yl carbamate of (2S,3R)-3-amino-1-[N-isobutyl-N-(4-methoxybenzenesulfonyl)amino]-4-phenyl-2-butanol | 4 | 8 | |
| 45 | (3S)-tetrahydrofuran-3-yl carbamate of (2S,3R)-3-amino-1-[N-isobutyl-N-(4-hydroxybenzenesulfonyl)amino]-4-phenyl-2-butanol | 2 | 5 | |

TABLE 21-continued

| Entry | Compound | IC$_{50}$ (nM) | EC$_{50}$ (nM) | TD$_{50}$ (nM) |
|---|---|---|---|---|
| 46 | | 2 | | |
| 47 | | 3 | | |
| 48 | | 17 | 210 | |
| 49 | | 6 | <20 | |

TABLE 21-continued

| Entry | Compound | IC$_{50}$ (nM) | EC$_{50}$ (nM) | TD$_{50}$ (nM) |
|---|---|---|---|---|
| 50 | | | 14 | |
| 51 | | | 9 | |
| 52 | | | >100 | |
| 53 | | | 21 | |

TABLE 21-continued

| Entry | Compound | IC$_{50}$ (nM) | EC$_{50}$ (nM) | TD$_{50}$ (nM) |
|---|---|---|---|---|
| 54 | | | 10 | |
| 55 | | | 37 | |

The compounds of the present invention are effective antiviral compounds and, in particular, are effective retroviral inhibitors as shown above. Thus, the subject compounds are effective HIV protease inhibitors. It is contemplated that the subject compounds will also inhibit other retroviruses such as other lentiviruses in particular other strains of HIV, e.g. HIV-2, human T-cell leukemia virus, respiratory syncitial virus, simia immunodeficiency virus, feline leukemia virus, feline immuno-deficiency virus, hepadnavirus, cytomegalovirus and picornavirus. Thus, the subject compounds are effective in the treatment and/or proplylaxis of retroviral infections.

The subject compounds are also effective in preventing the growth of retroviruses in a solution. Both human and animal cell cultures, such as T-lymphocyte cultures, are utilized for a variety of well known purposes, such as research and diagnostic procedures including calibrators and controls. Prior to and during the growth and storage of a cell culture, the subject compounds may be added to the cell culture medium at an effective concentration to prevent the unexpected or undesired replication of a retrovirus that may inadvertently or unknowingly be present in the cell culture. The virus may be present originally in the cell culture, for example HIV is known to be present in human T-lymphocytes long before it is detectable in blood, or through exposure to the virus. This use of the subject compounds prevents the unknowing or inadvertent exposure of a potentially lethal retrovirus to a researcher or clinician.

Compounds of the present invention can possess one or more asymmetric carbon atoms and are thus capable of existing in the form of optical isomers as well as in the form of racemic or nonracemic mixtures thereof. The optical isomers can be obtained by resolution of the racemic mixtures according to conventional processes, for example by formation of diastereoisomeric salts by treatment with an optically active acid or base. Examples of appropriate acids are tartaric, diacetyltartaric, dibenzoyltartaric, ditoluoyltartaric and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers. Still another available method involves synthesis of covalent diastereoisomeric molecules by reacting compounds of Formula I with an optically pure acid in an activated form or an optically pure isocyanate. The synthesized diastereoisomers can be separated by conventional means such as chromatography, distillation, crystallization or sublimation, and then hydrolyzed to deliver the enantiomerically pure compound. The optically active compounds of Formula I can likewise be obtained by utilizing optically active starting materials. These isomers may be in the form of a free acid, a free base, an ester or a salt.

The compounds of the present invention can be used in the form of salts derived from inorganic or organic acids. These salts include but are not limited to the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxy-ethanesulfonate, lactate, maleate, methanesulfonate, nicotinate, 2-naphthalenesulfonate, oxalate, palmoate, pectinate, persulfate, 3-phenylpropionate, picrate, pivalate, propionate, succinate, tartrate, thiocyanate, tosylate, mesylate and undecanoate. Also, the basic nitrogen-containing groups can be quaternized with such agents as lower alkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids which may be employed to form pharmaceutically acceptable acid addition salts include such inorganic acids as hydrochloric acid, sulphuric acid and phosphoric acid and such organic acids as oxalic acid, maleic acid, succinic acid and citric acid. Other examples include salts with alkali metals or alkaline earth metals, such as sodium, potassium, calcium or magnesium or with organic bases.

Total daily dose administered to a host in single or divided doses may be in amounts, for example, from 0.001 to 10 mg/kg body weight daily and more usually 0.01 to 1 mg. Dosage unit compositions may contain such amounts of submultiples thereof to make up the daily dose.

The amount of active ingredient that may be combined with the carrier materials to produce a single dosage form will vary depending upon the host treated and the particular mode of administration.

The dosage regimen for treating a disease condition with the compounds and/or compositions of this invention is selected in accordance with a variety of factors, including the type, age, weight, sex, diet and medical condition of the patient, the severity of the disease, the route of administration, pharmacological considerations such as the activity, efficacy, pharmacokinetic and toxicology profiles of the particular compound employed, whether a drug delivery system is utilized and whether the compound is administered as part of a drug combination Thus, the dosage regimen actually employed may vary widely and therefore may deviate from the preferred dosage regimen set forth above.

The compounds of the present invention may be administered orally, parenterally, by inhalation spray, rectally, or topically in dosage unit formulations containing conventional nontoxic pharmaceutically acceptable carriers, adjuvants, and vehicles as desired. Topical administration may also involve the use of transdermal administration such as transdermal patches or iontophoresis devices. The term parenteral as used herein includes subcutaneous injections, intravenous, intramuscular, intrasternal injection, or infusion techniques.

Injectable preparations, for example, sterile injectable aqueous or oleaginous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are water, Ringer's solution, and isotonic sodium chloride solution In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Suppositories for rectal administration of the drug can be prepared by mixing the drug with a suitable nonirritating excipient such as cocoa butter and polyethylene glycols which are solid at ordinary temperatures but liquid at the rectal temperature and will therefore melt in the rectum and release the drug.

Solid dosage forms for oral administration may include capsules, tablets, pills, powders, and granules. In such solid dosage forms, the active compound may be admixed with at least one inert diluent such as sucrose lactose or starch. Such dosage forms may also comprise, as in normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, and sweetening, flavoring, and perfuming agents.

While the compounds of the invention can be administered as the sole active pharmaceutical agent, they can also be used in combination with one or more immunomodulators, antiviral agents or other antiinfective agents. For example, the compounds of the invention can be administered in combination with AZT, DDI, DDC or with glucosidase inhibitors, such as N-butyl-1-deoxynojirimycin or prodrugs thereof, for the prophylaxis and/or treatment of AIDS. When administered as a combination, the therapeutic agents can be formulated as separate compositions which are given at the same time or different times, or the therapeutic agents can be given as a single composition.

The foregoing is merely illustrative of the invention and is not intended to limit the invention to the disclosed compounds. Variations and changes which are obvious to one skilled in the art are intended to be within the scope and nature of the invention which are defined in the appended claims.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A compound represented by the formula:

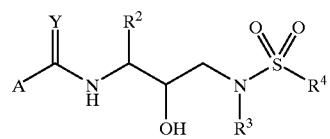

or a pharmaceutically acceptable salt thereof wherein $R^2$ is an alkyl, aryl, cycloalkyl, cycloalkylalkyl or aralkyl radical, which radical is optionally substituted with a radical selected from the group consisting of alkyl, halo, nitro, cyano, $CF_3$, $-OR^9$, and $-SR^9$ radicals, wherein $R^9$ is hydrogen or alkyl radicals;

$R^3$ is alkyl, haloalkyl, alkenyl, alkynyl, hydroxyalkyl, alkoxyalkyl, alkylthioalkyl, alkylsulfonylalkyl, cycloalkyl, cycloalkylalkyl, heterocycloalkyl, heteroaryl, heterocycloalkylalkyl, aryl, aralkyl or heteroaralkyl radicals;

$R^4$ is heterocycloalkyl, heteroaryl or aryl radicals;

Y is O or S; and

A is heterocycloalkyl, heterocycloalkoxy, heterocycloalkylalkyl, heterocycloalkylalkoxy, heteroaralkyl, heteroaralkoxy, heteroaryloxy or heteroaryl radicals; and wherein alkyl, alone or in combination, is a straight-chain or branched-chain alkyl radical containing 1 to 8 carbon atoms; alkenyl, alone or in combination, is a straight-chain or branched-chain hydrocarbon radical having at least one double bond and containing 2 to 8 carbon atoms; alkynyl, alone or in combination, is a straight-chain or branched chain hydrocarbon radical having at least one triple bond and containing 2 to 10 carbon atoms; aryl, alone or in combination, is an unsubstituted phenyl or naphthyl radical or a phenyl or naphthyl radical substituted with alkyl, alkoxy, halogen, hydroxy, amino, alkylamino, dialkylamino, nitro, cyano, carboxy, alkoxycarbonyl, amido, alkylamido, dialkylamido, trifluoromethyl, methylthio, methylsulfinyl or methylsulfonyl radicals; cycloalkyl, alone or in combination, is a saturated or partially saturated monocyclic, bicyclic or tricyclic alkyl radical wherein each cyclic moiety contains 3 to 8 carbon atoms; heterocycloalkyl, alone or in combination, is a monocyclic, bicyclic or tricyclic heterocycle radical having 1–4 nitrogen, nitrogen oxide, oxygen, sulphur, sulfone or sulfoxide heteroatom ring members, optionally benz-fused and optionally substituted on one or more carbon atoms by halogen, alkyl, alkoxy, hydroxy, oxo, aryl or aralkyl radicals, or on a secondary nitrogen atom by hydroxy, alkyl, aralkoxycarbonyl, alkanoyl, phenyl or phenylalkyl radicals; and heteroaryl, alone or in combination, is an aromatic heterocycloalkyl, optionally substituted with respect to aryl and heterocycloalkyl radicals.

2. Compound of claim 1 or a pharmaceutically acceptable salt thereof wherein $R^2$ represents alkyl, cycloalkylalkyl or aralkyl radicals, which radicals are optionally substituted with alkyl, halogen or —$OR^9$ radicals, wherein $R^9$ represents hydrogen or alkyl radicals; and $R^3$ is alkyl, alkenyl, alkynyl, hydroxyalkyl, alkoxyalkyl, alkylthioalkyl, alkylsulfonylalkyl, cycloalkyl, cycloalkylalkyl, heterocycloalkylalkyl, aryl, aralkyl or heteroaralkyl radicals;

wherein heterocycloalkyl, alone or in combination, is a 5–6 ring membered monocyclic heterocycle radical having 1–4 nitrogen, nitrogen oxide, oxygen, sulphur, sulfone or sulfoxide heteroatom ring members, optionally benz-fused and optionally substituted on one or more carbon atoms by halogen, alkyl, alkoxy, hydroxy, oxo, aryl or aralkyl radicals, or on a secondary nitrogen atom by hydroxy, alkyl, aralkoxycarbonyl, alkanoyl, phenyl or phenylalkyl radicals; and heteroaryl, alone or in combination, is an aromatic heterocycloalkyl, optionally substituted with respect to aryl and heterocycloalkyl radicals.

3. Compound of claim 2 or a pharmaceutically acceptable salt thereof wherein

A is heterocycloalkyl, heterocycloalkoxy, heterocycloalkylalkyl, heteroaralkoxy or heteroaryl radicals;

$R^3$ represents alkyl, cycloalkyl or cycloalkylalkyl radicals; and $R^4$ is heterocycloalkyl or aryl radicals;

wherein alkyl, alone or in combination, is a straight-chain or branched-chain hydrocarbon radical containing from 1–5 carbon atoms; alkenyl, alone or in combination, is a straight-chain or branched-chain hydrocarbon radical having at least one double bond and containing from 2–5 carbon atoms; alkynyl, alone or in combination, is a straight-chain or branched-chain hydrocarbon radical having at least one triple bond and containing from 2–5 carbon atoms; heterocycloalkyl, alone or in combination, is a 5–6 ring membered heterocycle or a benzfused 5–6 ring membered heterocycle having one or two nitrogen, nitrogen oxide, oxygen, sulphur, sulfone or sulfoxide heteroatoms; and heteroaryl means an aromatic 5–6 ring membered heterocycle or an aromatic benzfused 5–6 ring membered heterocycle having one or two nitrogen, nitrogen oxide, oxygen, sulphur or sulfone heteroatoms.

4. Compound of claim 3 or a pharmaceutically acceptable salt thereof wherein

A is heterocycloalkyl or heterocycloalkoxy radicals;

$R^2$ represents alkyl, cycloalkylalkyl or aralkyl radicals;

$R^3$ represents alkyl, cycloalkyl or cycloalkylalkyl radicals;

$R^4$ is an aryl radical; and

Y is O;

wherein heterocycloalkyl, alone or in combination, is a 5–6 ring membered heterocycle having an oxygen, sulphur, sulfone or sulfoxide heteroatom.

5. Compound of claim 4 or a pharmaceutically acceptable salt thereof wherein

A is heterocycloalkyl or heterocycloalkoxy radicals;

$R^2$ represents butyl, benzyl, cyclohexylmethyl or 2-naphthylmethyl radicals;

$R^3$ represents isobutyl, isoamyl, cyclohexyl, cyclohexylmethyl, n-butyl or n-propyl radicals; and $R^4$ is phenyl, methoxyphenyl, cyanophenyl, chlorophenyl, hydroxyphenyl, nitrophenyl, fluorophenyl or aminophenyl radical;

wherein heterocycloalkyl, alone or in combination, is a 5–6 ring membered heterocycle having an oxygen, sulphur, sulfone or sulfoxide heteroatom.

6. Compound of claim 2 or a pharmaceutically acceptable salt thereof wherein $R^2$ is butyl, cyclohexylmethyl, benzyl, 4-fluorobenzyl or naphthylmethyl radicals;

$R^3$ is methyl, ethyl, propyl, butyl, pentyl, hexyl, iso-butyl, iso-amyl, 3-methoxypropyl, 3-methylthiopropyl, 4-methylthiobutyl, 4-methylsulfonylbutyl, 2-(1-morpholino)ethyl, 4-hydroxybutyl, allyl, propargyl, cyclohexylmethyl, cyclopropylmethyl, phenyl, benzyl, 4-fluorobenzyl, 4-methoxybenzyl, 1-phenylethyl, 2-phenylethyl, naphthylmethyl, 3-pyridylmethyl or 4-pyridylmethyl radicals;

$R^4$ is phenyl, naphthyl, chlorophenyl, fluorophenyl, hydroxyphenyl, methylphenyl, methoxyphenyl, ethoxyphenyl, methylthiophenyl, methylsulfinylphenyl, methylsulfonylphenyl, acetamidophenyl, methoxycarbonylphenyl, aminophenyl, dimethylaminophenyl, nitrophenyl, trifluoromethylphenyl or thienyl radicals;

Y is O; and

A is quinolinyl, indolyl, pyridyl, methylpyridyl, furanyl, oxazolyl, thiazolyl, pyridylmethoxy, hydroxypyridylmethoxy, aminopyridylmethoxy, pyrimidinylmethoxy, N-oxo-pyrimidinylmethoxy, thiazolylmethoxy, tetrahydrothiophenoxy, 1,1-dioxotetrahydrothiophenoxy or tetrahydrofuranoxy radicals.

7. A compound of claim 1 which is

Carbamic acid, [2R-hydroxy-3-[(4-hydroxyphenylsulfonyl)(2-methylpropyl)amino]-1S-(phenylmethyl)propyl-, 3(S)-1,1-dioxotetrahydrothiophen-3-yl-ester;

Carbamic acid, [2R-hydroxy-3-[(4-methoxyphenylsulfonyl)(2-methylpropyl)amino]-1S-(phenylmethyl)propyl-, 3(S)-1,1-dioxotetrahydrothiophen-3-yl-ester;

Carbamic acid, [2R-hydroxy-3-[(4-methoxyyphenylsulfonyl)(2-methylpropyl)amino]-1S-(phenylmethyl)propyl-, 3-S-tetrahydrothiophen-3-yl-ester;

Carbamic acid, [2R-hydroxy-3-[(4-hydroxyphenylsulfonyl)(2-methylpropyl)amino]-1S-(phenylmethyl)propyl-, 3-S-tetrahydrothiophen-3-yl-ester;

Carbamic acid, [2R-hydroxy-3-[(4-hydroxyphenylsulfonyl)(2-methylpropyl)amino]-1S-(phenylmethyl)propyl-, 3-S-tetrahydrofuran-3-yl-ester;

Carbamic acid, [2R-hydroxy-3-[(4-methoxyphenylsulfonyl)(2-methylpropyl)amino]-1S-(phenylmethyl)propyl-, 3-S-tetrahydrofuran-3-yl-ester;

Carbamic acid, [2R-hydroxy-3-[[(4-methoxyphenyl)sulfonyl](2-methylpropyl)amino]-1S-(phenylmethyl)propyl]-, 5-(thiazolyl)methyl ester;

Carbamic acid, [2R-hydroxy-3-[[(4-hydroxyphenyl)sulfonyl](2-methylpropyl)amino]-1S-(phenylmethyl)propyl]-, 5-(thiazolyi)methyl ester;

Carbamic acid, [2R-hydroxy-3-[[(4-methoxyphenyl)sulfonyl](2-methylpropyl)amino]-1S-(phenylmethyl)propyl]-, 3-(6-aminopyridyl)methyl ester;

Carbamic acid, [2R-hydroxy-3-[[(4-hydroxyphenyl)sulfonyl](2-methylpropyl)amino]-1S-(phenylmethyl)propyl]-, 3-(6-aminopyridyl)methyl ester;

Carbamic acid, [2R-hydroxy-3-[[(4-methoxyphenyl)sulfonyl](2-methylpropyl)amino]-1S-(phenylmethyl)propyl]-, 3-(6-hydroxypyridyl)methyl ester;

Carbamic acid, [2R-hydroxy-3-[[(4-hydroxyphenyl)sulfonyl](2-methylpropyl)amino]-1S-(phenylmethyl)propyl]-, 5-pyrimidyimethyl ester;

4-Pyridinecarboxamide, N-[2R-hydroxy-3-[[(4-methoxyphenyl)sulfonyl](2-methylpropyl)amino]-1S-(phenylmethyl)propyl];

Carbamic acid, [2R-hydroxy-3-[[(4-methoxyphenyl)sulfonyl](2-methylpropyl)amino]-1S-(phenylmethyl)propyl]-, 3-pyridylmethyl ester;

Carbamic acid, [2R-hydroxy-3-[[(4-methoxyphenyl)sulfonyl](2-methylpropyl)amino]-1S-(phenylmethyl)propyl]-, 3-pyridylmethyl ester, N-oxide;

Carbamic acid, [2R-hydroxy-3-[[phenylsulfonyl](2-methylpropyl)amino]-1S-(phenylmethyl)propyl]-, 3-pyridylmethyl ester;

Carbamic acid, [2R-hydroxy-3-[[(4-methoxyphenyl)sulfonyl](2-methylpropyl)amino]-1S-(phenylmethyl)propyl]-, 4-pyridylmethyl ester;

Carbamic acid, [2R-hydroxy-3-[[(4-methoxyphenyl)sulfonyl](2-methylpropyl)amino]-1S-(phenylmethyl)propyl]-, 4-pyridylmethyl ester, N-oxide;

Carbamic acid, [2R-hydroxy-3-[[(4-chlorophenyl)sulfonyl](2-methylpropyl)amino]-1S-(phenylmethyl)propyl]-, 3-pyridylmethyl ester;

Carbamic acid, [2R-hydroxy-3-[[(4-nitrophenyl)sulfonyl](2-methylpropyl)amino]-1S-(phenylmethyl)propyl]-, 3-pyridylmethyl ester;

Carbamic acid, [2R-hydroxy-3-[[(4-fluorophenyl)sulfonyl](2-methylpropyl)amino]-1S-(phenylmethyl)propyl]-, 3-pyridylmethyl ester;

Carbamic acid, [2R-hydroxy-3-[[(4-hydroxyphenyl)sulfonyl](2-methylpropyl)amino]-1S-(phenylmethyl)propyl]-, 3-pyridylmethyl ester; or Carbamic acid, [2R-hydroxy-3-[[(4-methoxyphenyl)sulfonyl](2-methylpropyl)amino]-1S-(phenylmethyl)propyl]-, 5-pyrimidylmethyl ester.

8. A pharmaceutical composition comprising a compound of claim 1 and a pharmaceutically acceptable carrier.

9. The compound of claim 1 wherein said heterocycloalkyl or heteroaryl is selected from optionally substituted pyrrolidinyl, piperidinyl, piperazinyl, morpholinyl, thiamorpholinyl, pyrrolyl, imidazolyls, pyrazolyl, pyridyl, pyrazinyl, pyrimidinyl, furyl, thienyl, triazolyl, oxazolyl, thiazolyl, indolyls, quinolynyls, isoquinolinyls, tetrahydroquinolinyls, 1,2,3,4-tetrahydroisoquinolinyls, quinoxalinyl, β-carbolinyl, 2-benzofurancarbonyl, and benzimidazolyls radicals.

10. A compound represented by the formula:

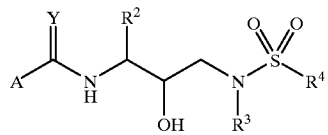

or a pharmaceutically acceptable salt thereof wherein $R^2$ is an aralkyl radical;

$R^3$ is alkyl;

$R^4$ is an aryl radical;

Y is O; and

A is a 5-membered ring containing one oxygen or one sulfur atom.

11. Compound of claim 1 wherein said heterocycloalkyl is a 5–6 ring membered monocyclic, heterocycle radical having 1–4 nitrogen, nitrogen oxide, oxygen, sulphur, sulfone or sulfoxide heteroatom ring members, optionally benzfused and optionally substituted on one or more carbon atoms by halogen, alkyl, alkoxy, hydroxy, oxo aryl or aralkyl radicals, or on a secondary nitrogen atom by hydroxy alkyl, aralkoxycarbonyl, alkanoyl, phenyl or phenylalkyl radicals, and said heteroaryl is an aromatic heterocycloalkyl optionally benzfused and optionally substituted.

12. Compound of claim 11 wherein said heterocycloalkyl is a 5–6 ring membered heterocycle or a benzfused 5–6 ring membered heterocycle having one or two nitrogen, nitrogen oxide, oxygen, sulfur, sulfone or sulfoxide heteroatoms; and said heteroaryl is an aromatic 5–6 ring membered heterocycle or an aromatic benzfused 5–6 ring membered heterocycle having one or two nitrogen, nitrogen oxide, oxygen sulphur or sulfone heteroatoms.

* * * * *